US008426602B2

(12) United States Patent
Meibom et al.

(10) Patent No.: US 8,426,602 B2
(45) Date of Patent: Apr. 23, 2013

(54) HETEROARYL-SUBSTITUTED DICYANOPYRIDINES AND THEIR USE

(75) Inventors: Daniel Meibom, Leverkusen (DE); Alexandros Vakalopoulos, Hilden (DE); Barbara Albrecht-Küpper, Wülfrath (DE); Katja Zimmermann, Düsseldorf (DE); Peter Nell, Wuppertal (DE); Frank Süßmeier, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 12/922,172

(22) PCT Filed: Feb. 26, 2009

(86) PCT No.: PCT/EP2009/001352
§ 371 (c)(1),
(2), (4) Date: May 16, 2011

(87) PCT Pub. No.: WO2009/112155
PCT Pub. Date: Sep. 17, 2009

(65) Prior Publication Data
US 2011/0207698 A1    Aug. 25, 2011

(30) Foreign Application Priority Data

Mar. 11, 2008   (DE) .......................... 10 2008 013 587

(51) Int. Cl.
*C07D 211/78*    (2006.01)
*A61K 31/695*    (2006.01)

(52) U.S. Cl.
USPC ........................................... 546/287; 514/63

(58) Field of Classification Search .................. None
See application file for complete search history.

(56) References Cited

U.S. PATENT DOCUMENTS

| | | | |
|---|---|---|---|
| 4,052,510 A | 10/1977 | Simpson et al. | |
| 5,670,525 A | 9/1997 | Urbahns et al. | |
| 5,889,002 A | 3/1999 | Nielsen et al. | |
| 6,191,280 B1 | 2/2001 | Hamprecht et al. | |
| 6,586,441 B2 | 7/2003 | Barroni et al. | |
| 6,632,823 B1 | 10/2003 | Vernier et al. | |
| 6,693,102 B2 | 2/2004 | Stasch et al. | |
| 6,706,717 B2 | 3/2004 | Barrish et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 7,045,631 B2 | 5/2006 | Rosentreter et al. | |
| 7,078,417 B2 | 7/2006 | Rosentreter et al. | |
| 7,109,218 B2 | 9/2006 | Rosentreter et al. | |
| 7,129,255 B2 | 10/2006 | Rosentreter et al. | |
| 7,135,486 B1 | 11/2006 | Rosentreter et al. | |
| 7,173,036 B2 | 2/2007 | Sircar et al. | |
| 7,173,037 B2 | 2/2007 | Alonso-Alija et al. | |
| 7,186,716 B2 | 3/2007 | Wei et al. | |
| 7,674,825 B2 | 3/2010 | Alonso-Alija et al. | |
| 7,692,017 B2 | 4/2010 | Dinsmore et al. | |
| 7,705,043 B2 | 4/2010 | Alonso-Alija et al. | |
| 7,709,504 B2 | 5/2010 | Krahn et al. | |
| 7,781,470 B2 | 8/2010 | Alonso-Alija et al. | |
| 7,825,255 B2 | 11/2010 | Rosentreter et al. | |
| 7,855,219 B2 | 12/2010 | Rosentreter et al. | |
| 7,932,259 B2 | 4/2011 | Nakazato et al. | |
| 7,951,811 B2 | 5/2011 | Nakazato et al. | |
| 2003/0232860 A1 | 12/2003 | Harada et al. | |
| 2004/0162427 A1 | 8/2004 | Rosentreter et al. | |
| 2004/0176446 A1 | 9/2004 | Alonso-Alija et al. | |
| 2005/0182105 A1 | 8/2005 | Nirschi et al. | |
| 2005/0227972 A1 | 10/2005 | Rosentreter et al. | |
| 2005/0250774 A1 | 11/2005 | Ono et al. | |
| 2006/0264432 A1 | 11/2006 | Rosentreter et al. | |
| 2007/0066630 A1 | 3/2007 | Palani et al. | |
| 2007/0213372 A1 | 9/2007 | Rosentreter | |
| 2007/0293670 A1 | 12/2007 | Nakazato et al. | |
| 2008/0167321 A1 | 7/2008 | Kamboj et al. | |
| 2008/0269300 A1 | 10/2008 | Erguden | |
| 2009/0221649 A1 | 9/2009 | Krahn et al. | |
| 2010/0009973 A1 | 1/2010 | Rhodes et al. | |
| 2010/0022544 A1 | 1/2010 | Nell | |
| 2010/0048641 A1 | 2/2010 | Nell et al. | |
| 2010/0069363 A1 | 3/2010 | Nell | |
| 2010/0093728 A1 | 4/2010 | Nell | |

(Continued)

FOREIGN PATENT DOCUMENTS

| | | |
|---|---|---|
| CA | 2698170 | 2/2009 |
| EP | 0 608 565 A1 | 12/1993 |

(Continued)

OTHER PUBLICATIONS

Vippagunta, S. Adv Drug Deliv Rev 2001 vol. 48, pp. 3-26.*
Reddy, T. et al. J. Med. Chem. 2006, vol. 49, pp. 607-615.*
Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.
Avila, et al.: A1-, A2A- and A3-subtype adenosine receptors modulate intraocular pressure in the mouse, British Journal of Pharmacology, 2001, 134:241-245.
Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.

(Continued)

*Primary Examiner* — D M Seaman
*Assistant Examiner* — Heidi Reese
(74) *Attorney, Agent, or Firm* — Karen B. King

(57) ABSTRACT

The present application relates to novel heteroaryl-substituted dicyanopyridines, to processes for their preparation, to their use for the treatment and/or prophylaxis of diseases and to their use for preparing medicaments for the treatment and/or prophylaxis of diseases, preferably for the treatment and/or prevention of cardiovascular disorders.

5 Claims, No Drawings

U.S. PATENT DOCUMENTS

| | | |
|---|---|---|
| 2010/0197609 A1 | 8/2010 | Vakalopoulos |
| 2011/0130377 A1 | 6/2011 | Nell |
| 2011/0136871 A1 | 6/2011 | Hübsch et al. |
| 2011/0207698 A1 | 8/2011 | Meibom |
| 2011/0237629 A1 | 9/2011 | Meibom et al. |
| 2011/0294718 A1 | 12/2011 | Lerchen |
| 2011/0294719 A1 | 12/2011 | Lerchen |

FOREIGN PATENT DOCUMENTS

| | | |
|---|---|---|
| JP | 09-132529 | 5/1997 |
| JP | 10-324687 | 12/1998 |
| JP | 2003-183254 | 7/2003 |
| WO | 95/34563 | 12/1995 |
| WO | 97/27177 A2 | 7/1997 |
| WO | 99/03861 A1 | 1/1999 |
| WO | WO 0162233 A2 * | 8/2001 |
| WO | 02/48115 A2 | 6/2002 |
| WO | 02/50071 A1 | 6/2002 |
| WO | 03/091246 | 11/2003 |
| WO | 2004/014372 A1 | 2/2004 |
| WO | 2004/054505 A2 | 7/2004 |
| WO | 2005/007647 | 1/2005 |
| WO | 2007/073855 | 7/2007 |
| WO | 2008/008059 | 1/2008 |

OTHER PUBLICATIONS

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible Derivatives for Various Functional Groups and Chemical Entities," Elsevier Science Publishers B.V., 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods:A New Approach to the Arndt-Eistert Synthesis," Tetrahedron Letters, 2001, 42: 7099-7102.

Crosson: "Intraoccular Pressure Responses to the Adenosine Agonist Cyclohexyladenosine: Evidence for a Dual Mechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyanopyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5-Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b]pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using α,β-Unsaturated Nitriles: Facile Synthesis of Pyridine Derivatives," Synthesis Communications, Jul. 1981, pp. 531-533.

Klotz, et al.:"Comparative Pharmacology of Human Adenosine Receptor Subtypescharacterization of Stably Transfected Receptors in CHO Cells," Naunyn-Schmiedeberg's Arch Pharmacol, 1998, 357:1-9.

Klotz:"Adenosine Receptors and their Ligands," Naunyn-Schmiedeberg's Arch. Pharmacol., 2000, 362: 382-391.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Olah, et al.:"Cloning, Expression, and Characterization of the Unique Bovine A1 Adenosine Receptor," Journal of Biological Chemistry, May 25, 1992, 267(15):10764-10770.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Poulsen, et al.:"Adenosine Receptors: New Opportunities for Future Drugs," Bioorganic & Medicinal Chemistry, Jan. 8, 1998, 6(6): 619-641.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

Quintela, et al.:"Synthesis, Antihistaminic and Cytotoxic Activity of Pyridothieno- and Pyridodithienotriazines", Eur. J. Med. Chem, 1998, 33:887-897.

Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.

Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.

Ruhe, et al.:"Use of Antioxidant Nutrients in the Prevention and Treatment of Type 2 Diabetes," Journal of the American College of Nutrition, 2001, 20(5): 363S-369S.

Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

Sheridan:"The Most Common Chemical Replacements in Drug-Like Compounds," J Chem. Inf. Comput. Sci., 2002, 42:103-108.

Suttner, et al.:"The Heart in the Elderly Critically Ill Patient," Curr. Opin. Crit. Care, Oct. 2002, 8(5):389-94, abstract retrieved from MEDLINE Accession No. 2002495386, PubMed ID: 12357105.

Szydlowski, et al.:"Biological Role of Chromium," Diabetologia Polska, 2003, 10(3):365-370, English language abstract retrieved from EMBASE Accession No. 2004016455.

Vasudevan A. et al., "Aminopiperidine indazoles as orally efficacious melanin concentrating hormone receptoer-1 antagonists," Bioorg. Med. Chem. Lett. 2005, 15 (23), 5293-5297.

Vippagunta, et al.:"Crystalline Solids," Advanced Drug Delivery Reviews, May 16, 2001, 48(1):3-26.

West:"Solid State Chemistry and its Applications," Wiley, New York, 1988, pp. 358 & 365.

Ye, et al.:Organic Synthesis with α-Diazocarbonyl Compounds, Chem. Rev. 1994, 94:1091-1160.

Yu, et al:"Physical Characterization of Polymorphic Drugs: An Integrated Characterization Strategy," Pharmaceutical Science & Technology Today, Jun. 1998, 1(3):118-127.

Zhu, G. et al., "Design and synthesis of pyridine-pyrazolopyridine-based inhibitors of protein kinase B/Akt," Bioorg. Med. Chem. 2007, 15 (6), 2441-2452.

Elzein, et al.:"A1 Adenosine Receptor Agonists and their Potential Theraputic Applications," Expert Opin. Investig. Drugs, 2008, 17(12):1901-1910.

U.S. Appl. No. 13/210,889, filed Aug. 16, 2011.

* cited by examiner

HETEROARYL-SUBSTITUTED DICYANOPYRIDINES AND THEIR USE

This application is the National Stage of International Patent Application Number PCT/EP2009/001352, filed Jan. 26, 2009, which claims the benefit of German Application Number DE 10 2008 013 587.9, filed Feb. 11, 2008.

The present application relates to novel heteroaryl-substituted dicyanopyridines, to processes for their preparation, to their use for the treatment and/or prophylaxis of diseases and to their use for preparing medicaments for the treatment and/or prophylaxis of diseases, preferably for the treatment and/or prevention of cardiovascular disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation.

The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations. The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists. In humans, the inhibition of A1 receptors by specific A1 antagonists has a uricosuric, natriuretic and potassium-sparing diuretic effect without affecting the glomerular filtration rate, thus being renoprotective. Accordingly, selective A1 antagonists can be suitable inter alia for treating acute heart failure and chronic heart failure. Furthermore, they can be used for renoprotection in cases of nephropathy and other renal disorders.

In adipocytes, the activation of A1 receptors leads to an inhibition of lipolysis. Thus, the action of A1 agonists on lipid metabolism results in a lowering of free fatty acids and triglycerides. In turn, in patients suffering from metabolic syndrome and in diabetics, reducing lipids leads to lower insulin resistance and improved symptoms. The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference). The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference).

The "adenosine-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of these adenosine ligands known from the prior art have the disadvantage that their action is not really receptor-specific, that their activity is less than that of natural adenosine or that they have only very weak activity after oral administration. Thus, they are mainly used only for experimental purposes. Compounds of this type which are still in clinical development are hitherto only suitable for intravenous administration.

WO 01/25210, WO 02/070484, WO 02/070485, WO 2008028590, WO 2008064788 and WO 2008/064789 disclose substituted 2-thio- and 2-oxy-3,5-dicyano-4-phenyl-6-aminopyridines as adenosine receptor ligands for the treatment of cardiovascular disorders. WO 03/053441 describes specific substituted 2-thio-3,5-dicyano-4-phenyl-6-aminopyridines as selective ligands of the adenosine A1 receptor for the treatment of cardiovascular disorders. However, it has been found that these compounds have disadvantages with respect to their physicochemical properties such as, for example, their solubility and/or formulatability, and/or with respect to their in vivo properties, such as, for example, their pharmacokinetic behavior, their dose-activity relationship and/or their metabolic path.

The databank Chemical Abstracts lists various 4-thienyl-3,5-dicyanopyridines, without any details on preparation and use.

Substituted 2-amino-3,5-dicyanopyridines for treating prion infections are described in *J. Med. Chem.* 2007, 50, 65-73. JP 09-132529 describes aminopyridines as NO-synthase inhibitors. JP 10-324687 claims substituted pyrroles as fungicides. Furthermore, WO 01/62233 discloses various pyridine and pyrimidine derivatives and their use as adenosine receptor modulators. Substituted 3,5-dicyanopyridines as calcium-dependent potassium channel openers for the treatment of urological disorders are claimed in EP 1 302 463-A1 and JP 2003-183254. WO 03/091246 describes pyrrole-substituted pyridines and pyrimidines as kinase inhibitors for the treatment of, for example, cancer.

It is an object of the present invention to provide novel compounds which act as potent and selective ligands of the adenosine A1 receptor and as such are suitable for the treatment and/or prevention of diseases, in particular for the treatment and/or prevention of cardiovascular disorders and have an identical or improved physicochemical, pharmacokinetic and/or therapeutic profile compared to the compounds known from the prior art.

The present invention provides compounds of the formula (I)

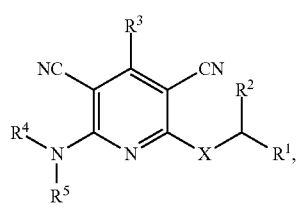

in which

X represents O or S, $R^1$ represents phenyl or 5- or 6-membered heteroaryl, where phenyl and 5- or 6-membered heteroaryl are substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxy-carbonyl, aminocarbonyl, mono-$(C_1-C_6)$-alkylaminocarbonyl, di-$(C_1-C_6)$-alkylamino-carbonyl, $(C_3-C_7)$-cycloalkylaminocarbonyl, aminosulfonyl, mono-$(C_1-C_6)$-alkylamino-sulfonyl, di-$(C_1-C_6)$-alkylaminosulfonyl, $(C_1-C_6)$-alkylsulfonylamino, pyrrolidino, piperidino, morpholino, piperazino, N'—$(C_1-C_4)$-alkylpiperazino, pyrrolidinocarbonyl, piperidinocarbonyl, morpholinocarbonyl, piperazinocarbonyl, N'—$(C_1-C_4)$-alkylpiperazinocarbonyl, phenyl and 5- or 6-membered heteroaryl, where phenyl and 5- or 6-membered heteroaryl may be substituted by 1 to 3 substituents independently of one another selected from the group consisting of halogen, nitro, cyano, $(C_1-C_6)$-alkyl, difluoromethoxy, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl, $R^2$ represents hydrogen or $(C_1-C_4)$-alkyl, $R^3$ represents thienyl, pyrrolyl, oxazolyl, thiazolyl, isoxazolyl, isothiazolyl, pyrazolyl, imidazolyl, triazolyl, oxadiazolyl, thiadiazolyl or tetrazolyl, where thienyl, pyrrolyl, oxazolyl, thiazolyl, isoxazolyl, isothiazolyl, pyrazolyl, imidazolyl, triazolyl, oxadiazolyl, thiadiazolyl and tetrazolyl may be substituted by 1 or 2 substituents independently of one another selected from the group consisting of halogen, cyano, hydroxyl, $(C_1-C_6)$-alkyl, $(C_1-C_6)$-alkoxy, $(C_3-C_7)$-cycloalkoxy and —$NR^AR^B$, where $(C_1-C_6)$-alkyl and $(C_1-C_6)$-alkoxy may be substituted by 1 to 3 substituents independently of one another selected from the group consisting of fluorine, trifluoromethyl, $(C_3-C_7)$-cycloalkyl, oxo, hydroxyl, $(C_1-C_4)$-alkoxy, hydroxycarbonyl, amino, mono-$(C_1-C_4)$-alkylamino and di-$(C_1-C_4)$-alkylamino, and where $(C_3-C_7)$-cycloalkoxy may be substituted by 1 or 2 substituents independently of one another selected from the group consisting of $(C_1-C_4)$-alkyl, hydroxyl, oxo and $(C_1-C_4)$-alkoxy, and where $R^A$ represents hydrogen or $(C_1-C_6)$-alkyl, where $(C_1-C_6)$-alkyl for its part may be substituted by 1 to 3 fluorine substituents, and where $(C_1-C_6)$-alkyl for its part may be substituted by a substituent selected from the group consisting of hydroxyl and $(C_1-C_4)$-alkoxy, $R^B$ represents hydrogen, $(C_1-C_6)$-alkyl, $(C_3-C_7)$-cycloalkyl, $(C_1-C_6)$-alkylcarbonyl, $(C_1-C_4)$-alkylsulfonyl or $(C_3-C_7)$-cycloalkylsulfonyl, where $(C_1-C_6)$-alkyl for its part may be substituted by 1 to 3 fluorine substituents, and where $(C_1-C_6)$-alkyl for its part may be substituted by 1 or 2 substituents independently of one another selected from the group consisting of $(C_3-C_7)$-cycloalkyl, oxo, hydroxyl, $(C_1-C_4)$-alkoxy, hydroxycarbonyl, amino, mono-$(C_1-C_4)$-alkylamino, di-$(C_1-C_4)$-alkylamino and $(C_3-C_7)$-cycloalkylamino, and where $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy, or $R^A$ and $R^B$ together with the nitrogen atom to which they are attached form a 4- to 7-membered heterocycle which may contain a further ring heteroatom from the group consisting of N, O and S and may be substituted by 1 or 2 substituents independently of one another selected from the group consisting of $(C_1-C_4)$-alkyl, hydroxyl, oxo and $(C_1-C_4)$-alkoxy, $R^4$ represents hydrogen or $(C_1-C_6)$-alkyl, where $(C_1-C_6)$-alkyl may be substituted by 1 or 2 substituents independently of one another selected from the group consisting of hydroxyl, $(C_1-C_4)$-alkoxy, hydroxycarbonyl, $(C_1-C_4)$-alkoxycarbonyl, amino, mono-$(C_1-C_4)$-alkylamino and di-$(C_1-C_4)$-alkylamino, $R^5$ represents hydrogen or $(C_1-C_6)$-alkyl, where $(C_1-C_6)$-alkyl may be substituted by 1 or 2 substituents independently of one another selected from the group consisting of hydroxyl, $(C_1-C_4)$-alkoxy, hydroxycarbonyl, $(C_1-C_4)$-alkoxycarbonyl, amino, mono-$(C_1-C_4)$-alkylamino and di-$(C_1-C_4)$-alkylamino, or $R^4$ and $R^5$ together with the nitrogen atom to which they are attached form a 4- to 7-membered heterocycle which may contain a further ring heteroatom from the group consisting of N, O and S and may be substituted by 1 or 2 substituents independently of one another selected from the group consisting of $(C_1-C_4)$-alkyl, hydroxyl, oxo and $(C_1-C_4)$-alkoxy, and N-oxides, salts, solvates, salts of the N-oxides and solvates of the N-oxides and salts thereof, except for the compounds 2-amino-6-[[(3-methylphenyl)methyl]thio]-4-(2-thienyl)-3,5-pyridinedicarbonitrile, 2-amino-6-[[(2-chlorophenyl)methyl]thio]-4-(2-thienyl)-3,5-pyridinedi-carbonitrile, 2-amino-6-[[(2-methylphenyl)methyl]thio]-4-(2-thienyl)-3,5-pyridinedicarbonitrile, 2-amino-6-[[(3-chlorophenyl)methyl]thio]-4-(2-thienyl)-3,5-pyridinedicarbonitrile, 2-amino-6-[[(4-chlorophenyl)methyl]thio]-4-(2-thienyl)-3,5-pyridinedicarbonitrile, 2-amino-6-[[(3-fluorophenyl)-methyl]thio]-4-(2-thienyl)-3,5-pyridinedicarbonitrile, 2-amino-6-[[(4-methylphenyl)methyl]thio]-4-(2-thienyl)-3,5-pyridinedicarbonitrile, 2-amino-6-[[(2-bromophenyl)methyl]thio]-4-(2-thienyl)-3,5-pyridinedicarbonitrile, 2-amino-6-[[(3-bromophenyl)methyl]thio]-4-(2-thienyl)-3,5-pyridinedicarbonitrile, 2-amino-6-[[(4-bromophenyl)methyl]thio]-4-(2-thienyl)-3,5-pyridinedicarbonitrile, 2-amino-4-(2-thienyl)-6-[[[3-(trifluoromethyl)phenyl]methyl]thio]-3,5-pyridinedicarbonitrile, 2-amino-6-[[(3-methoxyphenyl)methyl]thio]-4-(2-thienyl)-3,5-pyridinedicarbonitrile, 2-amino-4-(2-thienyl)-6-[[[2-(trifluoromethyl)phenyl]methyl]thio]-3,5-pyridinedicarbonitrile, 2-amino-6-[[[4-(1,1-dimethylethyl)phenyl]methyl]thio]-4-(2-thienyl)-3,5-pyridinedicarbonitrile, 2-amino-6-[[(4-fluorophenyl)methyl]thio]-4-(2-thienyl)-3,5-pyridinedicarbonitrile, 2-amino-6-[[(2-fluorophenyl)-methyl]thio]-4-(2-thienyl)-3,5-pyridinedicarbonitrile, 2-amino-6-[[(2-chloro-6-fluorophenyl)methyl]thio]-4-(2-thienyl)-3,5-pyridinedicarbonitrile, 2-amino-6-[[(2,6-dichlorophenyl)methyl]thio]-4-(2-thienyl)-3,5-pyridinedicarbonitrile.

Compounds according to the invention are the compounds of the formula (I) and the N-oxides, salts, solvates, salts of the N-oxides and solvates of the salts and N-oxides thereof, the compounds which are encompassed by the formula (I) of the formulae mentioned below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

Alkyl is in the context of the invention a straight-chain or branched alkyl radical having 1 to 6 or 1 to 4 carbon atoms. A straight-chain or branched alkyl adical having 1 to 4 carbon atoms is preferred. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

Cycloalkyl is in the context of the invention a monocyclic saturated carbocycle having 3 to 7 or 5 or 6 ring carbon atoms. The following radicals may be mentioned by way of example and by way of preference: cyclopropyl, cyclobutyl, cyclopentyl, cyclohexyl and cycloheptyl.

Alkylcarbonyl is in the context of the invention a straight-chain or branched alkyl radical having 1 to 6 or 1 to 4 carbon atoms and a carbonyl group attached in position 1. The following radicals may be mentioned by way of example and by way of preference: methylcarbonyl, ethylcarbonyl, n-propylcarbonyl, isopropylcarbonyl, n-butylcarbonyl, isobutylcarbonyl and tert-butylcarbonyl.

Alkoxy is in the context of the invention a straight-chain or branched alkoxy radical having 1 to 6 or 1 to 4 or 2 to 4 carbon atoms. A straight-chain or branched alkoxy-radical having 1 to 4 or 2 to 4 carbon atoms is preferred. The following radicals may be mentioned by way of example and by way of preference: methoxy, ethoxy, n-propoxy, isopropoxy, n-butoxy, tert-butoxy, n-pentoxy and n-hexoxy.

Cycloalkoxy is in the context of the invention a monocyclic saturated carbocycle having 3 to 7 carbon atoms which is attached via an oxygen atom. The following radicals may be mentioned by way of example and by way of preference: cyclopropyloxy, cyclobutyloxy, cyclopentyloxy, cyclohexyloxy and cycloheptyloxy. Alkoxycarbonyl is in the context of the invention a straight-chain or branched alkoxy radical having 1 to 6 or 1 to 4 carbon atoms and a carbonyl group attached at the oxygen. A straight-chain or branched alkoxycarbonyl radical having 1 to 4 carbon atoms in the alkoxy group is preferred. The following radicals may be mentioned by way of example and by way of preference: methoxycarbonyl, ethoxycarbonyl, n-propoxycarbonyl, isopropoxycarbonyl and tert-butoxycarbonyl.

Monoalkylamino is in the context of the invention an amino group having a straight-chain or branched alkyl substituent having 1 to 6 or 1 to 4 or 2 to 4 carbon atoms. A straight-chain or branched monoalkylamino radical having 1 to 4 or 2 to 4 carbon atoms is preferred. The following radicals may be mentioned by way of example and by way of preference: methylamino, ethylamino, n-propylamino, isopropylamino, n-butylamino, tert-butylamino, n-pentylamino and n-hexylamino.

Dialkylamino is in the context of the invention an amino group having two identical or different straight-chain or branched alkyl substituents having 1 to 6 or 1 to 4 carbon atoms each. Straight-chain or branched dialkylamino radicals having 1 to 4 carbon atoms each are preferred. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-ethyl-N-n-pentylamino and N-n-hexyl-N-methylamino.

Cycloalkylamino is in the context of the invention an amino group having a monocyclic saturated carbocycle having 3 to 7 carbon atoms. The following radicals may be mentioned by way of example and by way of preference: cyclopropylamino, cyclobutylamino, cyclopentylamino, cyclohexylamino and cycloheptylamino. Monoalkylaminocarbonyl is in the context of the invention an amino group which is attached via a carbonyl group and has a straight-chain or branched alkyl substituent having 1 to 6 or 1 to 4 carbon atoms. A monoalkylaminocarbonyl radical having 1 to 4 carbon atoms in the alkyl group is preferred. The following radicals may be mentioned by way of example and by way of preference: methylaminocarbonyl, ethylaminocarbonyl, n-propylaminocarbonyl, isopropylaminocarbonyl, n-butylaminocarbonyl, tert-butylaminocarbonyl, n-pentylaminocarbonyl and n-hexylaminocarbonyl.

Dialkylaminocarbonyl is in the context of the invention an amino group which is attached via a carbonyl group and which has two identical or different straight-chain or branched alkyl substituents having 1 to 6 or 1 to 4 carbon atoms each. A dialkylaminocarbonyl radical having in each case 1 to 4 carbon atoms per alkyl group is preferred. The following radicals may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl, N-tert-butyl-N-methylaminocarbonyl, N-n-pentyl-N-methylaminocarbonyl and N-n-hexyl-N-methylaminocarbonyl.

Cycloalkylaminocarbonyl is in the context of the invention an amino group which is attached via a carbonyl group and has a monocyclic saturated carbocycle having 3 to 7 carbon atoms. The following radicals may be mentioned by way of example and by way of preference: cyclopropylaminocarbonyl, cyclobutylaminocarbonyl, cyclopentylaminocarbonyl, cyclohexylaminocarbonyl and cycloheptylaminocarbonyl.

Monoalkylaminosulfonyl is in the context of the invention an amino group which is attached via a sulfonyl group and which has a straight-chain or branched alkyl substituents having 1 to 6 carbon atoms. The following radicals may be mentioned by way of example and by way of preference: methylaminosulfonyl, ethylamino-sulfonyl, n-propylaminosulfonyl, isopropylaminosulfonyl, n-butylaminosulfonyl and tert-butylaminosulfonyl.

Dialkylaminosulfonyl is in the context of the invention an amino group which is attached via a sulfonyl group and which has two identical or different straight-chain or branched alkyl substituents having 1 to 6 carbon atoms each. The following radicals may be mentioned by way of example and by way of preference: N,N-dimethylaminosulfonyl, N,N-diethylaminosulfonyl, N-ethyl-N-methylaminosulfonyl, N-methyl-N-n-propylaminosulfonyl, N-n-butyl-N-methylaminosulfonyl and N-tert-butyl-N-methylaminosulfonyl.

Alkylsulfonyl is in the context of the invention a straight-chain or branched alkyl radical which has 1 to 4 carbon atoms and is attached via a sulfonyl group. The following radicals may be mentioned by way of example and by way of preference: methylsulfonyl, ethylsulfonyl, n-propylsulfonyl, isopropylsulfonyl, n-butylsulfonyl and tert-butylsulfonyl.

Cycloalkylsulfonyl is in the context of the invention a monocyclic saturated alkyl radical which has 3 to 7 carbon atoms and is attached via a sulfonyl group. The following radicals may be mentioned by way of example and by way of preference: cyclopropylsulfonyl, cyclobutylsulfonyl, cyclopentylsulfonyl, cyclohexylsulfonyl and cycloheptylsulfonyl.

Alkylsulfonylamino is in the context of the invention an amino group having a straight-chain or branched alkylsulfonyl substituent which has 1 to 6 carbon atoms and which is attached via the sulfonyl group to the nitrogen atom. The following radicals may be mentioned by way of example and by way of preference: methyl-sulfonylamino, ethylsulfonylamino, n-propylsulfonylamino, isopropylsulfonylamino, n-butylsulfonylamino, tert-butylsulfonylamino, n-pentylsulfonylamino and n-hexylsulfonylamino.

Heterocyclyl is in the context of the invention a saturated heterocycle having a total of 4 to 7 ring atoms which contains one or two ring heteroatoms from the group consisting of N, O and S and is attached via a ring carbon atom or, if appropriate, via a ring nitrogen atom. The following radicals may be mentioned by way of example: azetidinyl, pyrrolidinyl, pyrazolidinyl, tetrahydrofuranyl, piperidinyl, piperazinyl, tetrahydropyranyl, morpholinyl and thiomorpholinyl. Azetidinyl, pyrrolidinyl, tetrahydrofuranyl, piperidinyl, piperazinyl, tetrahydropyranyl and morpholinyl are preferred.

Heteroaryl is in the context of the invention a monocyclic aromatic heterocycle (heteroaromatic) which has a total of 5 or 6 ring atoms, contains up to three identical or different ring heteroatoms from the group consisting of N, O and S and is attached via a ring carbon atom or, if appropriate, via a ring nitrogen atom. The following radicals may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl.

Halogen includes in the context of the invention fluorine, chlorine, bromine and iodine. Preference is given to chlorine or fluorine.

An oxo group is in the context of the invention an oxygen atom which is attached via a double bond to a carbon atom.

In the formulae of the group possible for $R^3$, the end point of the line where there is a sign * does not represent a carbon atom or a CH$_2$ group but forms part of the bond to the atom which is designated in each case and to which R$^3$ is attached.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

In the context of the present invention, preference is given to compounds of the formula (I) in which X represents O or S, R$^1$ represents phenyl or 5- or 6-membered heteroaryl,
    where phenyl and 5- or 6-membered heteroaryl are substituted by 1 or 2 substituents independently of one another selected from the group consisting of fluorine, chlorine, cyano, (C$_1$-C$_4$)-alkyl, trifluoromethyl, (C$_1$-C$_4$)-alkoxy, mono-(C$_1$-C$_4$)-alkylamino, di-(C$_1$-C$_4$)-alkylamino, hydroxycarbonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, pyrrolidino, piperidino, morpholino, piperazino, N'—(C$_1$-C$_4$)-alkylpiperazino, phenyl and 5- or 6-membered heteroaryl,
where phenyl and 5- or 6-membered heteroaryl may be substituted by 1 or 2 substituents independently of one another selected from the group consisting of fluorine, chlorine, cyano, (C$_1$-C$_4$)-alkyl, difluoromethyl, trifluoromethyl, (C$_1$-C$_4$)-alkoxy, difluoromethoxy, trifluoromethoxy, hydroxycarbonyl and (C$_1$-C$_4$)-alkoxycarbonyl, R$^2$ represents hydrogen or methyl, R$^3$ represents pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-5-yl, pyrazol-1-yl, pyrazol-3-yl, pyrazol-4-yl, pyrazol-5-yl, imidazol-1-yl, imidazol-2-yl, imidazol-4-yl or imidazol-5-yl,
    where pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-5-yl, pyrazol-1-yl, pyrazol-3-yl, pyrazol-4-yl, pyrazol-5-yl, imidazol-1-yl, imidazol-2-yl, imidazol-4-yl and imidazol-5-yl may be substituted by 1 or 2 substituents independently of one another selected from the group consisting of fluorine, (C$_1$-C$_6$)-alkyl, (C$_1$-C$_4$)-alkoxy and —NR$^A$R$^B$,
    where (C$_1$-C$_6$)-alkyl and (C$_1$-C$_4$)-alkoxy may be substituted by 1 to 3 fluorine substituents,
    and
    where (C$_1$-C$_6$)-alkyl and (C$_2$-C$_4$)-alkoxy may be substituted by 1 or 2 substituents independently of one another selected from the group consisting of trifluoromethyl, hydroxyl, methoxy, ethoxy, hydroxycarbonyl, amino, methylamino, ethylamino, N,N-dimethylamino and N,N-diethylamino,
    and
    where
        R$^A$ represents hydrogen or (C$_1$-C$_4$)-alkyl,
        where (C$_1$-C$_4$)-alkyl for its part may be substituted by a substituent selected from the group consisting of hydroxyl and (C$_1$-C$_4$)-alkoxy,
        R$^B$ represents hydrogen or (C$_1$-C$_4$)-alkyl,
        where (C$_1$-C$_4$)-alkyl for its part may be substituted by 1 or 2 substituents independently of one another selected from the group consisting of hydroxyl, (C$_1$-C$_4$)-alkoxy and hydroxycarbonyl,
    R$^4$ represents hydrogen or methyl,
    R$^5$ represents hydrogen or (C$_1$-C$_4$)-alkyl,
        where (C$_1$-C$_4$)-alkyl may be substituted by 1 or 2 substituents independently of one another selected from the group consisting of hydroxyl, methoxy and ethoxy,
    or
    R$^4$ and R$^5$ together with the nitrogen atom to which they are attached form a 4- to 6-membered heterocycle which may contain a further ring heteroatom from the group consisting of N, O and S and may be substituted by 1 or 2 substituents independently of one another selected from the group consisting of (C$_1$-C$_4$)-alkyl, hydroxyl, methoxy and ethoxy,
    and salts, solvates and solvates of the salts thereof.

In the context of the present invention, preference is also given to compounds of the formula (I) in which X represents O or S, R$^1$ represents phenyl or 5- or 6-membered heteroaryl,
    where phenyl and 5- or 6-membered heteroaryl are substituted by 1 or 2 substituents independently of one another selected from the group consisting of fluorine, chlorine, cyano, (C$_1$-C$_4$)-alkyl, trifluoromethyl, (C$_1$-C$_4$)-alkoxy, mono-(C$_1$-C$_4$)-alkylamino, di-(C$_1$-C$_4$)-alkylamino, hydroxycarbonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, pyrrolidino, piperidino, morpholino, piperazino, N'—(C$_1$-C$_4$)-alkylpiperazino, phenyl and 5- or 6-membered heteroaryl,
where phenyl and 5- or 6-membered heteroaryl may be substituted by 1 or 2 substituents independently of one another selected from the group consisting of fluorine, chlorine, cyano, (C$_1$-C$_4$)-alkyl, difluoromethyl, trifluoromethyl, (C$_1$-C$_4$)-alkoxy, difluoromethoxy, trifluoromethoxy, hydroxycarbonyl and (C$_1$-C$_4$)-alkoxycarbonyl, R$^2$ represents hydrogen or methyl, R$^3$ represents pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-5-yl, pyrazol-1-yl, pyrazol-3-yl, pyrazol-4-yl, pyrazol-5-yl, imidazol-1-yl, imidazol-2-yl, imidazol-4-yl or imidazol-5-yl,
    where pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-5-yl, pyrazol-1-yl, pyrazol-3-yl, pyrazol-4-yl, pyrazol-5-yl, imidazol-1-yl, imidazol-2-yl, imidazol-4-yl and imidazol-5-yl may be substituted by 1 or 2 substituents independently of one another selected from the group consisting of fluorine, trifluoromethyl (C$_1$-C$_6$)-alkyl, (C$_1$-C$_4$)-alkoxy and —NR$^A$R$^B$,
    where (C$_1$-C$_6$)-alkyl and (C$_2$-C$_4$)-alkoxy may be substituted by 1 or 2 substituents independently of one another selected from the group consisting of fluorine, trifluoromethyl, hydroxyl, methoxy, ethoxy, hydroxycarbonyl, amino, methylamino, ethylamino, N,N-dimethylamino and N,N-diethylamino,
    and
    where
        R$^A$ represents hydrogen or (C$_1$-C$_4$)-alkyl,
        where (C$_1$-C$_4$)-alkyl for its part may be substituted by a substituent selected from the group consisting of hydroxyl and (C$_1$-C$_4$)-alkoxy,
        R$^B$ represents hydrogen or (C$_1$-C$_4$)-alkyl,
        where (C$_1$-C$_4$)-alkyl for its part may be substituted by 1 or 2 substituents independently of one another selected from the group consisting of hydroxyl, (C$_1$-C$_4$)-alkoxy and hydroxycarbonyl,
    R$^4$ represents hydrogen or methyl,
    R$^5$ represents hydrogen or (C$_1$-C$_4$)-alkyl, where ($C_1$-$C_4$)-alkyl may be substituted by 1 or 2 substituents independently of one another selected from the group consisting of hydroxyl, methoxy and ethoxy,
or
$R^4$ and $R^5$ together with the nitrogen atom to which they are attached form a 4- to 6-membered heterocycle which may contain a further ring heteroatom from the group consisting of N, O and S and may be substituted by 1 or 2 substituents independently of one another selected from the group consisting of ($C_1$-$C_4$)-alkyl, hydroxyl, methoxy and ethoxy,
and salts, solvates and solvates of the salts thereof.

In the context of the present invention, particular preference is given to compounds of the formula (I) in which
X represents S,
$R^1$ represents phenyl, oxazolyl, thiazolyl or pyridyl,
where phenyl and pyridyl are substituted by a substituent selected from the group consisting of cyano, methoxy, ethoxy, hydroxycarbonyl, methoxycarbonyl, ethoxycarbonyl, aminocarbonyl, methylaminocarbonyl and dimethylaminocarbonyl,
and
where phenyl and pyridyl may by substituted by a substituent selected from the group consisting of fluorine, chlorine, methyl, ethyl and trifluoromethyl,
and
where oxazolyl and thiazolyl are substituted by a phenyl substituent,
where phenyl may by substituted by a substituent selected from the group consisting of fluorine, chlorine, cyano, methyl, methoxy, hydroxycarbonyl and methoxycarbonyl,
and
where oxazolyl and thiazolyl may by substituted by a substituent selected from the group consisting of fluorine, methyl, ethyl, methoxy, hydroxycarbonyl and methoxycarbonyl,
$R^2$ represents hydrogen,
$R^3$ represents a group of the formula

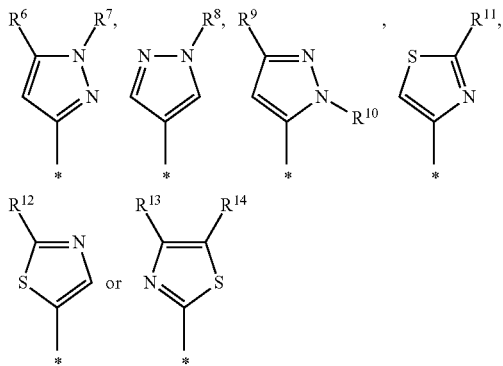

where
* denotes the point of attachment to the pyridine,
and
where
$R^6$ represents hydrogen, methyl or ethyl,
$R^7$ represents hydrogen or ($C_1$-$C_6$)-alkyl,
where ($C_1$-$C_6$)-alkyl may be substituted by 1 or 2 substituents independently of one another selected from the group consisting of hydroxyl and methoxy,
$R^8$ represents hydrogen or ($C_1$-$C_6$)-alkyl,
where ($C_1$-$C_6$)-alkyl may be substituted by 1 or 2 substituents independently of one another selected from the group consisting of hydroxyl and methoxy,
$R^9$ represents hydrogen, methyl or ethyl,
$R^{10}$ represents hydrogen,
$R^{11}$ represents hydrogen or ($C_1$-$C_6$)-alkyl,
where ($C_1$-$C_6$)-alkyl may be substituted by 1 or 2 substituents independently of one another selected from the group consisting of hydroxyl and methoxy,
$R^{12}$ represents hydrogen or ($C_1$-$C_6$)-alkyl,
where ($C_1$-$C_6$)-alkyl may be substituted by 1 or 2 substituents independently of one another selected from the group consisting of hydroxyl and methoxy,
$R^{13}$ represents hydrogen, methyl or ethyl,
and
$R^{14}$ represents hydrogen or ($C_1$-$C_6$)-alkyl,
where ($C_1$-$C_6$)-alkyl may be substituted by 1 or 2 substituents independently of one another selected from the group consisting of hydroxyl and methoxy,
$R^4$ represents hydrogen,
$R^5$ represents hydrogen, ethyl, n-propyl or sec-butyl,
where ethyl, n-propyl and sec-butyl may be substituted by 1 or 2 hydroxyl substituents,
or
$R^4$ and $R^5$ together with the nitrogen atom to which they are attached form an azetidinyl or pyrrolidinyl ring which may be substituted by a hydroxyl substituent, and salts, solvates and solvates of the salts thereof.

In the context of the present invention, preference is also given to compounds of the formula (I) in which
X represents O or S,
$R^1$ represents phenyl, oxazolyl, thiazolyl or pyridyl,
where phenyl is substituted by a substituent selected from the group consisting of cyano, hydroxycarbonyl, ($C_1$-$C_4$)-alkoxycarbonyl, aminocarbonyl, mono-($C_1$-$C_4$)-alkylaminocarbonyl and di-($C_1$-$C_4$)-alkylaminocarbonyl,
and
where phenyl may be substituted by a substituent independently of one another selected from the group consisting of fluorine, chlorine, ($C_1$-$C_4$)-alkyl, trifluoromethyl, ($C_1$-$C_4$)-alkoxy, phenyl and 5- or 6-membered heteroaryl,
where phenyl and 5- or 6-membered heteroaryl may be substituted by 1 or 2 substituents independently of one another selected from the group consisting of fluorine, chlorine, cyano, ($C_1$-$C_4$)-alkyl, difluoromethyl, trifluoromethyl, ($C_1$-$C_4$)-alkoxy, difluoromethoxy, trifluoromethoxy, hydroxycarbonyl and ($C_1$-$C_4$)-alkoxycarbonyl,
and
where oxazolyl, thiazolyl and pyridyl may be substituted by 1 or 2 substituents independently of one another from the group consisting of fluorine, chlorine, cyano, ($C_1$-$C_4$)-alkyl, trifluoromethyl, ($C_1$-$C_4$)-alkoxy, hydroxycarbonyl, ($C_1$-$C_4$)-alkoxy-carbonyl, aminocarbonyl, mono-($C_1$-$C_4$)-alkylaminocarbonyl, di-($C_1$-$C_4$)-alkylamino-carbonyl, pyrrolidino, piperidino, morpholino, piperazino, N'—($C_1$-$C_4$)-alkylpiperazino, phenyl and 5- or 6-membered heteroaryl,
where phenyl and 5- or 6-membered heteroaryl may be substituted by 1 or 2 substituents independently of one another selected from the group consisting of fluorine, chlorine, cyano, ($C_1$-$C_4$)-alkyl, difluoromethyl, trifluoromethyl, ($C_1$-$C_4$)-alkoxy, difluoromethoxy, trifluoromethoxy, hydroxycarbonyl and ($C_1$-$C_4$)-alkoxycarbonyl,
$R^2$ represents hydrogen or ($C_1$-$C_4$)-alkyl,
$R^3$ represents thien-2-yl or thien-3-yl,
where thien-2-yl and thien-3-yl may be substituted by 1 or 2 substituents independently of one another selected from the group consisting of fluorine, ($C_1$-$C_6$)-alkyl, ($C_1$-$C_4$)-alkoxy and —$NR^A R^B$, where ($C_1$-$C_6$)-alkyl and ($C_1$-$C_4$)-alkoxy may be substituted by 1 to 3 fluorine substituents,
and
where ($C_1$-$C_6$)-alkyl and ($C_2$-$C_4$)-alkoxy may be substituted by 1 or 2 substituents independently of one another selected from the group consisting of trifluoromethyl, hydroxyl, methoxy, ethoxy, hydroxycarbonyl, amino, mono-($C_1$-$C_4$)-alkylamino and di-($C_1$-$C_4$)-alkylamino,
and
where
$R^A$ represents hydrogen or ($C_1$-$C_4$)-alkyl,
where ($C_1$-$C_4$)-alkyl for its part may be substituted by a substituent selected from the group consisting of hydroxyl and ($C_1$-$C_4$)-alkoxy,
$R^B$ represents hydrogen or ($C_1$-$C_4$)-alkyl,
where ($C_1$-$C_4$)-alkyl for its part may be substituted by 1 or 2 substituents independently of one another selected from the group consisting of hydroxyl, ($C_1$-$C_4$)-alkoxy and hydroxycarbonyl,
$R^4$ represents hydrogen or methyl,
$R^5$ represents hydrogen or ($C_1$-$C_4$)-alkyl,
where ($C_1$-$C_4$)-alkyl may be substituted by 1 or 2 substituents independently of one another selected from the group consisting of hydroxyl, methoxy and ethoxy,
or
$R^4$ and $R^5$ together with the nitrogen atom to which they are attached form a 4- to 6-membered heterocycle which may contain a further ring heteroatom from the group consisting of N, O and S and may be substituted by 1 or 2 substituents independently of one another selected from the group consisting of ($C_1$-$C_4$)-alkyl, hydroxyl, methoxy and ethoxy,
and salts, solvates and solvates of the salts thereof.

In the context of the present invention, preference is also given to compounds of the formula (I) in which
X represents O or S,
$R^1$ represents phenyl, oxazolyl, thiazolyl or pyridyl,
where phenyl is substituted by a substituent selected from the group consisting of cyano, hydroxycarbonyl, ($C_1$-$C_4$)-alkoxycarbonyl, aminocarbonyl, mono-($C_1$-$C_4$)-alkylaminocarbonyl and di-($C_1$-$C_4$)-alkylaminocarbonyl,
and
where phenyl may be substituted by a substituent independently of one another selected from the group consisting of fluorine, chlorine, ($C_1$-$C_4$)-alkyl, trifluoromethyl, ($C_1$-$C_4$)-alkoxy, phenyl and 5- or 6-membered heteroaryl,
where phenyl and 5- or 6-membered heteroaryl may be substituted by 1 or 2 substituents independently of one another selected from the group consisting of fluorine, chlorine, cyano, ($C_1$-$C_4$)-alkyl, difluoromethyl, trifluoromethyl, ($C_1$-$C_4$)-alkoxy, difluoromethoxy, trifluoromethoxy, hydroxycarbonyl and ($C_1$-$C_4$)-alkoxycarbonyl,
and
where oxazolyl, thiazolyl and pyridyl are substituted by 1 or 2 substituents independently of one another selected from the group consisting of fluorine, chlorine, cyano, ($C_1$-$C_4$)-alkyl, trifluoromethyl, ($C_1$-$C_4$)-alkoxy, hydroxycarbonyl, ($C_1$-$C_4$)-alkoxy-carbonyl, aminocarbonyl, mono-($C_1$-$C_4$)-alkylaminocarbonyl, di-($C_1$-$C_4$)-alkylamino-carbonyl, pyrrolidino, piperidino, morpholino, piperazino, N'—($C_1$-$C_4$)-alkylpiperazino, phenyl and 5- or 6-membered heteroaryl,
where phenyl and 5- or 6-membered heteroaryl may be substituted by 1 or 2 substituents independently of one another selected from the group consisting of fluorine, chlorine, cyano, ($C_1$-$C_4$)-alkyl, difluoromethyl, trifluoromethyl, ($C_1$-$C_4$)-alkoxy, difluoromethoxy, trifluoromethoxy, hydroxycarbonyl and ($C_1$-$C_4$)-alkoxycarbonyl,
$R^2$ represents hydrogen or ($C_1$-$C_4$)-alkyl,
$R^3$ represents thien-2-yl or thien-3-yl,
where thien-2-yl and thien-3-yl may be substituted by 1 or 2 substituents independently of one another selected from the group consisting of fluorine, ($C_1$-$C_6$)-alkyl, ($C_1$-$C_4$)-alkoxy and —NR$^A$R$^B$,
where ($C_1$-$C_6$)-alkyl and ($C_2$-$C_4$)-alkoxy may be substituted by 1 or 2 substituents independently of one another selected from the group consisting of fluorine, trifluoromethyl, hydroxyl, methoxy, ethoxy, hydroxycarbonyl, amino, methylamino, ethylamino, N,N-dimethylamino and N,N-diethylamino,
and
where
$R^A$ represents hydrogen or ($C_1$-$C_4$)-alkyl,
where ($C_1$-$C_4$)-alkyl for its part may be substituted by a substituent selected from the group consisting of hydroxyl and ($C_1$-$C_4$)-alkoxy,
$R^B$ represents hydrogen or ($C_1$-$C_4$)-alkyl,
where ($C_1$-$C_4$)-alkyl for its part may be substituted by 1 or 2 substituents independently of one another selected from the group consisting of hydroxyl, ($C_1$-$C_4$)-alkoxy and hydroxycarbonyl,
$R^4$ represents hydrogen or methyl,
$R^5$ represents hydrogen or ($C_1$-$C_4$)-alkyl,
where ($C_1$-$C_4$)-alkyl may be substituted by 1 or 2 substituents independently of one another selected from the group consisting of hydroxyl, methoxy and ethoxy,
or
$R^4$ and $R^5$ together with the nitrogen atom to which they are attached form a 4- to 6-membered heterocycle which may contain a further ring heteroatom from the group consisting of N, O and S and may be substituted by 1 or 2 substituents independently of one another selected from the group consisting of ($C_1$-$C_4$)-alkyl, hydroxyl, methoxy and ethoxy,
and salts, solvates and solvates of the salts thereof.

In the context of the present invention, particular preference is also given to compounds of the formula (I) in which
X represents S,
$R^1$ represents phenyl, oxazolyl, thiazolyl or pyridyl,
where phenyl is substituted by a substituent selected from the group consisting of cyano, hydroxycarbonyl, methoxycarbonyl, ethoxycarbonyl, aminocarbonyl, methylaminocarbonyl and dimethylaminocarbonyl,
and
where pyridyl is substituted by a substituent selected from the group consisting of cyano, methoxy, ethoxy, hydroxycarbonyl, methoxycarbonyl, ethoxycarbonyl, aminocarbonyl, methylaminocarbonyl and dimethylaminocarbonyl,
and
where phenyl and pyridyl may be substituted by a substituent selected from the group consisting of fluorine, chlorine, methyl, ethyl and trifluoromethyl,
and
where oxazolyl and thiazolyl are substituted by a phenyl substituent,
where phenyl may be substituted by a substituent selected from the group consisting of fluorine, chlorine, cyano, methyl, methoxy, hydroxycarbonyl and methoxycarbonyl,
and
where oxazolyl and thiazolyl may be substituted by a substituent selected from the group consisting of fluorine, methyl, ethyl, methoxy, hydroxycarbonyl and methoxycarbonyl, $R^2$ represents hydrogen, $R^3$ represents a group of the formula

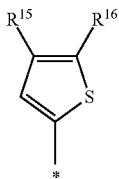

where

* denotes the point of attachment to the pyridine, and where $R^{15}$ represents hydrogen, methyl or ethyl, $R^{16}$ represents hydrogen or $(C_1-C_4)$-alkyl, where $(C_1-C_4)$-alkyl may be substituted by 1 or 2 substituents independently of one another selected from the group consisting of hydroxyl and methoxy, $R^4$ represents hydrogen, $R^5$ represents hydrogen, ethyl, n-propyl or sec-butyl, where ethyl, n-propyl and sec-butyl may be substituted by 1 or 2 hydroxyl substituents, or $R^4$ and $R^5$ together with the nitrogen atom to which they are attached form an azetidinyl or pyrrolidinyl ring which may be substituted by a hydroxyl substituent, and salts, solvates and solvates of the salts thereof.

In the context of the present invention, preference is also given to compounds of the formula (I) in which $R^1$ represents phenyl, oxazolyl, thiazolyl or pyridyl, where phenyl is substituted by a substituent selected from the group consisting of cyano, hydroxycarbonyl, methoxycarbonyl, ethoxycarbonyl, aminocarbonyl, methylaminocarbonyl and dimethylaminocarbonyl, and where pyridyl is substituted by a substituent selected from the group consisting of cyano, methoxy, ethoxy, hydroxycarbonyl, methoxycarbonyl, ethoxycarbonyl, aminocarbonyl, methylaminocarbonyl and dimethylaminocarbonyl, and where phenyl and pyridyl may be substituted by a substituent selected from the group consisting of fluorine, chlorine, methyl, ethyl and trifluoromethyl, and where oxazolyl and thiazolyl are substituted by a phenyl substituent, where phenyl may be substituted by a substituent selected from the group consisting of fluorine, chlorine, cyano, methyl, methoxy, hydroxycarbonyl and methoxycarbonyl, and where oxazolyl and thiazolyl may be substituted by a substituent selected from the group consisting of fluorine, methyl, ethyl, methoxy, hydroxycarbonyl and methoxycarbonyl, and salts, solvates and solvates of the salts thereof.

In the context of the present invention, preference is also given to compounds of the formula (I) in which $R^3$ represents a group of the formula

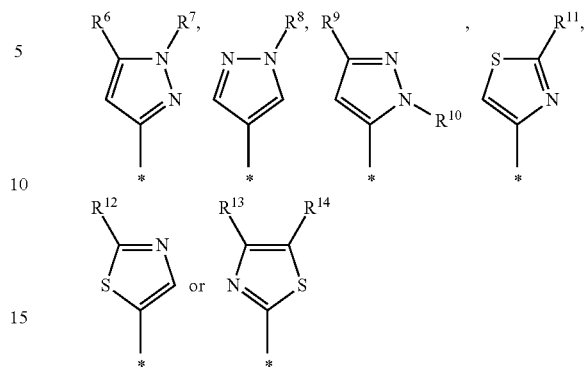

where

* denotes the point of attachment to the pyridine, and where $R^6$ represents hydrogen, methyl or ethyl, $R^7$ represents hydrogen or $(C_1-C_6)$-alkyl, where $(C_1-C_6)$-alkyl may be substituted by 1 or 2 substituents independently of one another selected from the group consisting of hydroxyl and methoxy, $R^8$ represents hydrogen or $(C_1-C_6)$-alkyl, where $(C_1-C_6)$-alkyl may be substituted by 1 or 2 substituents independently of one another selected from the group consisting of hydroxyl and methoxy, $R^9$ represents hydrogen, methyl or ethyl, $R^{10}$ represents hydrogen, $R^{11}$ represents hydrogen or $(C_1-C_6)$-alkyl, where $(C_1-C_6)$-alkyl may be substituted by 1 or 2 substituents independently of one another selected from the group consisting of hydroxyl and methoxy, $R^{12}$ represents hydrogen or $(C_1-C_6)$-alkyl, where $(C_1-C_6)$-alkyl may be substituted by 1 or 2 substituents independently of one another selected from the group consisting of hydroxyl and methoxy, $R^{13}$ represents hydrogen, methyl or ethyl, and $R^{14}$ represents hydrogen or $(C_1-C_6)$-alkyl, where $(C_1-C_6)$-alkyl may be substituted by 1 or 2 substituents independently of one another selected from the group consisting of hydroxyl and methoxy, and salts, solvates and solvates of the salts thereof.

The present invention furthermore provides the compounds 2-amino-6-[[(3-methylphenyl)methyl]thio]-4-(2-thienyl)-3,5-pyridinedicarbonitrile, 2-amino-6-[[(2-chlorophenyl)-methyl]thio]-4-(2-thienyl)-3,5-pyridinedicarbonitrile, 2-amino-6-[[(2-methylphenyl) methyl]thio]-4-(2-thienyl)-3,5-pyridinedicarbonitrile, 2-amino-6-[[(3-chlorophenyl)methyl]thio]-4-(2-thienyl)-3,5-pyridinedicarbonitrile, 2-amino-6-[[(4-chlorophenyl)methyl]thio]-4-(2-thienyl)-3,5-pyridinedicarbonitrile, 2-amino-6-[[(3-fluorophenyl)methyl]thio]-4-(2-thienyl)-3,5-pyridinedicarbonitrile, 2-amino-6-[[(4-methylphenyl)methyl]thio]-4-(2-thienyl)-3,5-pyridinedicarbonitrile, 2-amino-6-[[(2-bromophenyl)methyl]thio]-4-(2-thienyl)-3,5-pyridinedicarbonitrile, 2-amino-6-[[(3-bromophenyl)-methyl]thio]-4-(2-thienyl)-3,5-pyridinedicarbonitrile, 2-amino-6-[[(4-bromophenyl)methyl]thio]-4-(2-thienyl)-3,5-pyridinedicarbonitrile, 2-amino-4-(2-thienyl)-6-[[[3-(trifluoromethyl)phenyl]-methyl]thio]-3,5- pyridinedicarbonitrile, 2-amino-6-[[(3-methoxyphenyl)methyl]thio]-4-(2-thienyl)-3,5-pyridinedicarbonitrile, 2-amino-4-(2-thienyl)-6-[[[2-(trifluoromethyl)phenyl]methyl]thio]-3,5-pyridinedicarbonitrile, 2-amino-6-[[[4-(1,1-dimethylethyl)phenyl]methyl]thio]-4-(2-thienyl)-3,5-pyridinedicarbonitrile, 2-amino-6-[[(4-fluorophenyl)methyl]thio]-4-(2-thienyl)-3,5-pyridinedicarbonitrile, 2-amino-6-[[(2-fluorophenyl)methyl]thio]-4-(2-thienyl)-3,5-pyridinedicarbonitrile, 2-amino-6-[[(2-chloro-6-fluorophenyl)methyl]thio]-4-(2-thienyl)-3,5-pyridinedicarbonitrile or 2-amino-6-[[(2,6-dichlorophenyl)methyl]thio]-4-(2-thienyl)-3,5-pyridinedicarbonitrile for the prevention and/or treatment of cardiovascular disorders.

The present invention furthermore provides the use of a compound selected from the group consisting of 2-amino-6-[[(3-methylphenyl)methyl]thio]-4-(2-thienyl)-3,5-pyridinedicarbonitrile, 2-amino-6-[[(2-chlorophenyl)methyl]thio]-4-(2-thienyl)-3,5-pyridinedicarbonitrile, 2-amino-6-[[(2-methylphenyl)methyl]thio]-4-(2-thienyl)-3,5-pyridinedicarbonitrile, 2-amino-6-[[(3-chlorophenyl)methyl]thio]-4-(2-thienyl)-3,5-pyridinedicarbonitrile, 2-amino-6-[[(4-chlorophenyl)methyl]thio]-4-(2-thienyl)-3,5-pyridinedicarbonitrile, 2-amino-6-[[(3-fluorophenyl)-methyl]thio]-4-(2-thienyl)-3,5-pyridinedicarbonitrile, 2-amino-6-[[(4-methylphenyl)methyl]thio]-4-(2-thienyl)-3,5-pyridinedicarbonitrile, 2-amino-6-[[(2-bromophenyl)methyl]thio]-4-(2-thienyl)-3,5-pyridinedicarbonitrile, 2-amino-6-[[(3-bromophenyl)methyl]thio]-4-(2-thienyl)-3,5-pyridinedicarbonitrile, 2-amino-6-[[(4-bromophenyl)methyl]thio]-4-(2-thienyl)-3,5-pyridinedicarbonitrile, 2-amino-4-(2-thienyl)-6-[[[3-(trifluoromethyl)phenyl]methyl]thio]-3,5-pyridinedicarbonitrile, 2-amino-6-[[(3-methoxyphenyl)methyl]thio]-4-(2-thienyl)-3,5-pyridinedicarbonitrile, 2-amino-4-(2-thienyl)-6-[[[2-(trifluoromethyl)phenyl]methyl]thio]-3,5-pyridinedicarbonitrile, 2-amino-6-[[[4-(1,1-dimethylethyl)phenyl]methyl]thio]-4-(2-thienyl)-3,5-pyridinedicarbonitrile, 2-amino-6-[[(4-fluorophenyl)methyl]thio]-4-(2-thienyl)-3,5-pyridinedicarbonitrile, 2-amino-6-[[(2-fluorophenyl)methyl]thio]-4-(2-thienyl)-3,5-pyridinedicarbonitrile, 2-amino-6-[[(2-chloro-6-fluorophenyl)methyl]-thio]-4-(2-thienyl)-3,5-pyridinedicarbonitrile and 2-amino-6-[[(2,6-dichlorophenyl)methyl]thio]-4-(2-thienyl)-3,5-pyridinedicarbonitrile for preparing medicaments or pharmaceutical preparations for the prevention and/or treatment of cardiovascular disorders.

The present invention furthermore provides a process for preparing the compounds of the formula (I) according to the invention, characterized in that
[A] a compound of the formula (II)

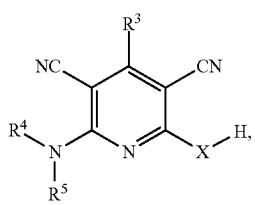
(II)

in which X, $R^3$, $R^4$ and $R^5$ each have the meanings given above,
is reacted in an inert solvent in the presence of a base with a compound of the formula (III)

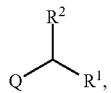
(III)

in which $R^1$ and $R^2$ each have the meanings given above and
Q represents a suitable leaving group, preferably halogen, in particular chlorine, bromine or iodine, or represents mesylate, tosylate or triflate, or
[B] if X represents O, a compound of the formula (IV)

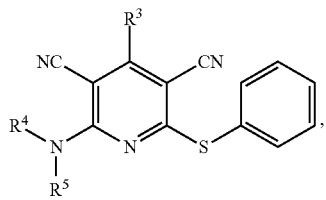
(IV)

in which $R^3$, $R^4$ and $R^5$ each have the meanings given above,
is reacted in an inert solvent in the presence of a base with a compound of the formula (V)

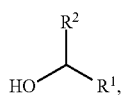
(V)

in which $R^1$ and $R^2$ have the meanings given above, or
[C] a compound of the formula (I-A)

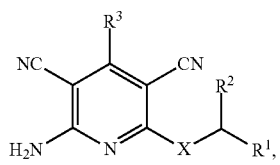
(I-A)

in which $R^1$, $R^2$ and $R^3$ each have the meanings given above,
is initially converted with copper(II) chloride and isoamyl nitrite in a suitable solvent into a compound of the formula (XV)

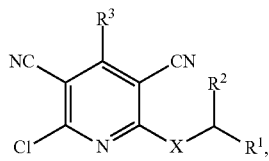
(XV)

in which $R^1$, $R^2$ and $R^3$ each have the meanings given above,
and this is then reacted with a compound of the formula (VIII)

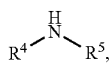
(VIII)

in which $R^4$ and $R^5$ each have the meanings given above,
and
in which at least one of the two radicals $R^4$ and $R^5$ is different from hydrogen, to give a compound of the formula (I-B)

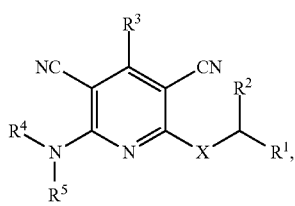
(I-B)

in which $R^1$, $R^2$, $R^3$, $R^4$ and $R^5$ each have the meanings given above,
and
in which at least one of the two radicals $R^4$ and $R^5$ is different from hydrogen, any protective groups present are then removed and the resulting compounds of the formula (I) are, if appropriate, converted with the appropriate (i) solvents and/or (ii) bases or acids into their solvates, salts and/or solvates of the salts.

Together, the compounds of the formula (I-A) and the compounds of the formula (I-B) form the compounds of the formula (I).

In this process, any functional groups present in the compounds of the formulae (II) and (IV) or in the radicals $R^3$, $R^4$ and/or $R^5$—such as, in particular, amino, hydroxyl and carboxyl groups—can, if expedient or required, also be present in temporarily protected form. The introduction and removal of such protective groups takes place in this connection by conventional methods known to the person skilled in the art [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. If a plurality of protective groups is present, the removal may, if appropriate, take place simulataneously in a one-pot reaction or in separate reaction steps.

The amino protective group which is preferably used is tert-butoxycarbonyl (Boc) or benzyloxycarbonyl (Z). Suitable for protecting carboxyl groups are in particular the appropriate methyl, ethyl or tert-butyl esters. A preferred protective group used for a hydroxyl function is benzyl or a silyl group such as trimethylsilyl, tert-butyldimethylsilyl or dimethylphenylsilyl. If a 1,2- or 1,3-diol grouping is present, preference is given to using a ketal derived from symmetric ketones such as acetone or cyclohexanone (1,3-dioxolane or 1,3-dioxane) as joint protective group.

The process described above can be illustrated in an exemplary manner by Reaction Schemes 1 and 2 below:

Scheme 1

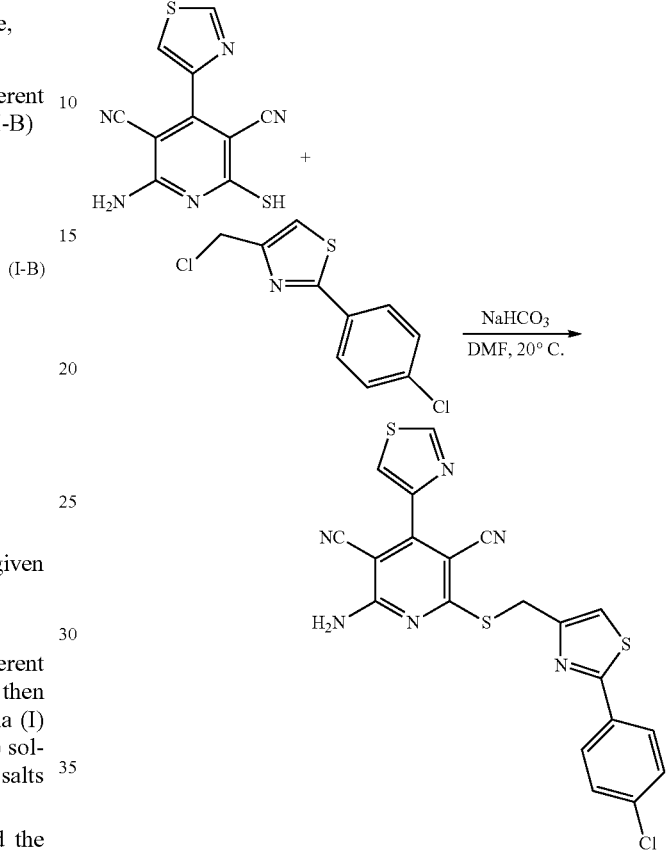

Scheme 2

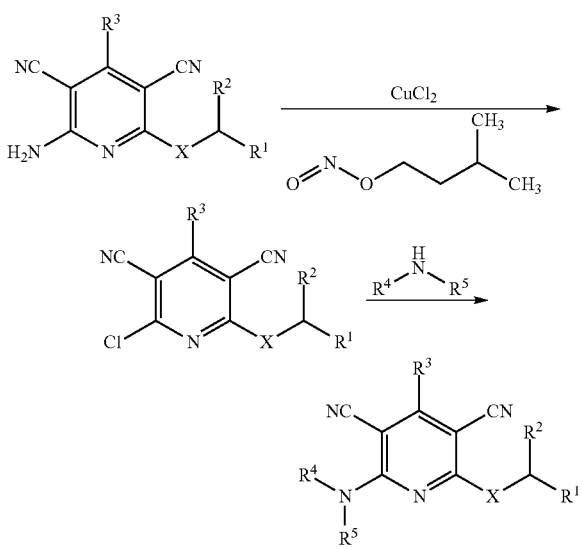

Suitable solvents for the reaction (II)+(III) are all organic solvents which are inert under the reaction conditions. These include ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or -butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. It is also possible to use mixtures of the solvents mentioned above. Preference is given to using dimethylformamide.

Suitable bases for this reaction are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and bicarbonates, such as potassium carbonate and sodium bicarbonate.

Here, the base can be employed in an amount of from 1 to 10 mol, preferably from 1 to 5 mol, in particular from 1 to 3 mol, based on 1 mol of the compound of the formula (II).

The reaction (II)+(III) is generally carried out in a temperature range of from −78° C. to +140° C., preferably in the range from −20° C. to +100° C., in particular at from 0° C. to +60° C. (for X=S) or +20° C. to +100° C. (for X=O), if appropriate in a microwave. The reaction can be carried out at atmospheric, elevated or reduced pressure (for example in the range from 0.5 to 5 bar). The reaction is generally carried out at atmospheric pressure.

Suitable inert solvents for the reaction (IV)+(V) are in particular acyclic and cyclic ethers, such as diethyl ether, methyl tert-butyl ether, 1,2-dimethoxyethane, tetra-hydrofuran and dioxane, hydrocarbons, such as benzene, toluene, xylene, hexane and cyclohexane, or dipolar solvents, such as dimethylformamide (DMF), dimethyl sulfoxide (DMSO), N-methylpyrrolidinone (NMP) and pyridine. It is also possible to use mixtures of the solvents mentioned above. Preference is given to using 1,2-dimethoxyethane.

Suitable bases for this reaction are in particular alkali metal alkoxides, such as sodium methoxide or potassium methoxide, sodium ethoxide or potassium ethoxide or sodium tert-butoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, or organometallic compounds, such as butyllithium or phenyllithium. Preference is given to using potassium tert-butoxide.

Here, the base is generally employed in an amount of from 1 to 1.25 mol, preferably in an equimolar amount, based on 1 mol of the compound of the formula (V).

The reaction (IV)+(V) is generally carried out in a temperature range of from −20° C. to +120° C., preferably at from +20° C. to +100° C., if appropriate in a microwave. The reaction can be carried out at atmospheric, elevated or reduced pressure (for example in the range from 0.5 to 5 bar). The reaction is generally carried out at atmospheric pressure.

The process step (I-A)→(XV) is generally carried out using a molar ratio of from 2 to 12 mol of copper(II) chloride and from 2 to 12 mol of isoamyl nitrite, based on 1 mol of the compound of the formula (I-A).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of these solvents. Preferred solvents are acetonitrile and dimethyl-formamide.

The reaction is generally carried out in a temperature range of from −78° C. to +180° C., preferably in the range from +20° C. to +100° C., in particular at from +20° C. to +60° C., if appropriate in a microwave. The reaction can be carried out at atmospheric, elevated or reduced pressure (for example in the range from 0.5 to 5 bar). The reaction is generally carried out at atmospheric pressure.

The process step (XV)+(VIII) is generally carried out using a molar ratio of from 1 to 8 mol of the compound of the formula (VIII), based on 1 mol of the compound of the formula (XV).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxy-ethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine or dimethyl sulfoxide. Another suitable solvent is water. It is also possible to use mixtures of these solvents. The preferred solvent is dimethylformamide.

The reaction is generally carried out in a temperature range of from 0° C. to +180° C., preferably in the range from +20° C. to +120° C., in particular at from +20° C. to +100° C., if appropriate in a microwave. The reaction can be carried out at atmospheric, elevated or reduced pressure (for example in the range from 0.5 to 5 bar). The reaction is generally carried out at atmospheric pressure.

The compounds of the formula (VIII) are either commercially available or known to the person skilled in the art, or they can be prepared by customary methods.

The compounds of the formula (III) are commercially available or known from the literature, or they can be prepared by methods known from the literature. Thus, substituted oxazole and thiazole derivatives of the formulae (III-A) and (III-B) can be obtained, for example, by reacting amides and thioamides, respectively, with a 1,3-dihaloacetone (see Scheme 3):

Scheme 3

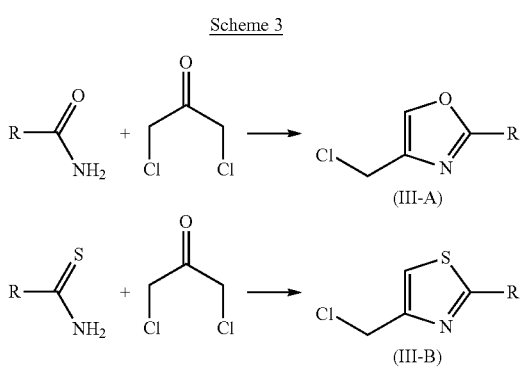

The compounds of the formula (V) are commercially available or known from the literature, or they can be prepared analogously to processes described in the literature, for example similar to the compounds of the formula (III).

Compounds of the formula (II) in which X represents S and $R^4$ and $R^5$ represent hydrogen can be prepared analogously to methods known from the literature, for example by reacting aldehydes of the formula (VI)

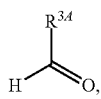

(VI)

in which
$R^{3A}$ represents thienyl, pyrrolyl which is attached via carbon, oxazolyl, thiazolyl, isoxazolyl, isothiazolyl, pyrazolyl which is attached via carbon, imidazolyl which is attached via carbon, triazolyl which is attached via carbon, oxadiazolyl, thiadiazolyl or tetrazolyl which is attached via carbon,
which may be substituted within the scope of the meaning given for $R^3$, in the presence of a base with two equivalents of cyanothioacetamide [see Scheme 4; cf., for example, Dyachenko et al., *Russ. J. Chem.* 33 (7), 1014-1017 (1997), 34 (4), 557-563 (1998); Dyachenko et al., *Chemistry of Heterocyclic Compounds* 34 (2), 188-194 (1998); Qintela et al., *Eur. J. Med. Chem.* 33, 887-897 (1998); Kandeel et al., *Z. Naturforsch.* 42b, 107-111 (1987); Reddy et al., *J. Med. Chem.* 49, 607-615 (2006); Evdokimov et al., *Org. Lett.* 8, 899-902 (2006)].

Scheme 4

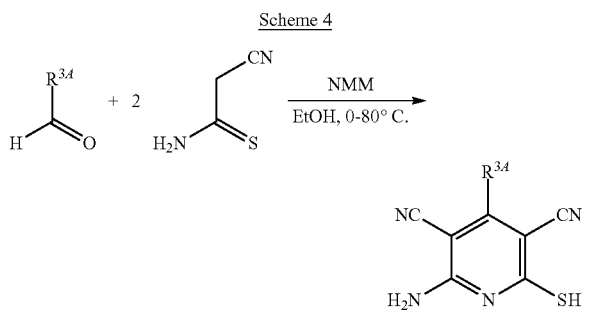

The compounds of the formula (IV) can be prepared analogously to processes described in the literature [cf., for example, Kambe et al., *Synthesis*, 531-533 (1981); Elnagdi et al., *Z. Naturforsch.* 47b, 572-578 (1991); Reddy et al., *J. Med. Chem.* 49, 607-615 (2006); Evdokimov et al., *Org. Lett.* 8, 899-902 (2006)] or by reacting compounds of the formula (II) in which X represents S analogously to processes described in the literature [cf., for example, Fujiwara, H. et al., *Heterocycles* 1993, 36 (5), 1105-1113, Su et al., *J. Med. Chem.* 1988, 31, 1209-1215].

The compounds of the formula (VI) are commercially available or known from the literature, or they can be prepared by methods known from the literature.

Compounds of the formula (II) in which X represents S can also be obtained from compounds of the formula (IV) by reaction with an alkali metal sulfide. This preparation method is illustrated by Formula Scheme 5 below:

Scheme 5

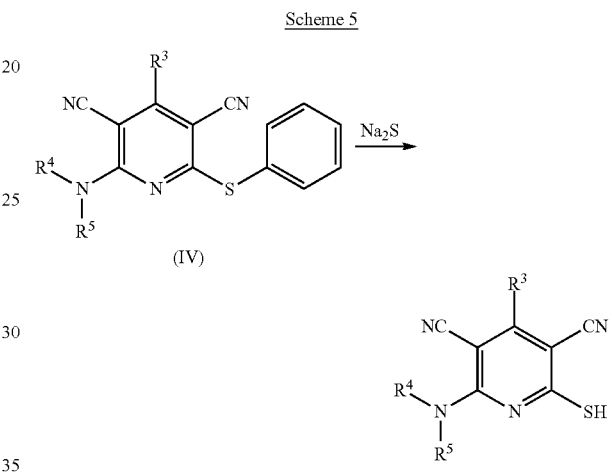

The alkali metal sulfide employed is preferably sodium sulfide in an amount of from 1 to 10 mol, preferably from 1 to 8 mol, in particular from 1 to 5 mol, based on 1 mol of the compound of the formula (IV).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxy-ethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or dipolar solvents, such as acetonitrile, pyridine, dimethylform-amide, dimethyl sulfoxide or N-methylpyrrolidinone. Another suitable solvent is water. It is also possible to use mixtures of these solvents. The preferred solvent is dimethylformamide.

The reaction is generally carried out in a temperature range of from 0° C. to +180° C., preferably in the range from +20° C. to +120° C., in particular at from +40° C. to +100° C., if appropriate in a microwave. The reaction can be carried out at atmospheric, elevated or reduced pressure (for example in the range from 0.5 to 5 bar). The reaction is generally carried out at atmospheric pressure.

Compounds of the formula (IV) in which at least one of the two radicals $R^4$ and $R^5$ does not represent hydrogen can be prepared by initially converting compounds of the formula (IVa)

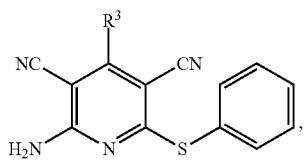
(IVa)

in which R³ has the meaning given above,
with copper(II) chloride and isoamyl nitrite in a suitable solvent into compounds of
the formula (VII)

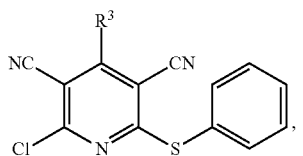
(VII)

in which R³ has the meaning given above,
and then reacting with a compound of the formula (VIII)

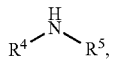
(VIII)

in which R⁴ and R⁵ each have the meanings given above,
and
where at least one of the two radicals R⁴ and R⁵ is different from hydrogen, to give compounds of the formula (IVb)

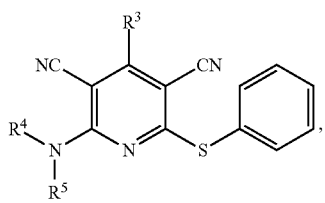
(IVb)

in which R³, R⁴ and R⁵ each have the meanings given above; if appropriate, these can then be converted with the aid of an alkali metal sulfide as described above into corresponding compounds of the formula (II) in which X represents S and at least one of the two radicals R⁴ and R⁵ does not represent hydrogen. This process can be illustrated by the reaction scheme below:

Scheme 6

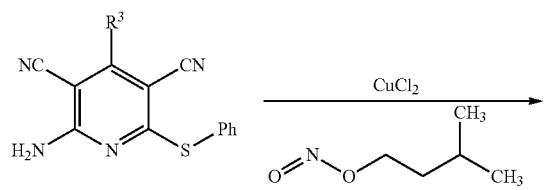

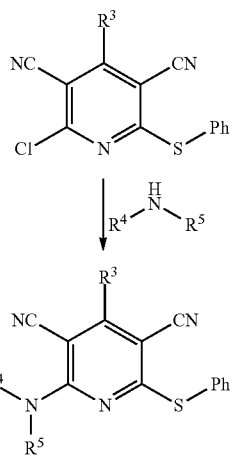

[Ph = phenyl].

For this process path, the reaction parameters described above for the sequence (I-A)→(XV)→(I-B), such as solvents, reaction temperatures and molar ratios, are applied in an analogous manner.

Compounds of the formula (II) in which X represents O can be obtained from compounds of the formula (IV) by heating with an alkali metal hydroxide. This preparation method is illustrated by the reaction scheme below:

Scheme 7

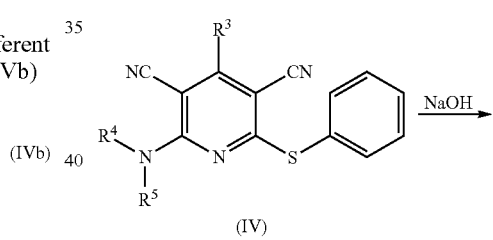
(IV)

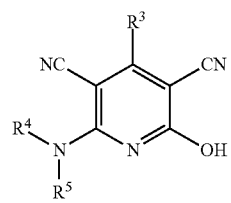

The alkali metal hydroxide used is preferably excess sodium hydroxide or potassium hydroxide. Suitable solvents are in particular alcohols, such as methanol, ethanol, n-propanol, isopropanol, n-butanol and tert-butanol, and also their mixtures with water.

The reaction is generally carried out in a temperature range of from +20° C. to +120° C., preferably at from +50° C. to +100° C.

Other compounds of the formula (II) in which X represents S and R⁴ and R⁵ represent hydrogen can be prepared by converting the compound of the formula (IX)

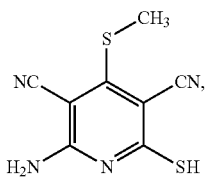

(IX)

in an inert solvent in the presence of a base with a compound of the formula (III) into a compound of the formula (X)

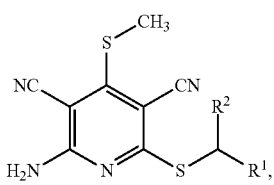

(X)

in which $R^1$ and $R^2$ have the meanings given above,
and then reacting this in an inert solvent or in the absence of a solvent with a compound of the formula (XI)

$R^{3B}$—H  (XI), in which
$R^{3B}$ represents nitrogen-bonded pyrrolyl, pyrazolyl, imidazolyl, triazolyl or tetrazolyl,
each of which may be substituted within the scope of the meaning given for $R^3$, to give compounds of the formula (II-B)

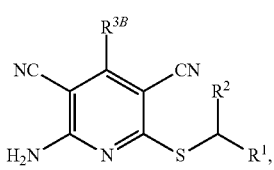

(II-B)

in which $R^1$, $R^2$ and $R^{3B}$ each have the meanings given above.

Suitable solvents for the process step (IX)+(III)→(X) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloro-methane, trichloromethane and chlorobenzene, or other solvents, such as dimethyl-formamide (DMF), dimethyl sulfoxide (DMSO), N-methylpyrrolidinone (NMP), acetonitrile or pyridine. Another suitable solvent is water. It is also possible to use mixtures of the solvents mentioned above. Preferred for use as solvent is dimethyl-formamide.

Suitable bases for the process step (IX)+(III)→(X) are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and bicarbonates.

Here, the base can be employed in an amount of from 1 to 10 mol, preferably from 1 to 5 mol, in particular from 1 to 4 mol, based on 1 mol of the compound of the formula (IX).

The reaction is generally carried out in a temperature range of from −78° C. to +140° C., preferably in the range from −20° C. to +80° C., in particular at from 0° C. to +50° C., if appropriate in a microwave. The reaction can be carried out at atmospheric, elevated or reduced pressure (for example in the range from 0.5 to 5 bar). The reaction is generally carried out at atmospheric pressure.

Suitable solvents for the process step (X)+(XI)→(II-B) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane and chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. If appropriate, the reaction can also be carried out advantageously in the presence of an excess of the compound (XI), without addition of a further solvent. Preferably, the reaction is carried out in acetone or N-methyl-pyrrolidinone as solvent.

The process step (X)+(XI)→(II-B) is generally carried out in a temperature range of from 0° C. to +180° C., preferably in the range from +20° C. to +100° C., in particular at from +60° C. to +100° C., if appropriate in a microwave. The reaction can take place under atmospheric, elevated or reduced pressure (for example in the range from 0.5 to 5 bar). In general, the reaction is carried out at atmospheric pressure.

The compounds of the formula (XI) are commercially available or known from the literature, or they can be prepared analogously to processes known from the literature.

The compound of the formula (IX) can be obtained in a simple manner by reacting [bis(methylthio)methylene]malononitrile with cyanothioacetamide in the presence of a base such as triethylamine.

Other compounds of the formula (II) in which X represents O and $R^4$ and $R^5$ represent hydrogen can be prepared by converting the compound of the formula (XII)

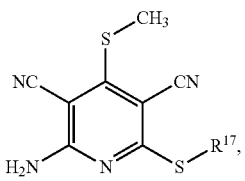

(XII)

in which
R[17] represents ($C_1$-$C_4$)-alkyl or phenyl,
in an inert solvent in the presence of a base with a compound of the formula (V) into a compound of the formula (XIII)

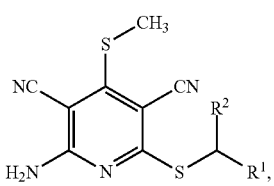

(XIII)

in which R[1] and R[2] have the meanings given above,
and then reacting this in an inert solvent or in the absence of a solvent with a compound of the formula (XI) to give compounds of the formula (II-C)

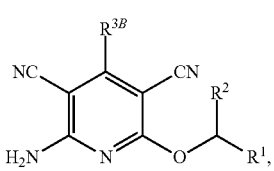

(II-C)

in which R[1], R[2] and R[3B] each have the meanings given above, or
alternatively initially reacting a compound of the formula (XII) in an inert solvent or in the absence of a solvent with a compound of the formula (XI) to give compounds of the formula (XIV)

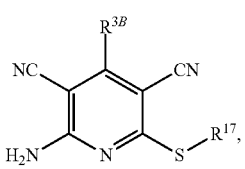

(XIV)

in which R[3B] and R[17] each have the meanings given above, and then converting these with a compound of the formula (V) into compounds of the formula (II-C).

The compounds of the formula (XII) in which R[17] represents phenyl can be prepared from the compound of the formula (IX) analogously to the process described in Fujiwara, H. et al., *Heterocycles* 1993, 36 (5), 1105-1113.

The compounds of the formula (XII) in which R[17] represents ($C_1$-$C_4$)-alkyl can be prepared from the compound of the formula (IX) analogously to the process described in Su et al., *J. Med. Chem.* 1988, 31, 1209-1215.

Suitable inert solvents for the reactions (XII)+(V) and (XIV)+(V) are in particular acyclic and cyclic ethers, such as diethyl ether, methyl tert-butyl ether, 1,2-dimeth-oxyethane, tetrahydrofuran and dioxane, hydrocarbons, such as benzene, toluene, xylene, hexane and cyclohexane, or other solvents, such as dimethylformamide (DMF), dimethyl sulfoxide (DMSO), N-methylpyrrolidinone (NMP) and pyridine. It is also possible to use mixtures of these solvents. Preference is given to using 1,2-dimethoxyethane.

Suitable bases for these reactions are in particular alkali metal alkoxides, such as sodium methoxide or potassium methoxide, sodium ethoxide or potassium ethoxide or sodium tert-butoxide or potassium tert-butoxide, alkali metal hydrides, such as lithium hydride, sodium hydride or potassium hydride, amides, such as sodium amide, lithium bis(trimethylsilyl)amide, sodium bis(trimethylsilyl)amide or potassium bis(trimethylsilyl)amide or lithium diisopropylamide, or organometallic compounds, such as butyllithium or phenyllithium. Preference is given to potassium tert-butoxide. Here, the base can be employed in an amount of from 1 to 1.25 mol, preferably in an equimolar amount, based on 1 mol of the compound of the formula (V).

The reactions (XII)+(V) and (XIV)+(V) are generally carried out in a temperature range of from −20° C. to +120° C., preferably at from +20° C. to +100° C., if appropriate in a microwave. The reactions can be carried out at atmospheric, elevated or reduced pressure (for example in the range from 0.5 to 5 bar). The reactions are generally carried out at atmospheric pressure.

Suitable solvents for the process steps (XII) or (XIII)+(XI) →(II-C) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane and chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. If appropriate, the reaction can also be carried out advantageously in the presence of an excess of the compound (XI), without addition of a further solvent. Preferably, the reaction is carried out in acetone or N-methyl-pyrrolidinone as solvent.

The process steps (XII) or (XIII)+(XI)→(II-C) are generally carried out in a temperature range of from 0° C. to +180° C., preferably in the range from +20° C. to +100° C., in particular at from +60° C. to +100° C., if appropriate in a microwave. The reaction can be carried out at atmospheric, elevated or reduced pressure (for example in the range from 0.5 to 5 bar). The reactions are generally carried out at atmospheric pressure.

Scheme 8

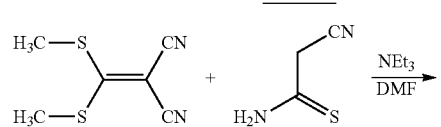

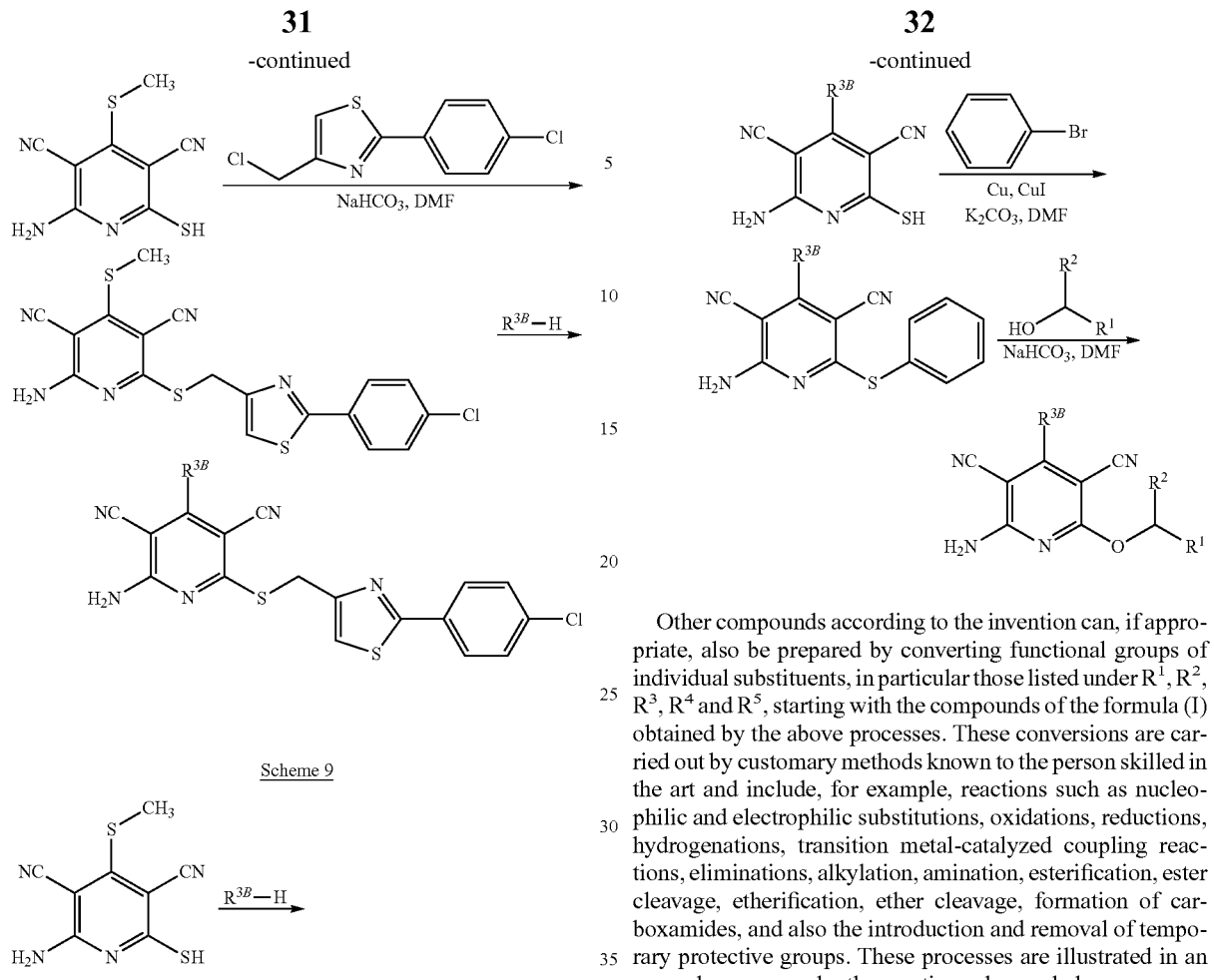

Other compounds according to the invention can, if appropriate, also be prepared by converting functional groups of individual substituents, in particular those listed under $R^1$, $R^2$, $R^3$, $R^4$ and $R^5$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups. These processes are illustrated in an exemplary manner by the reaction schemes below:

-continued

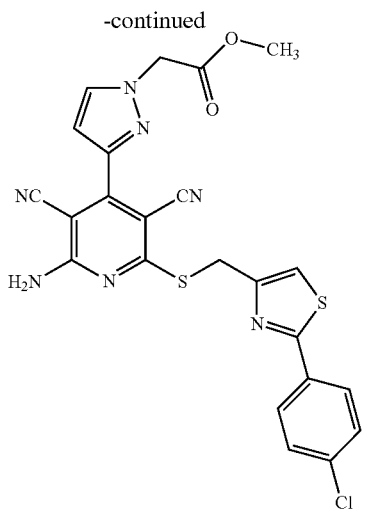

Scheme 11

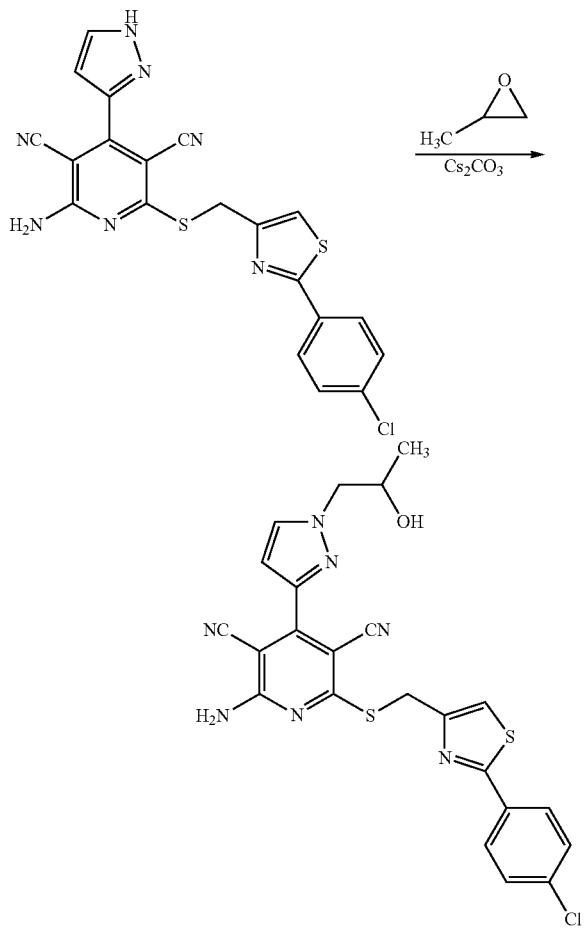

Surprisingly, the compounds according to the invention have an unforeseeable useful pharmacological activity spectrum and are therefore particularly suitable for the prophylaxis and/or treatment of disorders.

The pharmaceutical activity of the compounds according to the invention can be explained by their action as potent, selective ligands at adenosine A1 receptor. Here, they act as selective A1 agonists or as selective A1 antagonists. The compounds according to the invention have an identical or improved physicochemical, pharmacokinetic and/or therapeutic profile. The compounds according to the invention act mainly as selective adenosine A1 agonists.

In the context of the present invention, "selective ligands at adenosine A1 receptor" are adenosine receptor ligands where firstly a marked activity at A1 adenosine receptor and secondly no or a considerably weaker activity (by a factor of 10 or more) at A2a, A 2b and A3 adenosine receptor subtypes can be observed, where with respect to the test methods for activity/selectivity, reference is made to the tests described in sections B-1 and B-5.

Depending on their particular structure, the compounds according to the invention can act as full or as partial adenosine receptor agonists or as adenosine receptor antagonists. Partial adenosine receptor agonists are defined here as receptor—ligands which trigger a functional response at adenosine receptors which is less than that of full agonists (such as, for example, adenosine itself). Accordingly, partial agonists have lower activity with respect to receptor activation than full agonists. The compounds of the formula (I) are suitable alone or in combination with one or more other active ingredients for the prophylaxis and/or treatment of various disorders, for example disorders of the cardiovascular system (cardiovascular disorders), for cardio protection following lesions of the heart, and of metabolic disorders and kidney disorders.

Disorders of the cardiovascular system, or cardiovascular disorders, mean in the context of the present invention for example the following disorders: peripheral and cardiac vascular disorders, coronary heart disease, coronary restenosis such as, for example, restenosis following balloon dilatation of peripheral blood vessels, myocardial infarction, acute coronary syndrome, acute coronary syndrome with ST elevation, acute coronary syndrome without ST elevation, stable and unstable angina pectoris, myocardial insufficiency, princemetal angina, persistent ischemic dysfunction ("hibernating myocardium"), temporary postischemic dysfunction ("stunned myocardium"), heart failure, tachycardia, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, disturbances of peripheral blood flow, elevated levels of fibrinogen and of low density LDL, and elevated concentrations of plasminogen activator inhibitor 1 (PAI-1), especially coronary heart disease, acute coronary syndrome, angina pectoris, heart failure, myocardial infarction and atrial fibrillation.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure. The compounds according to the invention are further also suitable for reducing the area of myocardium affected by an infarction, and for the prophylaxis of secondary infarctions.

The compounds according to the invention are furthermore suitable for the prophylaxis and/or treatment of thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (CABG), primary PTCAs, PTCAs after thrombolysis, rescue PTCA, heart transplants and open-heart operations, and for organ protection in connection with transplants, bypass operations, catheter examinations and other surgical procedures.

Furthermore, the compounds according to the invention are suitable for the treatment and/or prevention of kidney diseases, in particular of renal insufficiency. In the context of the present invention, the term renal insufficiency comprises both acute and chronic manifestations of renal insufficiency, as well as underlying or related kidney diseases such as renal hypoperfusion, obstructive uropathy, glomerulonephritis, acute glomerulonephritis, tubulointerstitial diseases, nephropathic diseases such as primary and congenital kidney disease, nephritis, nephropathy induced by toxic substances, diabetic nephropathy, pyelonephritis, renal cysts and nephrosclerosis, which can be characterized diagnostically for example by abnormally reduced creatinine and/or water excretion, abnormally raised blood concentrations of urea, nitrogen, potassium and/or creatinine, altered activity of renal enzymes, such as, for example, glutamylsynthetase, altered urine osmolarity or urine volume, increased microalbuminuria, macroalbuminuria, lesions on glomeruli and arterioles, tubular dilatation, hyperphosphatemia and/or need for dialysis. The present invention also comprises the use of the compounds according to the invention for the treatment and/or prevention of sequelae of renal insufficiency, for example pulmonary edema, heart failure, uraemia, anemia, electrolyte disturbances (for example hyperkalemia, hyponatremia) and disturbances in bone and carbohydrate metabolism.

Other areas of indication for which the compounds according to the invention can be employed are, for example, the prevention and/or treatment of disorders of the uro-genital tract, such as, for example, irritable bladder, erectile dysfunction and female sexual dysfunction, but in addition also the prevention and/or treatment of inflammatory disorders, such as, for example, inflammatory dermatoses (psoriasis, acne, eczema, neurodermitis, dermatitis, keratitis, formation of scars, formation of warts, frostbites), of disorders of the central nervous system and neurodegenerative disorders (strokes, Alzheimer's disease, Parkinson's disease, dementia, epilepsy, depression, multiple sclerosis), of states of pain, cancerous diseases (skin cancer, liposarcomas, carcinomas of the gastrointestinal tract, the liver, pancreas, lung, kidney, ureter, prostate and the genital tract), and also of nausea and emesis associated with cancer therapies.

Other areas of indication are, for example, the prevention and/or treatment of inflammatory and immune disorders (Crohn's disease, ulcerative colitis, lupus erythematodes, rheumatoid arthritis) and respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Finally, the compounds according to the invention are also suitable for the prevention and/or treatment of diabetes, in particular diabetes mellitus, gestation diabetes, insulin-dependent diabetes and non-insulin-dependent diabetes, of diabetic sequelae such as, for example, retinopathy, nephropathy and neuropathy, of metabolic disorders (metabolic syndrome, hyperglycemia, gestational diabetes, hyperinsulinemia, insulin resistance, glucose intolerance, obesity (adipositas)) and also of arteriosclerosis and dyslipidemias (hypercholesterolemia, hypertriglyceridemia, elevated concentrations of postprandial plasma triglycerides, hypoalphalipoproteinemia, combined hyperlipidemias), in particular of diabetes, metabolic syndrome and dyslipidemias.

In addition, the compounds according to the invention can also be used for the treatment and/or prevention of disorders of the thyroid gland (hyperthyreosis), disorders of the pancreas (pancreatitis), fibrosis of the liver, viral diseases (HPV, HCMV, HIV), cachexia, osteoporosis, gout, incontinence, and also for wound healing and angiogenesis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The present invention furthermore provides the compounds according to the invention for use in a method for the treatment and/or prophylaxis of coronary heart disease, acute coronary syndrome, angina pectoris, heart failure, myocardial infarction and atrial fibrillation.

The present invention furthermore provides the compounds according to the invention for methods for the treatment and/or prophylaxis of diabetes, metabolic syndrome and dyslipidemias.

The compounds according to the invention can be used alone or, if required, in combination with other active ingredients. The present invention furthermore provides medicaments comprising at least one of the compounds according to the invention and one or more further active ingredients, in particular for the treatment and/or prevention of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics for example aspirin, antidepressants and other psychopharmaceuticals.

The present invention relates in particular to combinations of at least one of the compounds according to the invention with at least one lipid metabolism-altering active ingredient, antidiabetic, blood pressure-reducing active ingredient and/or agent having antithrombotic effects.

The compounds according to the invention can preferably be combined with one or more lipid metabolism-modulating active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example and by way of preference from the group of the platelet aggregation inhibitors or the anticoagulants;

diuretics;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, by way of example, iloprost, beraprost, cicaprost;

inhibitors of the $I_f$ (funny channel) channel, such as, by way of example, ivabradine;

calcium sensitizers, such as, by way of example and by way of preference, levosimendan;

potassium supplements;

NO-independent, but heme-dependent stimulators of guanylate cyclase, such as, in particular, the compounds described in WO 00/06568, WO 00/06569, WO 02/42301 and WO 03/095451;

NO- and heme-independent activators of guanylate cyclase, such as, in particular, the compounds described in WO 01/19355, WO 01/19776, WO 01/19778, WO 01/19780, WO 02/070462 and WO 02/070510;

inhibitors of human neutrophil elastase (HNE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib;

and/or compounds which modulate the energy metabolism of the heart, such as, for example, etomoxir, dichloroacetate, ranolazine and trimetazidine.

Lipid metabolism-modifying active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastation or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130. In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist for example from the class of the thiazolidinediones, such as, by way of example and by way of preference, pioglitazone or rosiglitazone.

In a preferred embodiment of the invention, the compounds according to the invention are administered in combination with a PPAR-δ agonist such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778. Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulfonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin and vildagliptin.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate, molsidomin or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, dabigatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralo-corticoid receptor antagonists, vasopressin receptor antagonists, platelet aggre-gation inhibitors and anticoagulants, and also their use for the treatment and/or prevention of the disorders mentioned above.

The present invention furthermore provides medicaments comprising at least one compound according to the invention, usually together with one or more inert, nontoxic, pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert, non-toxic, pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active ingredient, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used:
aq. aqueous
br s broad singlet (in NMR)
Ex. Example
c concentration
d doublet (in NMR)
dd doublet of doublets (in NMR)
DBU 1,8-diazabicyclo[5.4.0]undec-7-ene
TLC thin-layer chromatography
DCI direct chemical ionization (in MS)
DMF N,N-dimethylformamide
DMSO dimethyl sulfoxide
ee enantiomeric excess
EI electron impact ionization (in MS)
ESI electrospray ionization (in MS)
Et ethyl
m.p. melting point
h hour(s)
HPLC high-pressure, high-performance liquid chromatography
cat. catalytic
conc. concentrated
LC-MS liquid chromatography-coupled mass spectrometry
lit. literature (reference)
MeCN acetonitrile
min minute(s)
MS mass spectrometry
NMR nuclear magnetic resonance spectrometry
q quartet (in NMR)
rac. racemic
RP-HPLC reversed-phase HPLC
RT room temperature
$R_t$ retention time (in HPLC)
s singlet (in NMR)
t triplet (in NMR)
t-Bu tert-butyl
TFA trifluoroacetic acid
THF tetrahydrofuran
dil. dilute
HPLC, LC-MS and GC-MS methods:

Method 1 (LC-MS): MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 2 (LC-MS): MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 3 (LC-MS): Instrument: Micromass QuattroPremier with Waters HPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.

Method 4 (LC-MS): MS instrument type: Micromass ZQ; HPLC instrument type: Waters Alliance 2795; column: Phenomenex Synergi 2p Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 5 (LC-MS): MS instrument type: Waters (Micromass) Quattro Micro; HPLC instrument type: Agilent 1100 series; column: Thermo Hypersil GOLD 3µ 20×4 mm; mobile phase A: 1 l of water+0.5 ml of 50% strength formic acid, mobile phase B: 1 of acetonitrile+0.5 ml of 50% strength formic acid; gradient: 0.0 min 100% A→3.0 min 10% A→4.0 min 10% A→4.01 min 100% A (flow rate 2.5 ml)→5.00 min 100% A; oven: 50° C.; flow rate: 2 ml/min; UV detection: 210 nm.

Method 6 (LC-MS): MS instrument type: Waters ZQ; HPLC instrument type: Agilent 1100 series; UV DAD; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% B flow rate: 2.5 ml/min, oven: 55° C.; UV detection: 210 nm.

Method 7 (LC-MS):

Instrument: Waters ACQUITY SQD HPLC System; column: Waters Acquity HPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Starting materials and intermediates:

Example 1A 4-(Hydroxymethyl)-N-methylpyridine-2-carboxamide hydrochloride monohydrate

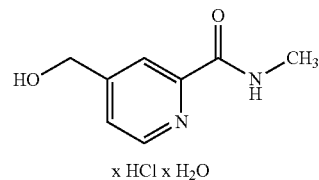

x HCl x H$_2$O

The preparation was carried out as described in U.S. Pat. No. 6,689,883 for intermediate H.

Example 2A 4-(Chloromethyl)-N-methylpyridine-2-carboxamide hydrochloride

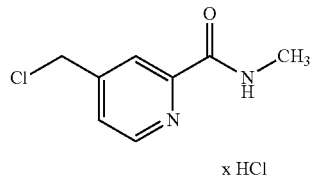

x HCl 10 g (45.32 mmol) of the compound from Example 1A were suspended in 160 ml of dichloromethane and cooled to 0° C. After addition of 16.18 g (135.96 mmol) of thionyl chloride, the reaction mixture was warmed to RT and stirred at RT overnight.

The reaction was then concentrated by evaporation, and the residue was dried under high vacuum.

Yield: 10 g (about 100% of theory)

LC-MS (Method 3): $R_t$=0.71 min; MS (ESIpos): m/z=185 $[M+H]^+$ $^1$H-NMR (400 MHz, DMSO-$d_6$): δ=8.85-8.78 (m, 1H); 8.65 (d, 1H); 8.10 (s, 1H); 7.64 (d, 1H); 4.90 (s, 2H); 2.83 (d, 3H).

Example 3A

2-Amino-6-sulfanyl-4-(1,3-thiazol-4-yl)pyridine-3,5-dicarbonitrile

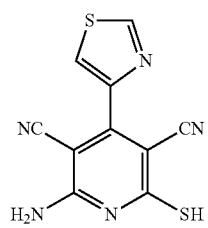 [SMILES: N#Cc1c(N)nc(S)c(C#N)c1-c1cscn1]

492 mg (4.349 mmol) of 1,3-thiazole-4-carbaldehyde, 871 mg (8.697 mmol) of 2-cyanoethanethioamide and 880 mg (8.697 mmol) of N-methylmorpholine were dissolved in 10 ml of ethanol. The reaction mixture was stirred at room temperature overnight, the solvent was removed under reduced pressure and acetonitrile was added to the residue. The solid was filtered off and washed with acetonitrile, and the filter cake was dried under reduced pressure. This gave 181 mg (14% of theory, 86% pure) of the target compound.

LC-MS (Method 1): $R_t$=0.76 min; MS (ESIpos): m/z=260 $[M+H]^+$.

Example 4A

2-Amino-6-sulfanyl-4-(1,3-thiazol-5-yl)pyridine-3,5-dicarbonitrile

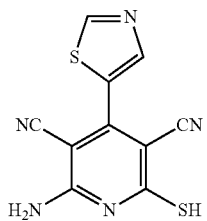 [SMILES: N#Cc1c(N)nc(S)c(C#N)c1-c1cncs1]

1.136 g (9.539 mmol) of 1,3-thiazole-5-carbaldehyde, 1.910 g (19.077 mmol) of 2-cyanoethanethioamide and 1.930 g (19.077 mmol) of N-methylmorpholine were dissolved in 20 ml of ethanol. The reaction mixture was stirred at room temperature for 20 h, and the solvent was then removed under reduced pressure. The residue was purified by chromatography on silica gel (mobile phase: dichlormethane/methanol 10:1). The product-containing fractions were collected, the solvent was removed under reduced pressure and the residue was triturated with acetonitrile. Filtration and drying of the solid gave 920 mg (37% of theory) of the target compound.

LC-MS (Method 2): $R_t$=1.30 min; MS (ESIpos): m/z=260 $[M+H]^+$.

Example 5A

2-Amino-6-sulfanyl-4-thiophen-2-ylpyridine-3,5-dicarbonitrile

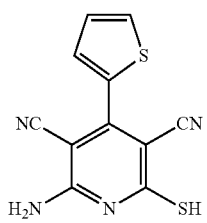 [SMILES: N#Cc1c(N)nc(S)c(C#N)c1-c1cccs1]

The preparation was carried out analogously to Example 4A using the appropriate starting materials.

LC-MS (Method 1): $R_t$=1.24 min; MS (ESIpos): m/z=258 [M]⁺.

Example 6A

2-Amino-4-(1H-pyrazol-3-yl)-6-sulfanylpyridine-3,5-dicarbonitrile

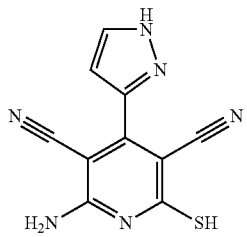 [SMILES: N#Cc1c(N)nc(S)c(C#N)c1-c1cc[nH]n1]

1.72 ml (15.61 mmol) of N-methylmorpholine were added to 0.75 g (7.81 mmol) of 1H-pyrazole-3-carbaldehyde and 1.56 g (15.61 mmol) of 2-cyanothioacetamide in 26 ml ethanol, and the mixture was heated under reflux for 4 h. The precipitate formed was filtered off and washed with a little ethanol.

Yield: 673 mg (36% of theory)

LC-MS (Method 3): $R_t$=0.44 min; MS (ESIpos): m/z=243 [M+H]⁺.

The examples listed in Table 1 were prepared analogously to Example 6A from the appropriate starting materials:

TABLE 1

| Example No. | Structure (yield) | LC-MS: $R_t$ [min] (method); MS (ESI): m/z [M + H]⁺ |
|---|---|---|
| 7A | (38% of theory) | 0.32 min (Method 3); m/z = 243 |
| 8A | (72% of theory, LC-MS: purity: 50%) | 0.62 min (Method 3); m/z = 260 |

TABLE 1-continued

| Example No. | Structure (yield) | LC-MS: $R_t$ [min] (method); MS (ESI): m/z [M + H]⁺ |
|---|---|---|
| 9A | (77% of theory, LC-MS: purity: about 50%) | 0.88 min (Method 5); m/z = 243 |
| 10A | (76% of theory, LC-MS: purity: about 40%) | 1.34 min (Method 2); m/z = 257 |

Example 11A

2-Chloro-6-({[2-(4-chlorophenyl)-1,3-thiazol-4-yl]methyl}sulfanyl)-4-(1,3-thiazol-5-yl)pyridine-3,5-dicarbonitrile

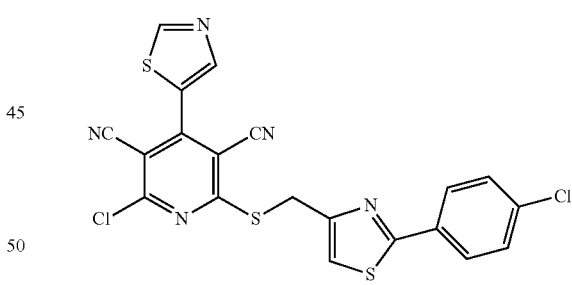

At 0° C., 50 mg (0.107 mmol) of 2-amino-6-([2-(4-chlorophenyl)-1,3-thiazol-4-yl]methylsulfanyl)-4-(1,3-thiazol-5-yl)pyridine-3,5-dicarbonitrile were dissolved in 1.5 ml of concentrated hydrochloric acid, and 22 mg (0.321 mmol) of sodium nitrite were added. The mixture was stirred initially at 0° C. for one hour and then at room temperature overnight. Purification of the reaction mixture was by preparative HPLC (acetonitrile/water: 10:90→95:5, 0.1% TFA added). This gave 9 mg (17% of theory) of the target compound.

¹H-NMR (400 MHz, DMSO-d₆): δ=9.49 (s, 1H), 8.42 (s, 1H), 7.95 (d, 2H), 7.75 (s, 1H), 7.57 (d, 2H), 4.78 (s, 2H).

LC-MS (Method 2): $R_t$=2.99 min; MS (ESIpos): m/z=486 [M+H]⁺.

Example 12A

2-Chloro-6-({[2-(4-chlorophenyl)-1,3-thiazol-4-yl]methyl}sulfanyl)-4-(1H-pyrazol-3-yl)pyridine-3,5-dicarbonitrile

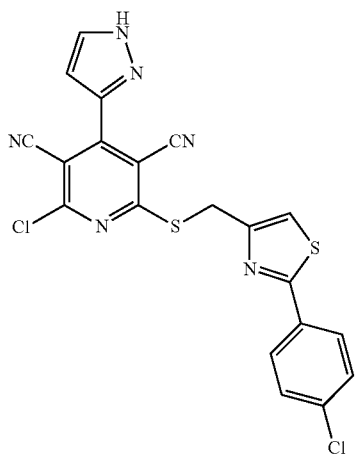 [SMILES: N#Cc1c(Cl)nc(SCc2csc(-c3ccc(Cl)cc3)n2)c(C#N)c1-c1cc[nH]n1]

1.7 g (2.42 mmol) of the compound from Example 5, 567 mg (4.84 mmol) of isopentyl nitrite and 650 mg (4.84 mmol) of copper(II) chloride were initially charged in 24 ml of acetonitrile, and the mixture was stirred at 65° C. for 3 h. 567 mg (4.84 mmol) of isopentyl nitrite and 650 mg (4.84 mmol) of copper(II) chloride were then added, and the reaction mixture was stirred at 65° C. for another 9 h. After cooling to RT, 4.8 ml of 1 N hydrochloric acid were added. The aqueous phase was extracted three times with ethyl acetate. The combined organic phases were washed with saturated aqueous sodium chloride solution and dried over sodium sulfate. After removal of the solvent, the product was purified by preparative HPLC (acetonitrile/water, 0.1% TFA added).

Yield: 370 mg (33% of theory)

LC-MS (Method 3): $R_t$=1.49 min; MS (ESIpos): m/z=469 [M+H]$^+$.

The examples listed in Table 2 were prepared analogously to Example 12A from the appropriate starting materials:

TABLE 2

| Example No. | Structure (yield) | LC-MS: Rt [min] (method); MS (ESI): m/z [M + H]+ |
| --- | --- | --- |
| 13A | (65% of theory) | 2.48 min (Method 1); m/z = 470 |

TABLE 2-continued
| Example No. | Structure (yield) | LC-MS: Rt [min] (method); MS (ESI): m/z [M + H]+ |
| --- | --- | --- |
| 14A | 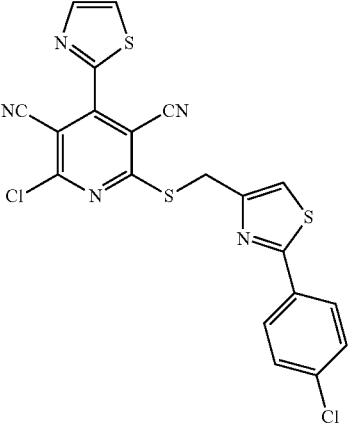 [SMILES: N#Cc1c(Cl)nc(SCc2csc(-c3ccc(Cl)cc3)n2)c(C#N)c1-c1nccs1] (27% of theory) | 1.58 min (Method 3); m/z = 486 |
| 15A | 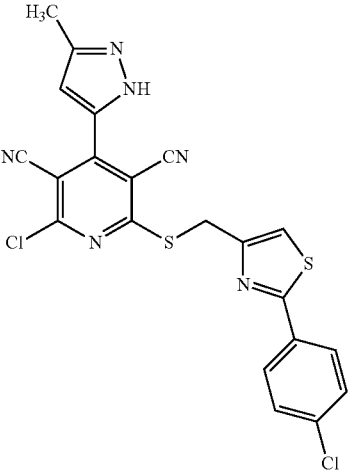 [SMILES: Cc1cc(-c2c(C#N)c(Cl)nc(SCc3csc(-c4ccc(Cl)cc4)n3)c2C#N)[nH]n1] (10% of theory, purity according to LC-MS: about 40%) | 3.03 min (Method 2); m/z = 483 |
| 16A | 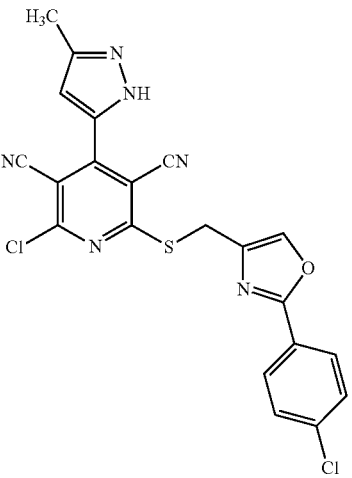 [SMILES: Cc1cc(-c2c(C#N)c(Cl)nc(SCc3coc(-c4ccc(Cl)cc4)n3)c2C#N)[nH]n1] (27% of theory) | 2.89 min (Method 2); m/z = 467 |

TABLE 2-continued

| Example No. | Structure (yield) | LC-MS: Rt [min] (method); MS (ESI): m/z [M + H]+ |
|---|---|---|
| 17A | 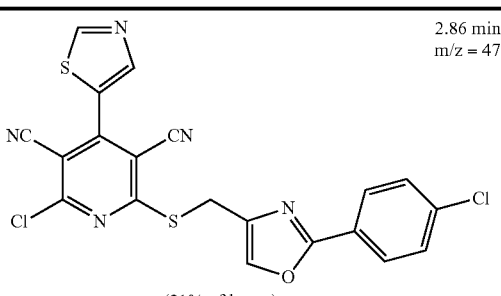 (21% of theory) | 2.86 min (Method 2); m/z = 470 |
| 18A | 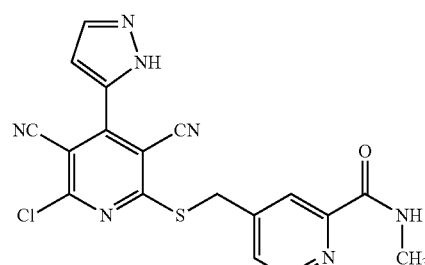 (30% of theory) | 1.00 min (Method 3); m/z = 410 |

Example 19A

Methyl {4-[2-amino-6-({[2-(4-chlorophenyl)-1,3-thiazol-4-yl]methyl}sulfanyl)-3,5-dicyanopyridin-4-yl]-1H-pyrazol-1-yl}acetate

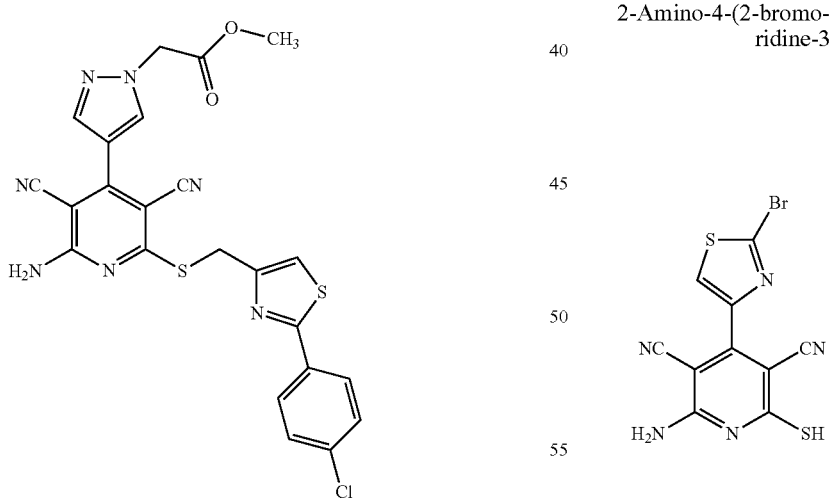

250 mg (0.461 mmol) of the compound from Example 6 were dissolved in 5.1 ml of DMF, 301 mg (0.922 mmol) of cesium carbonate and 71 mg (0.461 mmol) of methyl bromoacetate were added and the mixture was stirred at RT overnight. Water/THF was added in such an amount that a clear solution was formed, and the product was purified directly by preparative HPLC (acetonitrile/water 10:90→95:5, 0.1% TFA added).

Yield: 122 mg (49% of theory)

$^1$H-NMR (400 MHz, DMSO-d$_6$): δ=8.38 (s, 1H), 8.10 (br s, 2H), 7.98-7.7.92 (m, 3H), 7.89 (s, 1H), 7.57 (d, 2H), 5.23 (s, 2H), 4.62 (s, 2H), 3.70 (s, 3H).

LC-MS (Method 2): R$_t$=2.62 min; MS (ESIpos): m/z=522 [M+H]$^+$.

Example 20A

2-Amino-4-(2-bromo-1,3-thiazol-4-yl)-6-sulfanylpyridine-3,5-dicarbonitrile 2 g (10.415 mmol) of 2-bromo-1,3-thiazole-4-carbaldehyde, together with 2.086 g (20.829 mmol) of 2-cyanoethanethioamide and 2.29 ml (20.829 mmol) of 4-methylmorpholine, were heated under reflux in 20 ml of ethanol at 90° C. for 3 h. The reaction mixture was then concentrated. This gave 4.8 g of the target compound in a purity of 73% (yield: 99% of theory)

LC-MS (Method 3): R$_t$=0.83 min; MS (ESIpos): m/z=338 [M+H]$^+$.

Example 21A

2-Amino-4-(2-bromo-1,3-thiazol-4-yl)-6-({[2-(4-chlorophenyl)-1,3-thiazol-4-yl]methyl}sulfanyl)pyridine-3,5-dicarbonitrile

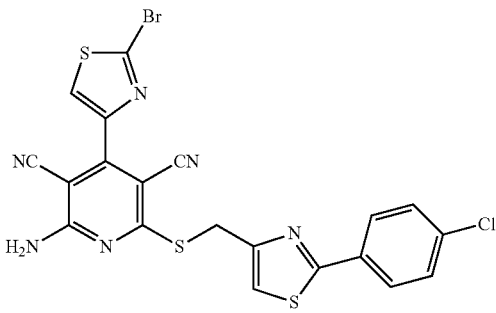 [SMILES: N#Cc1c(N)nc(SCc2csc(-c3ccc(Cl)cc3)n2)c(C#N)c1-c1csc(Br)n1]

4.78 g (purity 77%, 10.882 mmol) of 2-amino-4-(2-bromo-1,3-thiazol-4-yl)-6-sulfanylpyridine-3,5-dicarbonitrile were initially charged in 30 ml of DMF, 2.923 g (11.971 mmol) of 4-(chloromethyl)-2-(4-chlorophenyl)-1,3-thiazole and 2.742 g (32.647 mmol) of sodium bicarbonate were added and the mixture was stirred at room temperature overnight. The reaction mixture was added to water, and the precipitated solid was filtered off with suction, washed with water and dried under high vacuum. The contaminated product was applied to silica gel and purified by chromatography on silica gel (mobile phase: cyclohexane/ethyl acetate 2:1). The product-containing fractions were concentrated, the residue was triturated with dichloromethane and the solid was filtered off, washed with dichloromethane and dried under high vacuum. This gave 1.1 g of the target compound in a purity of 91% (yield: 17% of theory).

LC-MS (Method 3): $R_t$=1.49 min; MS (ESIpos): m/z=545 [M+H]$^+$.

Example 22A

2-Amino-4-[2-(3-{[tert-butyl (dimethyl)silyl]oxy}prop-1-yn-1-yl)-1,3-thiazol-4-yl]-6-({[2-(4-chlorophenyl)-1,3-thiazol-4-yl]methyl}sulfanyl)pyridine-3,5-dicarbonitrile

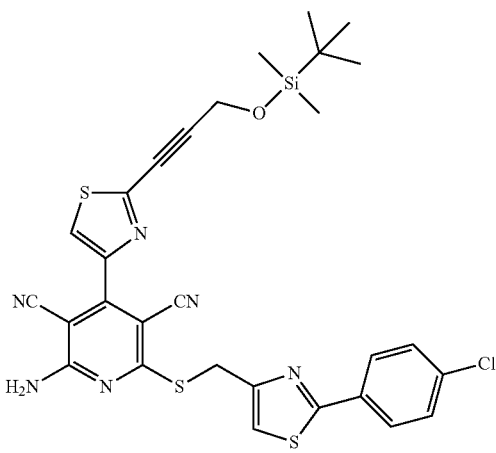 [SMILES: CC(C)(C)[Si](C)(C)OCC#Cc1nc(-c2c(C#N)c(N)nc(SCc3csc(-c4ccc(Cl)cc4)n3)c2C#N)cs1]

Under argon, 500 mg (0.916 mmol) of 2-amino-4-(2-bromo-1,3-thiazol-4-yl)-6-({[2-(4-chlorophenyl)-1,3-thiazol-4-yl]methyl}sulfanyl)pyridine-3,5-dicarbonitrile and 0.186 ml (0.916 mmol) of tert-butyl(dimethyl)(prop-2-yn-1-yloxy)silane were initially charged in 10 ml of acetonitrile, and 105 mg (0.092 mmol) of tetrakis(triphenylphosphine)palladium(0), 35 mg (0.183 mmol) of copper(I) iodide and 0.255 ml (1.832 mmol) of triethylamine were added in succession. The mixture was then heated under reflux at 100° C. for 4 h. The reaction mixture was filtered and the filtrate was purified by preparative HPLC. This gave 239 mg of the target compound in a purity of 38% (yield: 16%). The batch obtained in this manner contained the desilylated compound in a proportion of 62%. The mixture was used without further purification for the subsequent hydrogenation.

LC-MS (Method 7): $R_t$=1.56 min; MS (ESIpos): m/z=635 [M+H]$^+$.

Example 23A

2-Amino-6-({[2-(4-chlorophenyl)-1,3-thiazol-4-yl]methyl}sulfanyl)-4-(2-iodo-1,3-thiazol-5-yl)pyridine-3,5-dicarbonitrile

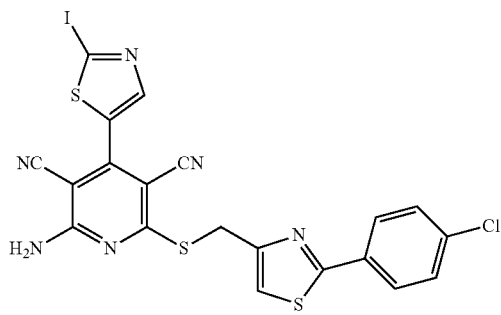 [SMILES: N#Cc1c(N)nc(SCc2csc(-c3ccc(Cl)cc3)n2)c(C#N)c1-c1cnc(I)s1]

Under argon, 230 mg (0.493 mmol) of 2-amino-6-({[2-(4-chlorophenyl)-1,3-thiazol-4-yl]methyl}sulfanyl)-4-(1,3-thiazol-5-yl)pyridine-3,5-dicarbonitrile were dissolved in 15 ml of THF and cooled to −78° C. At this temperature, 1.182 ml (1.182 mmol) of lithium 1,1,1,3,3,3-hexamethyldisilazan-2-ide (1 M in THF) were added dropwise. After 1 h of stirring at −78° C., a solution of 0.143 ml (1.084 mmol) of 1,2-diiodethane in 5 ml of THF was added dropwise, and the reaction mixture was stirred at −78° C. for a further hour. The reaction was terminated by addition of 20 ml of 10% strength aqueous sodium thiosulfate solution. After the mixture had warmed to room temperature, the aqueous phase was extracted three times with dichloromethane. The combined organic phases were dried over sodium sulfate, filtered and concentrated. The residue was purified by preparative HPLC (mobile phase A=water, B=acetonitrile; gradient: 0.0 min 10% B, 30 min 95% B, 34 min 95% B, 34.01 min 10% B, 38 min 10% B; flow rate: 50 ml/min; +0.1% TFA). The solid which had precipitated from the acetonitrile/water mixture was filtered off and dried under high vacuum. This gave 60 mg of the target compound in a purity of 76% (yield: 15% of theory).

LC-MS (Method 7): $R_t$=1.31 min; MS (ESIpos): m/z=593 [M+H]$^+$.

The examples listed in Table 6 were prepared analogously to Example 12A from the appropriate starting materials:

TABLE 6

| Example No. | Structure (yield) | LC-MS: Rt [min] (method); MS (ESI): m/z [M + H]+ |
|---|---|---|
| 24A | 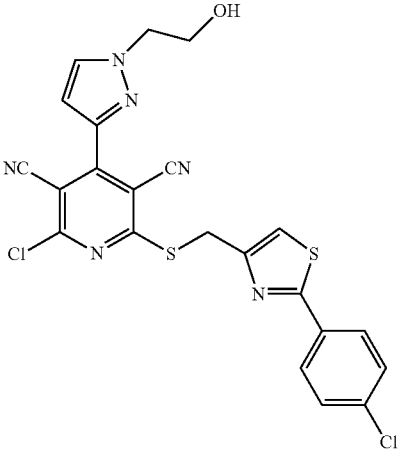 [SMILES: N#Cc1c(Cl)nc(SCc2csc(-c3ccc(Cl)cc3)n2)c(C#N)c1-c1ccn(CCO)n1] (37% of theory) | 2.85 min (Method 2); m/z =513 |

WORKING EXAMPLES

Example 1

2-Amino-6-([2-(4-chlorophenyl)-1,3-thiazol-4-yl]methylsulfanyl)-4-(1,3-thiazol-4-yl)pyridine-3,5-dicarbonitrile

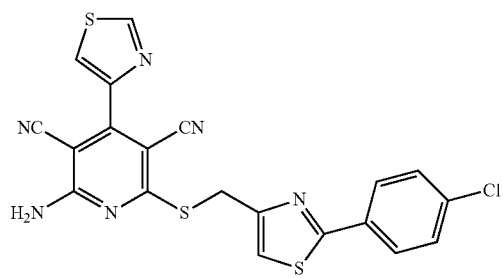 [SMILES: N#Cc1c(N)nc(SCc2coc(-c3ccc(Cl)cc3)n2)c(C#N)c1-c1cscn1]

90 mg (about 0.298 mmol) of 2-amino-6-sulfanyl-4-(1,3-thiazol-4-yl)pyridine-3,5-dicarbonitrile, together with 93 mg (0.382 mmol) of 4-(chloromethyl)-2-(4-chlorophenyl)-1,3-thiazole and 88 mg (1.041 mmol) of sodium bicarbonate, were stirred in 20 ml of DMF at room temperature for 2 h. The reaction mixture was purified twice by preparative HPLC (acetonitrile/water: 10:90→95:5, 0.1% TFA added). This gave 36 mg (22% of theory) of the target compound.

$^1$H-NMR (400 MHz, DMSO-d$_6$): δ=9.33 (d, 1H), 8.38 (d, 1H), 8.22 (br s, 2H), 7.98 (s, 1H), 7.93 (d, 2H), 7.57 (d, 2H), 4.65 (s, 2H).

LC-MS (Method 3): $R_t$=1.35 min; MS (ESIpos): m/z=467 [M+H]$^+$.

Example 2

2-Amino-6-([2-(4-chlorophenyl)-1,3-oxazol-4-yl]methylsulfanyl)-4-(1,3-thiazol-4-yl)pyridine-3,5-dicarbonitrile

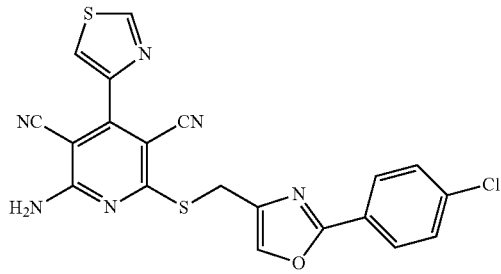

90 mg (about 0.298 mmol) of 2-amino-6-sulfanyl-4-(1,3-thiazol-4-yl)pyridine-3,5-dicarbonitrile, together with 87 mg (0.382 mmol) of 4-(chloromethyl)-2-(4-chlorophenyl)-1,3-oxazole and 88 mg (1.041 mmol) of sodium bicarbonate, were stirred in 20 ml DMF at room temperature overnight. The reaction mixture was purified by preparative HPLC (acetonitrile/water: 10:90→95:5, 0.1% TFA added). This gave 37 mg (24% of theory) of the target compound.

$^1$H-NMR (400 MHz, DMSO-d$_6$): δ=9.33 (d, 1H), 8.37 (d, 1H), 8.36 (s, 1H), 8.13 (br s, 2H), 7.97 (d, 2H), 7.6 (d, 2H), 4.43 (s, 2H).

LC-MS (Method 3): $R_t$=1.29 min; MS (ESIpos): m/z=451 [M+H]$^+$.

Example 3

2-Amino-6-([2-(4-chlorophenyl)-1,3-thiazol-4-yl]methylsulfanyl)-4-(1,3-thiazol-5-yl)pyridine-3,5-dicarbonitrile

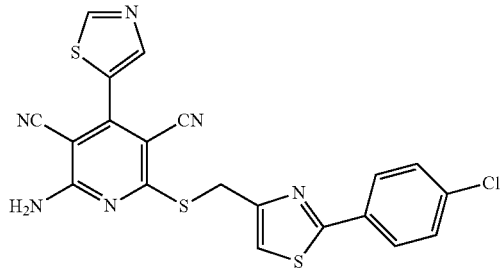 [SMILES: N#Cc1c(N)nc(SCc2coc(-c3ccc(Cl)cc3)n2)c(C#N)c1-c1cncs1]

765 mg (2.950 mmol) of 2-amino-6-sulfanyl-4-(1,3-thiazol-5-yl)pyridine-3,5-dicarbonitrile, together with 792 mg (3.245 mmol) of 4-(chloromethyl)-2-(4-chlorophenyl)-1,3-thiazole and 744 mg (8.850 mmol) of sodium bicarbonate, were stirred in 15 ml DMF at room temperature for 1 h. The reaction mixture was added to 150 ml of acetonitrile, and 100 ml of water were then added. The resulting precipitate was filtered off and washed initially with a little acetonitrile and then with diethyl ether. Drying under reduced pressure gave 889 mg (53% of theory) of the target compound.

$^1$H-NMR (400 MHz, DMSO-d$_6$): δ=9.38 (s, 1H), 8.27 (s, 1H), 8.13 (br s, 2H), 7.95 (d, 2H), 7.89 (s, 1H), 7.57 (d, 2H), 4.62 (s, 2H).

LC-MS (Method 3): R$_t$=1.35 min; MS (ESIpos): m/z=467 [M+H]$^+$.

Example 4

2-Amino-6-([2-(4-chlorophenyl)-1,3-oxazol-4-yl]methylsulfanyl)-4-(1,3-thiazol-5-yl)pyridine-3,5-dicarbonitrile

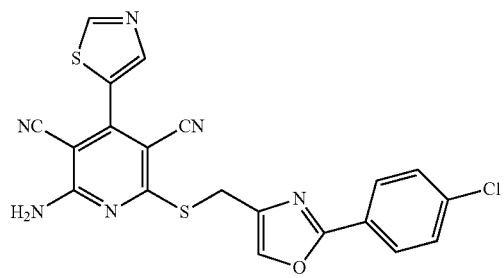

250 mg (0.964 mmol) of 2-amino-6-sulfanyl-4-(1,3-thiazol-5-yl)pyridine-3,5-dicarbonitrile, together with 242 mg (1.060 mmol) of 4-(chloromethyl)-2-(4-chlorophenyl)-1,3-oxazole and 243 mg (2.892 mmol) of sodium bicarbonate, were stirred in 5 ml DMF at room temperature for 1 h. The reaction mixture was added to water, and the resulting precipitate was filtered off and washed with diethyl ether. Drying under reduced pressure gave 53 mg (12% of theory) of the target compound.

$^1$H-NMR (400 MHz, DMSO-d$_6$): δ=9.38 (s, 1H), 8.35 (s, 1H), 8.28 (s, 1H), 8.26 (br s, 2H), 7.96 (d, 2H), 7.59 (d, 2H), 4.42 (s, 2H).

LC-MS (Method 2): R$_t$=2.55 min; MS (ESIpos): m/z=451 [M+H]$^+$.

Example 5

2-Amino-6-({[2-(4-chlorophenyl)-1,3-thiazol-4-yl]methyl}sulfanyl)-4-(1H-pyrazol-3-yl)pyridine-3,5-dicarbonitrile

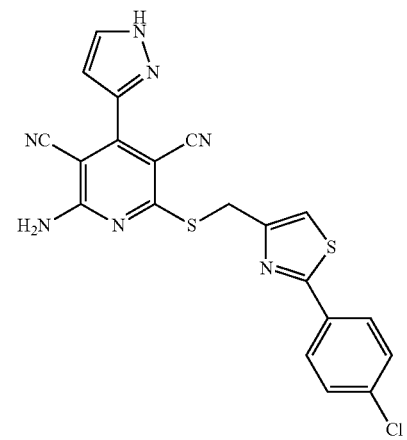 [SMILES: N#Cc1c(N)nc(SCc2csc(-c3ccc(Cl)cc3)n2)c(C#N)c1-c1cc[nH]n1]

50 mg (0.21 mmol) of the compound from Example 6A and 156 mg (0.64 mmol) of 4-(chloromethyl)-2-(4-chlorophenyl)-1,3-thiazole were dissolved in 1 ml of dimethylformamide, 52 mg (0.62 mmol) of sodium bicarbonate were added and the mixture was stirred at RT for 2.5 h. About 10 ml of water were added to the mixture, and the solid formed was purified by preparative HPLC (acetonitrile/water 10:90→95:5, 0.1% TFA added).

Yield: 54 mg (58% of theory)

$^1$H-NMR (400 MHz, DMSO-d$_6$): δ=13.59 (br s, 1H), 8.45-7.80 (m, 6H), 7.57 (d, 2H), 6.79 (t, 1H), 4.63 (s, 2H).

LC-MS (Method 1): R$_t$=2.08 min; MS (ESIpos): m/z=450 [M+H]$^+$.

The examples listed in Table 3 were prepared from the appropriate starting materials analogously to Example 5 with subsequent purification [preparative HPLC (Chromasil, water/acetonitrile+0.15% conc. hydrochloric acid)]:

TABLE 3
| Example No. | Structure (yield) | LC-MS: R_t [min] (method); MS (ESI): m/z [M + H]+ | 1H-NMR (DMSO-d6): |
|---|---|---|---|
| 6 | 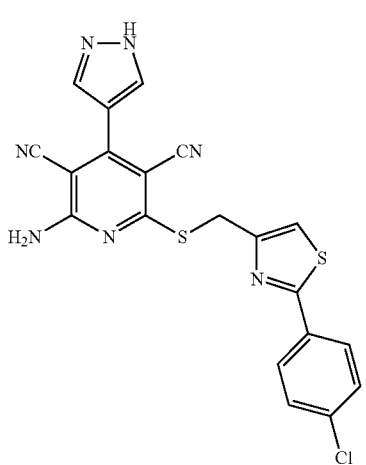 [SMILES: N#Cc1c(N)nc(SCc2csc(-c3ccc(Cl)cc3)n2)c(C#N)c1-c1cn[nH]c1] (66% of theory) | 2.53 min (Method 2); m/z = 450 | δ (400 MHz) = 13.4 (br s, 1H), 8.11 (br s, 4H), 7.93 (d, 2H), 7.89 (s, 1H), 7.57 (d, 2H), 4.62 (s, 2H). |
| 7 | 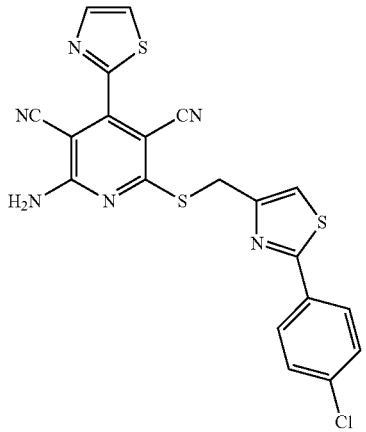 [SMILES: N#Cc1c(N)nc(SCc2csc(-c3ccc(Cl)cc3)n2)c(C#N)c1-c1nccs1] (75% of theory) | 1.38 min (Method 3); m/z = 467 | δ (400 MHz) = 8.40 (br s, 2H), 8.19 (d, 1H), 8.17 (d, 1H), 7.95 (s, 1H), 7.92 (d, 2H), 7.58 (d, 2H), 4.67 (s, 2H). |
| 8 | 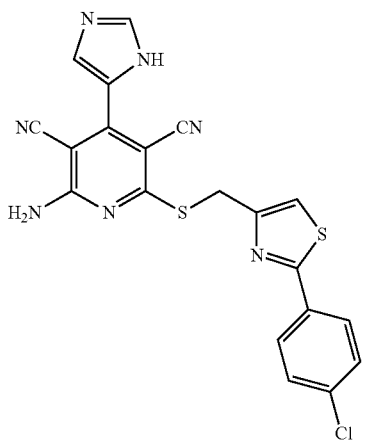 [SMILES: N#Cc1c(N)nc(SCc2csc(-c3ccc(Cl)cc3)n2)c(C#N)c1-c1cnc[nH]1] (31% of theory) | 1.19 min (Method 3); m/z = 450 | δ (400 MHz) = 8.24 (br s, 1H), 8.09 (br s, 2H), 7.97-7.87 (m, 4H), 7.58 (d, 2H), 4.62 (s, 2H). |

TABLE 3-continued
| Example No. | Structure (yield) | LC-MS: R_t [min] (method); MS (ESI): m/z [M + H]+ | 1H-NMR (DMSO-d_6): |
|---|---|---|---|
| 9 | 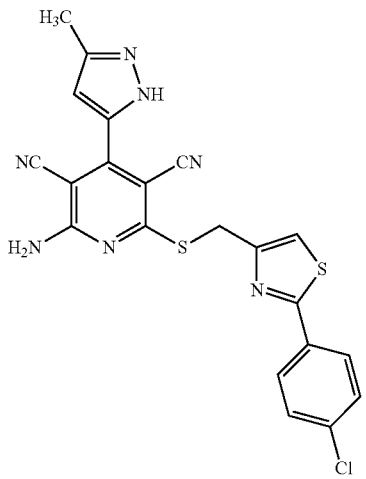 (4% of theory) | 1.31 min (Method 3); m/z = 467 | δ (400 MHz) = 13.29 (br s, 1H), 8.02 (br s, 2H), 7.94 (d, 2H), 7.89 (s, 1H), 7.58 (d, 2H), 6.51 (s, 1H), 4.62 (s, 2H), 2.32 (s, 3H). |
| 10 | 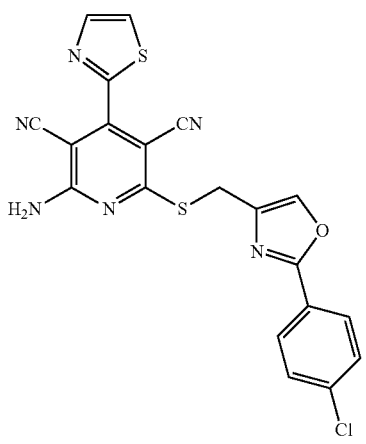 [SMILES: N#Cc1c(N)nc(SCc2coc(-c3ccc(Cl)cc3)n2)c(C#N)c1-c1nccs1] (37% of theory) | 2.63 min (Method 2); m/z = 451 | δ (400 MHz) = 8.37 (s, 1H), 8.25 (br s, 2H), 8.19 (d, 1H), 8.17 (d, 1H), 7.98 (d, 2H), 7.60 (d, 2H), 4.43 (s, 2H). |
| 11 | 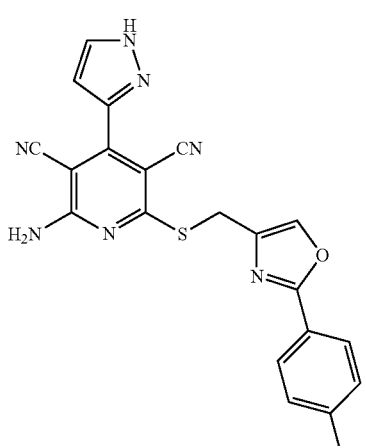 | 1.22 min (Method 3); m/z = 434 | δ (400 MHz) = 13.59 (br s, 1H), 8.36 (s, 1H), 8.09 (br s, 2H), 7.98-7.95 (m, 3H), 7.60 (d, 2H), 6.78 (br s, 1H), 4.41 (s, 2H). |

TABLE 3-continued
| Example No. | Structure (yield) | LC-MS: R_t [min] (method); MS (ESI): m/z [M + H]+ | 1H-NMR (DMSO-d6): |
|---|---|---|---|
| 12 | 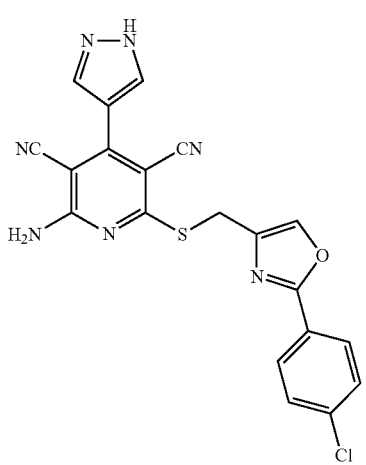 [SMILES: N#Cc1c(N)nc(SCc2coc(-c3ccc(Cl)cc3)n2)c(C#N)c1-c1cn[nH]c1] (72% of theory) | 1.19 min (Method 3); m/z = 434 | δ (400 MHz) = 13.50 (br s, 1H), 8.38-8.23 (m, 2H), 8.08 (br s, 2H), 7.98-7.89 (m, 2H), 7.60 (d, 2H), 4.41 (s, 2H). |
| 13 | 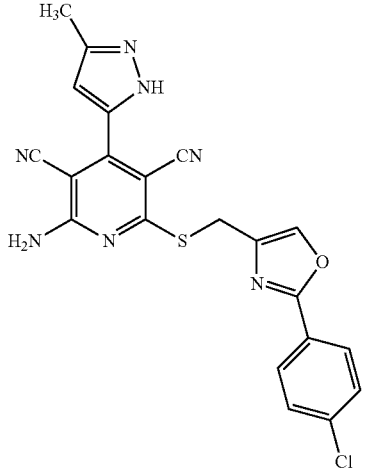 [SMILES: Cc1cc(-c2c(C#N)c(N)nc(SCc3coc(-c4ccc(Cl)cc4)n3)c2C#N)[nH]n1] (71% of theory) | 1.25 min (Method 3); m/z = 448 | δ (400 MHz) = 8.34 (s, 1H), 8.10 (br s, 2H), 7.98 (d, 2H), 7.60 (d, 2H), 6.51 (s, 1H), 4.41 (s, 2H), 2.31 (s, 3H). |
| 14 | 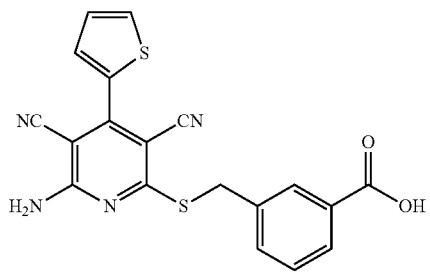 [SMILES: N#Cc1c(N)nc(SCc2cccc(C(=O)O)c2)c(C#N)c1-c1cccs1] (68% of theory) | 2.39 min (Method 2); m/z = 393 | δ (400 MHz) = 13.02 (br s, 1H), 8.19 (br s, 2H), 8.05 (br s, 1H), 7.94 (dd, 1H), 7.82 (t, 2H), 7.55 (dd, 1H), 7.45 (t, 1H), 7.27 (dd, 1H), 4.59 (s, 2H). |

TABLE 3-continued

| Example No. | Structure (yield) | LC-MS: R$_t$ [min] (method); MS (ESI): m/z [M + H]$^+$ | $^1$H-NMR (DMSO-d$_6$): |
|---|---|---|---|
| 15 | (85% of theory) | 1.29 min (Method 1); m/z = 391 | δ (400 MHz) = 13.60 (br s, 1H), 8.76 (q, 1H), 8.54 (d, 1H), 8.12 (s, 1H), 8.05 (br s, 2H), 7.97 (d, 1H), 7.78 (dd, 1H), 6.78 (d, 1H), 4.60 (s, 2H), 2.81 (d, 3H). |

Example 16

2-([2-(4-Chlorophenyl)-1,3-thiazol-4-yl]methylsulfanyl)-6-(3-hydroxyazetidin-1-yl)-4-(1,3-thiazol-5-yl)pyridine-3,5-dicarbonitrile

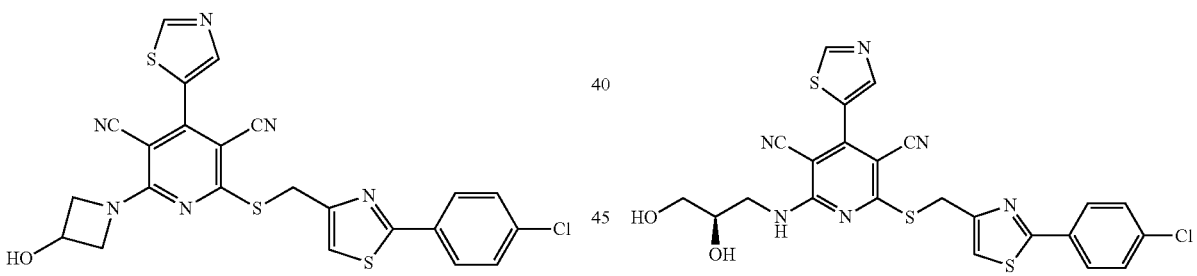

100 mg (0.206 mmol) of 2-chloro-6-({[2-(4-chlorophenyl)-1,3-thiazol-4-yl]methyl}sulfanyl)-4-(1,3-thiazol-5-yl)pyridine-3,5-dicarbonitrile, together with 45 mg (0.411 mmol) of azetidin-3-ol hydrochloride and 53 mg (0.411 mmol) of N-ethyl-N-(1-methylethyl)propan-2-amine, were dissolved in 1.5 ml of THF. The mixture was stirred at room temperature for two hours, and the product was then purified by preparative HPLC (acetonitrile/water: 10:90→95:5, 0.1% TFA added). This gave 40 mg (37% of theory) of the target compound.

$^1$H-NMR (400 MHz, DMSO-d$_6$): δ=9.40 (d, 1H), 8.28 (d, 1H), 7.95 (d, 2H), 7.68 (s, 1H), 7.57 (d, 2H), 5.9 (d, 1H), 4.80-4.67 (m, 3H), 4.62-4.55 (m, 2H), 4.17-4.11 (m, 2H).

LC-MS (Method 2): R$_t$=2.66 min; MS (ESIpos): m/z=523 [M+H]$^+$.

Example 17

2-([2-(4-Chlorophenyl)-1,3-thiazol-4-yl]methylsulfanyl)-6-[(2R)-2,3-dihydroxypropyl]amino-4-(1,3-thiazol-5-yl)pyridine-3,5-dicarbonitrile 100 mg (0.206 mmol) of 2-chloro-6-({[2-(4-chlorophenyl)-1,3-thiazol-4-yl]methyl}sulfanyl)-4-(1,3-thiazol-5-yl)pyridine-3,5-dicarbonitrile, together with 38 mg (0.411 mmol) of (2R)-3-aminopropane-1,2-diol, were dissolved in 1.5 ml of THF. The mixture was stirred at room temperature for two hours, and the product was then purified by preparative HPLC (acetonitrile/water: 10:90→95:5, 0.1% TFA added). This gave 64 mg (58%/0 of theory) of the target compound.

$^1$H-NMR (500 MHz, DMSO-d$_6$): δ=9.41 (d, 1H), 8.31 (d, 1H), 8.10 (t, 1H), 7.96 (d, 2H), 7.73 (s, 1H), 7.57 (d, 2H), 4.92 (d, 1H), 4.78-4.68 (m, 3H), 3.81-3.71 (m, 2H), 3.58-3.48 (m, 1H), 3.44-3.40 (m, 2H).

LC-MS (Method 2): R$_t$=2.42 min; MS (ESIpos): m/z=541 [M+H]$^+$.

Example 18

2-([2-(4-Chlorophenyl)-1,3-oxazol-4-yl]methylsulfanyl)-6-(3-hydroxyazetidin-1-yl)-4-(1,3-thiazol-5-yl)pyridine-3,5-dicarbonitrile

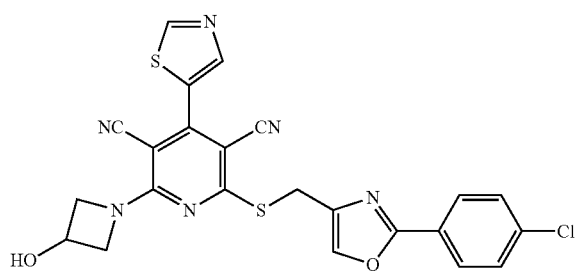 [SMILES: N#Cc1c(SCc2coc(-c3ccc(Cl)cc3)n2)nc(N2CC(O)C2)c(C#N)c1-c1cncs1]

80 mg (0.170 mmol) of 2-chloro-6-({[2-(4-chlorophenyl)-1,3-oxazol-4-yl]methyl}sulfanyl)-4-(1,3-thiazol-5-yl)pyridine-3,5-dicarbonitrile, together with 37 mg (0.340 mmol) of azetidin-3-ol hydrochloride and 44 mg (0.340 mmol) of N-ethyl-N-(1-methylethyl)propan-2-amine, were dissolved in 1 ml of THF. The mixture was stirred at room temperature for two hours, and the product was then purified by preparative HPLC (acetonitrile/water: 10:90→95:5, 0.1% TFA added). This gave 40 mg (46% of theory) of the target compound.

$^1$H-NMR (400 MHz, DMSO-d$_6$): δ=9.40 (s, 1H), 8.27 (s, 1H), 8.16 (s, 1H), 7.97 (d, 2H), 7.61 (d, 2H), 5.92 (br s, 1H), 4.68-4.60 (m, 3H), 4.48 (s, 2H), 4.18 (m, 2H).

LC-MS (Method 2): R$_t$=2.54 min; MS (ESIpos): m/z=507 [M+H]$^+$.

Example 19

2-({[2-(4-Chlorophenyl)-1,3-oxazol-4-yl]methyl}sulfanyl)-6-[(2-hydroxyethyl)amino]-4-(1,3-thiazol-2-yl)pyridine-3,5-dicarbonitrile

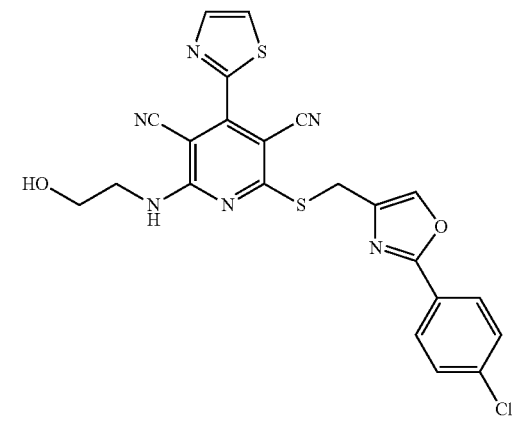 [SMILES: N#Cc1c(NCCO)nc(SCc2coc(-c3ccc(Cl)cc3)n2)c(C#N)c1-c1nccs1]

50 mg (0.11 mmol) of the compound from Example 13A were dissolved in 1.5 ml of DMF, 13 mg (0.213 mmol) of 2-aminoethanol were added and the mixture was stirred overnight at RT. The reaction was purified by preparative HPLC (acetonitrile/water 10:90→95:5).

Yield: 23 mg (43% of theory)

$^1$H-NMR (400 MHz, DMSO-d$_6$): δ=8.25-8.17 (m, 3H), 7.98 (d, 2H), 7.61 (d, 2H), 4.83 (t, 1H), 4.52 (s, 2H), 3.69-3.62 (m, 2H), 3.61-3.53 (m, 2H).

LC-MS (Method 1): Rt=2.05 min; MS (ESIpos): m/z=495 [M+H]$^+$.

The examples listed in Table 4 were prepared from the appropriate starting materials analogously to Example 19 with subsequent purification [preparative HPLC (Chromasil, water/acetonitrile, if appropriate with added acid)]:

TABLE 4

| Example No. | Structure (yield) | LC-MS: R$_t$ [min] (method); MS (ESI): m/z [M + H]$^+$ | $^1$H-NMR (DMSO-d$_6$): |
|---|---|---|---|
| 20 | (35% of theory) | 2.10 min (Method 1); m/z = 507 | δ (400 MHz) = 8.22-8.15 (m, 3H), 7.98 (d, 2H), 7.61 (d, 2H), 5.89 (br s, 1H), 4.70 (br s, 2H), 4.62 (br s, 1H), 4.49 (s, 2H), 4.19 (br s, 2H). |

TABLE 4-continued
| Example No. | Structure (yield) | LC-MS: R$_t$ [min] (method); MS (ESI): m/z [M + H]$^+$ | $^1$H-NMR (DMSO-d$_6$): |
|---|---|---|---|
| 21 | 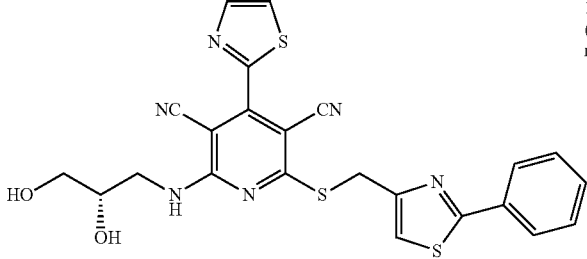 [SMILES: N#Cc1c(NC[C@H](O)CO)nc(SCc2csc(-c3ccccc3)n2)c(C#N)c1-c1nccs1]<br>(90% of theory) | 1.26 min (Method 3); m/z = 541 | δ (400 MHz) = 8.19 (dd, 2H), 8.09 (t, 1H), 7.97 (d, 2H), 7.73 (s, 1H), 7.56 (d, 2H), 4.96 (d, 1H), 4.80-4.69 (m, 3H), 3.81-3.70 (m, 2H), 3.58-3.46 (m, 1H), 3.45-3.34 (m, 2H). |
| 22 | 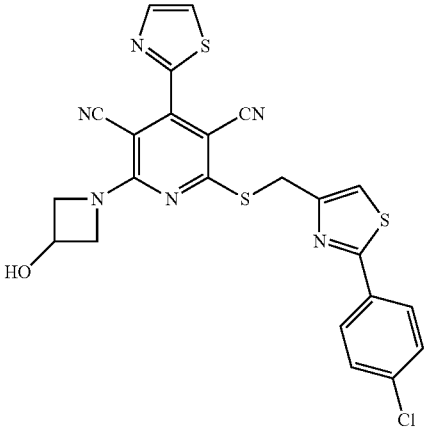 [SMILES: N#Cc1c(SCc2csc(-c3ccc(Cl)cc3)n2)nc(N2CC(O)C2)c(C#N)c1-c1nccs1]<br>(88% of theory) | 1.37 min (Method 3); m/z = 523 | δ (400 MHz) = 8.19 (dd, 2H), 7.95 (d, 2H), 7.69 (s, 1H), 7.58 (d, 2H), 5.89 (d, 1H), 4.80-4.55 (m, 5H), 4.19 (br s, 2H). |
| 23 | 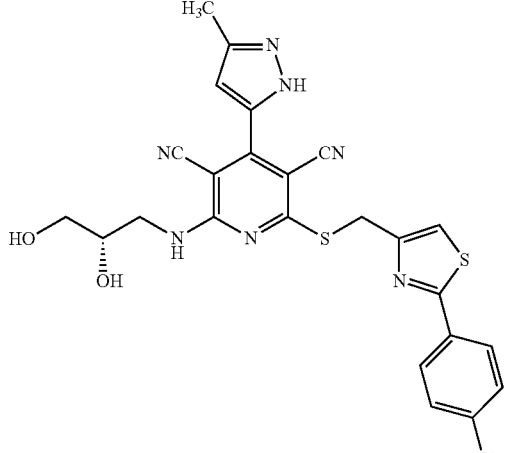<br>(95% of theory) | 1.22 min (Method 3); m/z = 538 | δ (400 MHz) = 13.30 (br s, 1H), 7.97 (d, 2H), 7.79-7.70 (m, 2H), 7.58 (d, 2H), 6.52 (s, 1H), 4.71 (dd, 2H), 4.62 (s, 2H), 2.32 (s, 3H) 3.90-3.62 (m, 4H), 3.53-3.45 (m, 1H), 3.43-3.31 (m, 2H), 2.32 (s, 3H). |

TABLE 4-continued
| Example No. | Structure (yield) | LC-MS: R_t [min] (method); MS (ESI): m/z [M + H]+ | 1H-NMR (DMSO-d_6): |
|---|---|---|---|
| 24 | 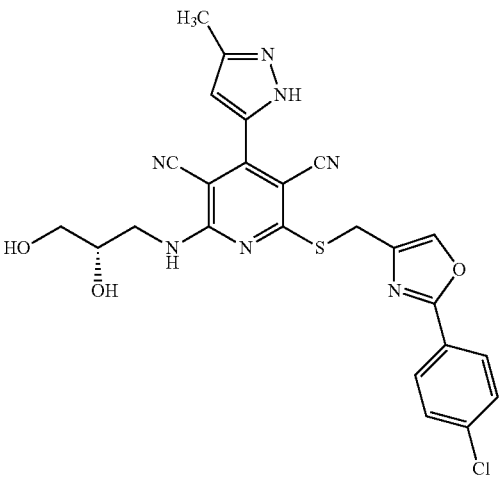 [SMILES: Cc1cc(-c2c(C#N)c(NC[C@H](O)CO)nc(SCc3coc(-c4ccc(Cl)cc4)n3)c2C#N)[nH]n1]<br>(90% of theory) | 1.17 min (Method 3); m/z = 522 | δ (400 MHz) = 13.29 (br s, 1H), 8.20 (s, 1H), 7.98 (d, 2H), 7.79-7.70 (m, 1H), 7.61 (d, 2H), 6.52 (s, 1H), 4.94 (br s, 1H), 4.72 (br s, 1H), 4.52 (dd, 2H), 3.70-3.68 (m, 2H), 3.57-3.47 (m, 1H), 3.43-3.30 (m, 2H), 2.32 (s, 3H). |
| 25 | 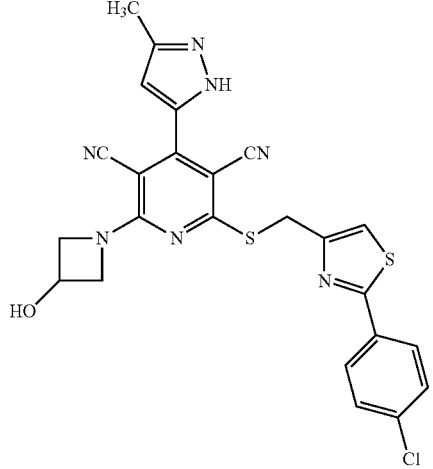 [SMILES: Cc1cc(-c2c(C#N)c(SCc3csc(-c4ccc(Cl)cc4)n3)nc(N3CC(O)C3)c2C#N)[nH]n1]<br>(37% of theory) | 1.31 min (Method 3); m/z = 520 | δ (400 MHz) = 13.28 (s, 1H), 7.96 (d, 2H), 7.68 (s, 1H), 7.57 (d, 2H), 6.48 (s, 1H), 5.84 (br s, 1H), 4.71-4.52 (m, 5H), 4.12 (br s, 2H), 2.30 (s, 3H). |
| 26 | 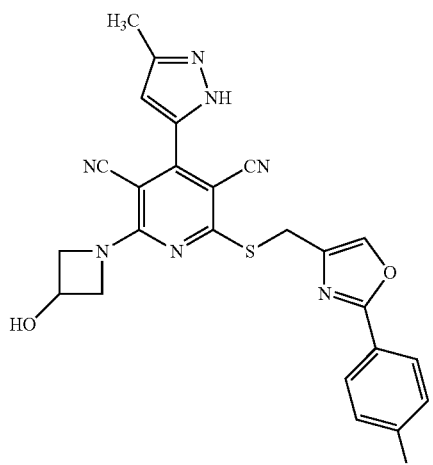<br>(34% of theory) | 1.25 min (Method 3); m/z = 504 | δ (400 MHz) = 13.28 (s, 1H), 8.18 (s, 1H), 7.98 (d, 2H), 7.61 (d, 2H), 6.46 (s, 1H), 5.84 (d, 1H), 4.72-4.52 (m, 3H), 4.48 (s, 2H), 4.14 (d, 2H), 2.31 (s, 3H). |

TABLE 4-continued
| Example No. | Structure (yield) | LC-MS: $R_t$ [min] (method); MS (ESI): m/z [M + H]+ | 1H-NMR (DMSO-$d_6$): |
|---|---|---|---|
| 27 | 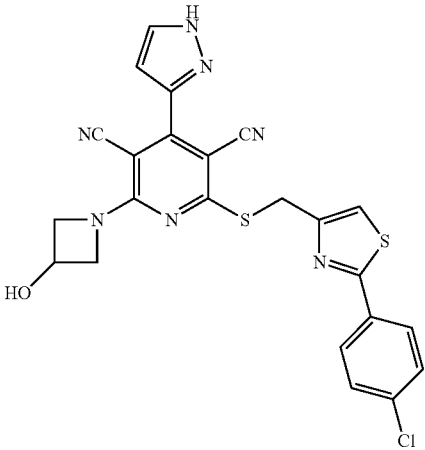 [SMILES: N#Cc1c(SCc2csc(-c3ccc(Cl)cc3)n2)nc(N2CC(O)C2)c(C#N)c1-c1cc[nH]n1] (23% of theory) | 2.05 min (Method 3); m/z = 506 | δ (400 MHz) = 13.59 (br s, 1H), 7.99-7.92 (m, 3H), 7.68 (s, 1H), 7.58 (d, 2H), 6.75 (s, 1H), 5.87 (d, 1H), 4.72-4.53 (m, 5H), 4.15 (d, 2H). |
| 28 | 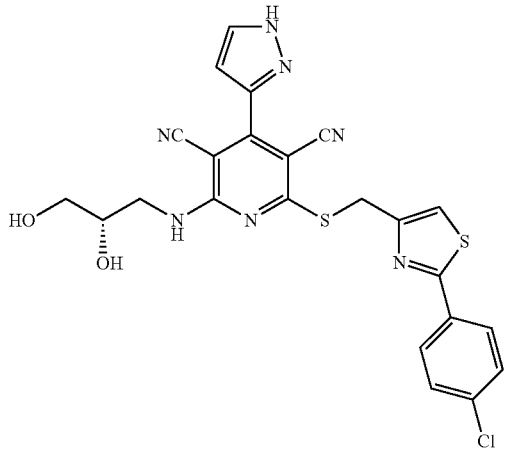 [SMILES: N#Cc1c(NC[C@H](O)CO)nc(SCc2csc(-c3ccc(Cl)cc3)n2)c(C#N)c1-c1cc[nH]n1] (72% of theory) | 1.18 min (Method 3); m/z = 524 | δ (400 MHz) = 13.61 (br s, 1H), 7.99-7.92 (m, 3H), 7.83-7.77 (m, 1H), 7.73 (s, 1H), 7.57 (d, 2H), 6.79 (d, 1H), 4.71 (dd, 2H), 3.90-3.62 (m, 4H), 3.55-3.47 (m, 1H), 3.43-3.32 (m, 2H). |
| 29 | 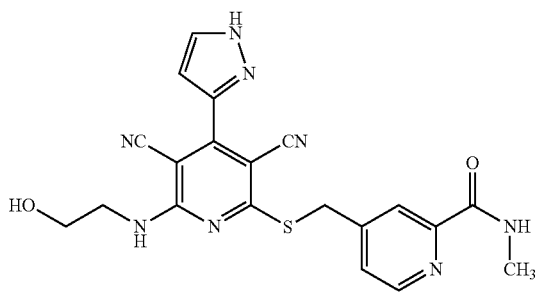 [SMILES: CNC(=O)c1cc(CSc2nc(NCCO)c(C#N)c(-c3cc[nH]n3)c2C#N)ccn1] (55% of theory) | 0.84 min (Method 3); m/z = 435 | δ (400 MHz) = 13.60 (br s, 1H), 8.79 (q, 1H), 8.58 (d, 1H), 8.12 (s, 1H), 7.98 (s, 1H), 7.91-7.83 (m, 1H), 7.64 (dd, 1H), 6.79 (d, 1H), 4.64 (s, 2H), 3.53-3.41 (m, 4H), 2.82 (d, 3H). |

Example 30

2-Amino-6-([2-(4-chlorophenyl)-1,3-thiazol-4-yl]methylsulfanyl)-4-[1-(2-hydroxypropyl)-1H-pyrazol-3-yl]pyridine-3,5-dicarbonitrile

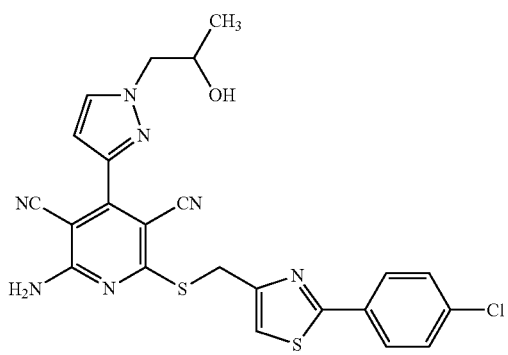 [SMILES: CC(O)Cn1ccc(-c2c(C#N)c(N)nc(SCc3csc(-c4ccc(Cl)cc4)n3)c2C#N)n1]

10 mg (0.022 mmol) of 2-amino-6-({[2-(4-chlorophenyl)-1,3-thiazol-4-yl]methyl}sulfanyl)-4-(1H-pyrazol-3-yl)pyridine-3,5-dicarbonitrile were dissolved in 1 ml of 2-methyloxirane, and a spatula tip of cesium carbonate was added. The reaction mixture was stirred at room temperature overnight, concentrated, taken up in a little methanol and purified by preparative HPLC (acetonitrile/water: 10:90→95:5, 0.1% TFA added). This gave 10 mg (86% of theory) of the target compound.

$^1$H-NMR (400 MHz, DMSO-$d_6$): δ=8.26 (br s, 2H), 7.95 (d, 2H), 7.88 (d, 1H), 7.71 (s, 1H), 7.56 (d, 2H), 6.74 (d, 1H), 4.62 (s, 2H), 4.13 (d, 2H), 4.05-3.99 (m, 1H), 1.04 (d, 3H), 3.37 (d, 2H).

LC-MS (Method 2): $R_t$=2.58 min; MS (ESIpos): m/z=508 [M+H]$^+$.

Example 31

2-Amino-6-({[2-(4-chlorophenyl)-1,3-thiazol-4-yl]methyl}sulfanyl)-4-[1-(2-hydroxyethyl)-1H-pyrazol-3-yl]pyridine-3,5-dicarbonitrile

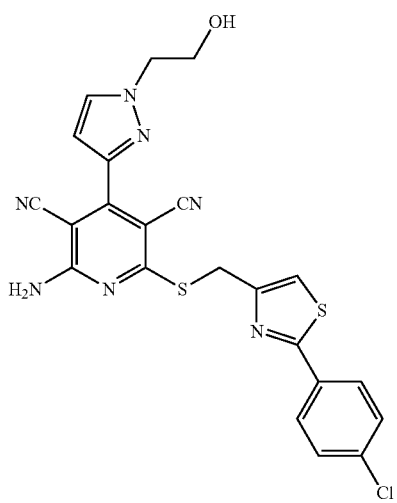 [SMILES: N#Cc1c(N)nc(SCc2csc(-c3ccc(Cl)cc3)n2)c(C#N)c1-c1ccn(CCO)n1]

100 mg (0.18 mmol) of the compound from Example 5 were dissolved in 1.5 ml of DMF, 90 mg (0.28 mmol) of cesium carbonate and 158 mg (0.92 mmol) of iodoethanol were added and the mixture was stirred at 80° C. overnight. Another 90 mg (0.28 mmol) of cesium carbonate were then added, and the reaction mixture was stirred at 80° C. for another 4 h. A little water and THF were added to the reaction such that a clear solution was formed, and the product was purified by preparative HPLC (acetonitrile/water 10:90→95:5, 0.1% TFA added).

Yield: 41 mg (40% of theory)

$^1$H-NMR (400 MHz, DMSO-$d_6$): δ=8.05 (br s, 2H), 7.96-7.88 (m, 4H), 7.57 (d, 2H), 6.77 (d, 1H), 4.62 (s, 2H), 4.23 (t, 2H), 3.78 (t, 2H).

LC-MS (Method 1): $R_t$=2.05 min; MS (ESIpos): m/z=494 [M+H]$^+$.

Example 32

2-Amino-6-({[2-(4-chlorophenyl)-1,3-thiazol-4-yl]methyl}sulfanyl)-4-thiophen-2-ylpyridine-3,5-dicarbonitrile

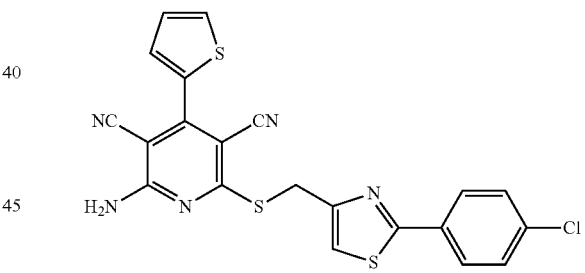

70 mg (0.271 mmol) of 2-amino-6-sulfanyl-4-thiophen-2-ylpyridine-3,5-dicarbonitrile, together with 79 mg (0.325 mmol) of 4-(chloromethyl)-2-(4-chlorophenyl)-1,3-thiazole and 91 mg (1.084 mmol) of sodium bicarbonate, were stirred in 2 ml DMF at room temperature overnight. The reaction mixture was filtered and the filtrate was purified by preparative HPLC (Chromasil, water/acetonitrile—without acid). This gave 94 mg (71% of theory) of the target compound.

¹H-NMR (400 MHz, DMSO-d₆): δ=8.15 (br s, 2H), 7.96-7.91 (m, 4H), 7.58-7.55 (m, 3H), 7.27 (dd, 1H), 3.33 (s, 2H).
LC-MS (Method 4): R$_t$=2.79 min; MS (ESIpos): m/z=466 [M+H]⁺.

Example 33

2-Amino-6-({[2-(4-chlorophenyl)-1,3-thiazol-4-yl]methyl}sulfanyl)-4-[1-(3-hydroxypropyl)-1H-pyrazol-3-yl]pyridine-3,5-dicarbonitrile

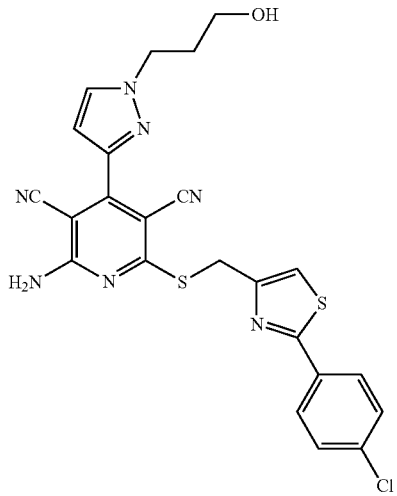 [SMILES: N#Cc1c(N)nc(SCc2csc(-c3ccc(Cl)cc3)n2)c(C#N)c1-c1ccn(CCCO)n1]

50 mg (0.092 mmol) of the compound from Example 5 were dissolved in 0.8 ml of DMF, 15 mg (0.101 mmol) of DBU and 21 mg (0.111 mmol) of 3-iodopropanol were added and the mixture was stirred at 120° C. overnight. A little water and ethyl acetate were added to the mixture, and the two phases formed were separated. The aqueous phase was extracted twice with ethyl acetate. The combined organic phases were concentrated on a rotary evaporator and the residue was purified by thick-layer chromatography (toluene:acetonitrile=3:1).

Yield: 18 mg (38% of theory)

¹H-NMR (400 MHz, DMSO-d₆): δ=8.10 (br s, 2H), 7.96-7.90 (m, 4H), 7.57 (d, 2H), 6.74 (d, 1H), 4.62 (s, 2H), 4.60 (t, 1H), 4.26 (t, 2H), 3.40 (q, 2H), 1.96 (Quintett, 2H).

LC-MS (Method 2): R$_t$=2.54 min; MS (ESIpos): m/z=508 [M+H]⁺.

The examples listed in Table 5 were prepared from the appropriate starting materials analogously to Example 33 with subsequent purification [preparative HPLC (Chromasil, water/acetonitrile, if appropriate with added acid)]:

TABLE 5

| Example No. | Structure (yield) | LC-MS: R$_t$ [min] (method); MS (ESI): m/z [M + H]⁺ | ¹H-NMR (DMSO-d₆): |
|---|---|---|---|
| 34 | (77% of theory) | 2.01 min (Method 1); m/z = 508 | δ (400 MHz) = 8.31 (s, 1H), 8.09 (br s, 2H), 7.95 (d, 2H), 7.90 (d, 2H), 7.58 (d, 2H), 4.62 (s, 2H), 4.28 (t, 2H), 3.41 (t, 2H), 1.94 (quintett, 2H). |

TABLE 5-continued

| Example No. | Structure (yield) | LC-MS: $R_t$ [min] (method); MS (ESI): m/z [M + H]$^+$ | $^1$H-NMR (DMSO-d$_6$): |
|---|---|---|---|
| 35 | 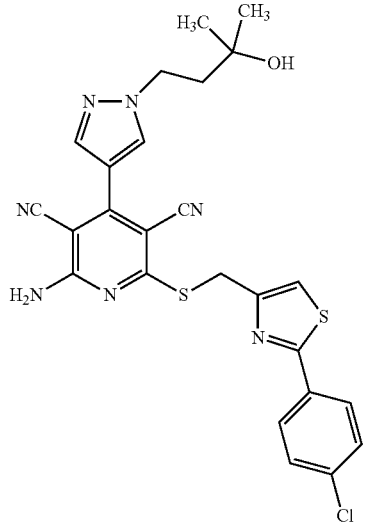 [SMILES: CC(C)(O)CCn1cc(-c2c(C#N)c(N)nc(SCc3csc(-c4ccc(Cl)cc4)n3)c2C#N)cn1]<br>(28% of theory) | 2.14 min (Method 1); m/z = 536 | δ (400 MHz) = 8.32 (s, 1H), 8.09 (br s, 2H), 7.95 (d, 2H), 7.90 (s, 2H), 7.58 (d, 2H), 4.62 (s, 2H), 4.49 (s, 1H), 4.29 (t, 2H), 1.92 (t, 2H). |

Example 36

2-Amino-6-({[2-(4-chlorophenyl)-1,3-thiazol-4-yl]methyl}sulfanyl)-4-[1-(2-hydroxyethyl)-1H-pyrazol-4-yl]pyridine-3,5-dicarbonitrile

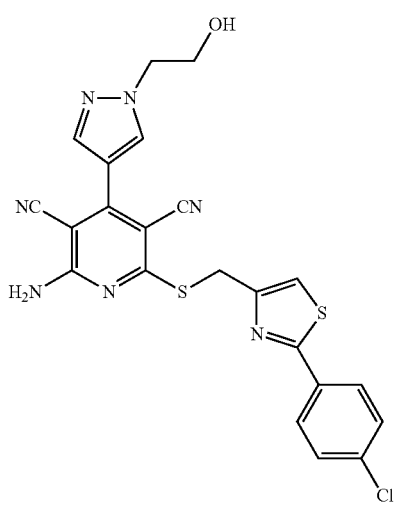 [SMILES: N#Cc1c(N)nc(SCc2csc(-c3ccc(Cl)cc3)n2)c(C#N)c1-c1cnn(CCO)c1]

80 mg (0.153 mmol) of the compound from Example 19A were initially charged in 3 ml of methanol and 3 ml of THF, and 17 mg (0.460 mmol) of sodium borohydride were added. The reaction mixture was stirred at RT for 1 h, another 17 mg (0.460 mmol) of sodium borohydride were then added and the mixture was stirred at RT for 1 h. A little water was added to the reaction, and the product was purified directly by preparative HPLC (acetonitrile/water 10:90→95:5, 0.1% TFA added).

Yield: 70 mg (92% of theory)

$^1$H-NMR (400 MHz, DMSO-d$_6$): δ=8.30 (s, 1H), 8.09 (br s, 2H), 7.97-7.91 (m, 3H), 7.89 (s, 1H), 7.57 (d, 2H), 4.62 (s, 2H), 4.26 (t, 2H), 3.76 (t, 2H).

LC-MS (Method 2): $R_t$=2.40 min; MS (ESIpos): m/z=494 [M+H]$^+$.

Example 37

3-({[6-Amino-3,5-dicyano-4-(2-thienyl)pyridin-2-yl]thio}methyl)benzamide

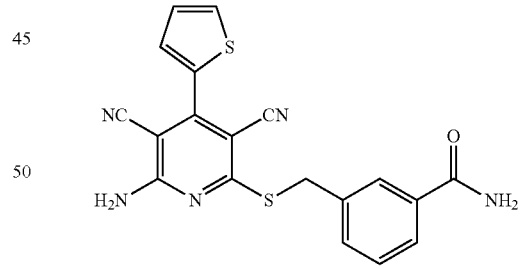

48 mg (0.122 mmol) of the compound from Example 14 were initially charged in 2 ml of DMF, 35 mg (0.183 mmol) of 1-(3-dimethylaminopropyl)-3-ethylcarbodiimide hydrochloride and 25 mg (0.183 mmol) of 1-hydroxy-1H-benzotriazole hydrate were added and the mixture was stirred at RT for 10 min. 33 mg (0.612 mmol) of ammonium chloride and 110 mg (0.856 mmol) of N,N-diisopropylethylamine were then added, and the reaction was stirred at RT overnight. A little water was added to the reaction mixture, and the product was purified directly by preparative HPLC (acetonitrile/water 10:90→95:5, 0.1% TFA added).

Yield: 37 mg (77% of theory)

¹H-NMR (400 MHz, DMSO-d₆): δ=8.12 (br s, 2H), 8.00-8.90 (m, 3H), 7.78 (d, 1H), 7.69 (d, 1H), 7.55 (dd, 1H), 7.43-7.36 (m, 2H), 7.28 (dd, 1H), 4.55 (s, 2H).

LC-MS (Method 6): $R_t$=1.88 min; MS (ESIpos): m/z=392 [M+H]⁺.

Example 38

2-({[2-(4-Chlorophenyl)-1,3-thiazol-4-yl]methyl}sulfanyl)-6-(methylamino)-4-(1H-pyrazol-3-yl)pyridine-3,5-dicarbonitrile

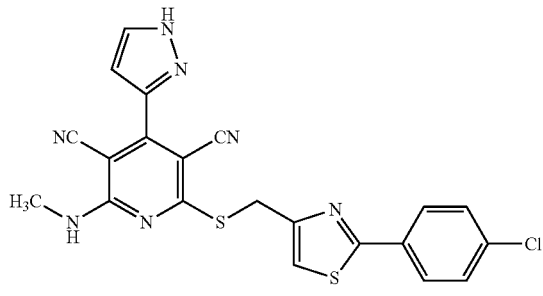 [SMILES: CNc1nc(SCc2csc(-c3ccc(Cl)cc3)n2)c(C#N)c(-c2cc[nH]n2)c1C#N]

300 mg (0.639 mmol) of 2-chloro-6-({[2-(4-chlorophenyl)-1,3-thiazol-4-yl]methyl}sulfanyl)-4-(1H-pyrazol-3-yl)pyridine-3,5-dicarbonitrile were dissolved in 2 ml of tetrahydrofuran, and 0.639 ml (1.278 mmol) of a 2 M solution of methylamine in tetrahydrofuran was added. After 30 minutes of stirring, methanol was added, the mixture was filtered and the filtrate was purified by preparative HPLC. This gave 173 mg (58% of theory) of the target compound.

¹H-NMR (400 MHz, DMSO-d₆): δ=13.59 (s, 1H), 8.08 (m, 1H), 7.98 (d, 1H), 7.95 (d, 2H), 7.69 (s, 1H), 7.57 (d, 2H), 6.79 (d, 1H), 4.72 (s, 2H), 3.01 (s, 3H).

LC-MS (Method 3): $R_t$=1.42 min; MS (ESIpos): m/z=464 [M+H]⁺.

Example 39

2-({[2-(4-Chlorophenyl)-1,3-thiazol-4-yl]methyl}sulfanyl)-6-[(2-hydroxyethyl)amino]-4-(1H-pyrazol-3-yl)pyridine-3,5-dicarbonitrile

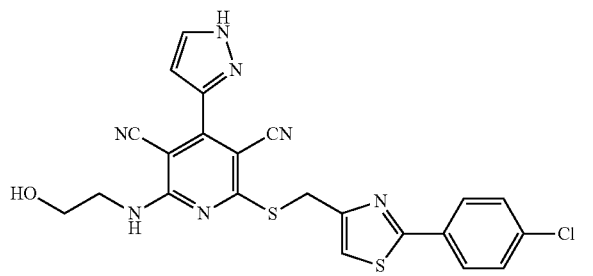 [SMILES: N#Cc1c(NCCO)nc(SCc2csc(-c3ccc(Cl)cc3)n2)c(C#N)c1-c1cc[nH]n1]

58 mg (0.124 mmol) of 2-chloro-6-({[2-(4-chlorophenyl)-1,3-thiazol-4-yl]methyl}sulfanyl)-4-(1H-pyrazol-3-yl)pyridine-3,5-dicarbonitrile were dissolved in 1 ml of tetrahydrofuran, and 15 mg (0.247 mmol) of 2-aminoethanol were added. After 30 minutes of stirring, methanol was added, the mixture was filtered and the filtrate was purified by preparative HPLC. This gave 63 mg (100% of theory) of the target compound.

¹H-NMR (400 MHz, DMSO-d₆): δ=13.60 (s, 1H), 7.99 (m, 1H), 7.96 (d, 2H), 7.91 (m, 1H), 7.71 (s, 1H), 7.57 (d, 2H), 6.78 (d, 1H), 4.80 (t, 1H), 4.70 (s, 2H), 3.60 (m, 2H), 3.54 (m, 2H).

LC-MS (Method 2): $R_t$=2.45 min; MS (ESIpos): m/z=494 [M+H]⁺.

Example 40

2-({[2-(4-Chlorophenyl)-1,3-thiazol-4-yl]methyl}sulfanyl)-6-[(2-hydroxyethyl)amino]-4-(1,3-thiazol-5-yl)pyridine-3,5-dicarbonitrile

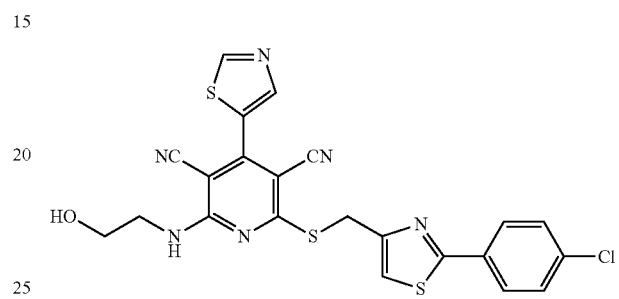

100 mg (purity 91%, 0.186 mmol) of 2-chloro-6-({[2-(4-chlorophenyl)-1,3-thiazol-4-yl]methyl}sulfanyl)-4-(1,3-thiazol-5-yl)pyridine-3,5-dicarbonitrile were initially charged in 5 ml of THF, 0.023 ml (0.373 mmol) of 2-aminoethanol was added and the mixture was stirred at room temperature for 30 min. The product was then isolated by preparative HPLC. This gave 64 mg (67% of theory) of the target compound.

¹H-NMR (400 MHz, DMSO-d₆): 9.41 (s, 1H), 8.31 (s, 1H), 8.20 (t, 1H), 7.93 (d, 2H), 7.71 (s, 1H), 7.57 (d, 2H), 4.81 (m, 1H), 4.71 (s, 2H), 3.61 (m, 2H), 3.53 (m, 2H).

LC-MS (Method 3): $R_t$=1.33 min; MS (ESIpos): m/z=511 [M+H]⁺.

Example 41

2-Amino-6-({[2-(4-chlorophenyl)-1,3-thiazol-4-yl]methyl}sulfanyl)-4-[2-(3-hydroxypropyl)-1,3-thiazol-4-yl]pyridine-3,5-dicarbonitrile

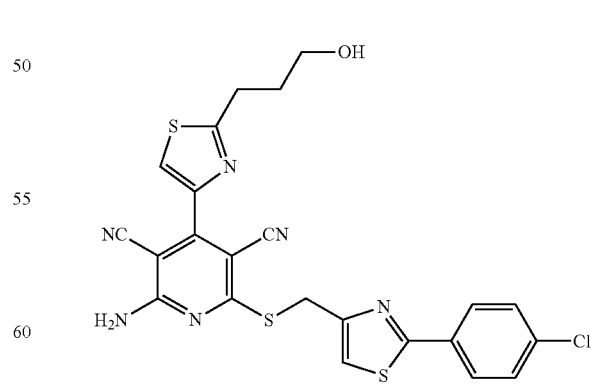

Under argon, 220 mg of the mixture from Example 22A were initially charged in 10 ml of ethyl acetate, 110 mg of palladium (10% on activated carbon) were added and the mixture was hydrogenated at atmospheric hydrogen pressure and room temperature overnight. The catalyst was filtered off through Celite, the filter cake was washed with ethyl acetate and the filtrate was concentrated. The residue was purified by preparative HPLC. This gave 31 mg (17% of theory) of the target compound.

$^1$H-NMR (400 MHz, DMSO-d$_6$): 8.40-8.00 (m br, 2H), 8.16 (s, 1H), 7.95 (d, 2H), 7.90 (s, 1H), 7.56 (d, 2H), 4.64 (s, 2H), 3.49 (t, 2H), 3.08 (t, 2H), 1.91 (m, 2H).

LC-MS (Method 7): R$_t$=1.17 min; MS (ESIpos): m/z=525 [M+H]$^+$.

Example 42

2-Amino-6-({[2-(4-chlorophenyl)-1,3-thiazol-4-yl]methyl}sulfanyl)-4-(2-{[(2S)-2,3-dihydroxypropyl]amino}-1,3-thiazol-4-yl)pyridine-3,5-dicarbonitrile

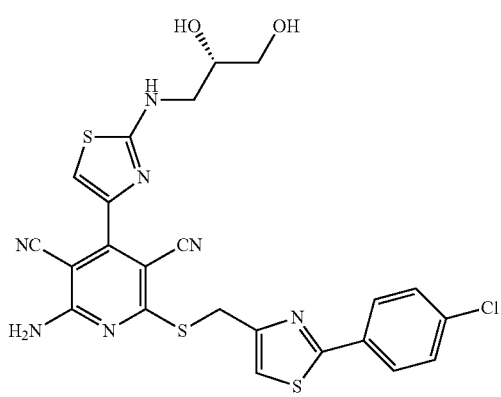 [SMILES: N#Cc1c(N)nc(SCc2csc(-c3ccc(Cl)cc3)n2)c(C#N)c1-c1csc(NC[C@H](O)CO)n1]

100 mg (0.183 mmol) of 2-amino-4-(2-bromo-1,3-thiazol-4-yl)-6-({[2-(4-chlorophenyl)-1,3-thiazol-4-yl]methyl}sulfanyl)pyridine-3,5-dicarbonitrile were initially charged in 2 ml of acetone, 834 mg (9.159 mmol) of (2S)-3-aminopropane-1,2-diol were added and the mixture was stirred at 80° C. for 12 h. A further 834 mg (9.159 mmol) of (2S)-3-aminopropane-1,2-diol were then added, and the mixture was stirred at 80° C. for a further 12 h. The reaction mixture was concentrated and the product was isolated by preparative HPLC. This gave 19 mg (19% of theory) of the target compound.

$^1$H-NMR (400 MHz, DMSO-d$_6$): 8.30-7.99 (m, 2H), 7.94 (d, 2H), 7.89 (s, 1H), 7.86 (m, 1H), 7.56 (d, 2H), 7.23 (s, 1H), 4.62 (s, 2H), 3.68 (m, 2H), 3.60-3.40 (m, 3H), 3.36 (d, 1H), 3.17 (m, 1H).

LC-MS (Method 7): R$_t$=1.09 min; MS (ESIpos): m/z=556 [M+H]$^+$.

Example 43

2-Amino-6-({[2-(4-chlorophenyl)-1,3-thiazol-4-yl]methyl}sulfanyl)-4-{2-[(2-hydroxyethyl)(methyl)amino]-1,3-thiazol-5-yl}pyridine-3,5-dicarbonitrile

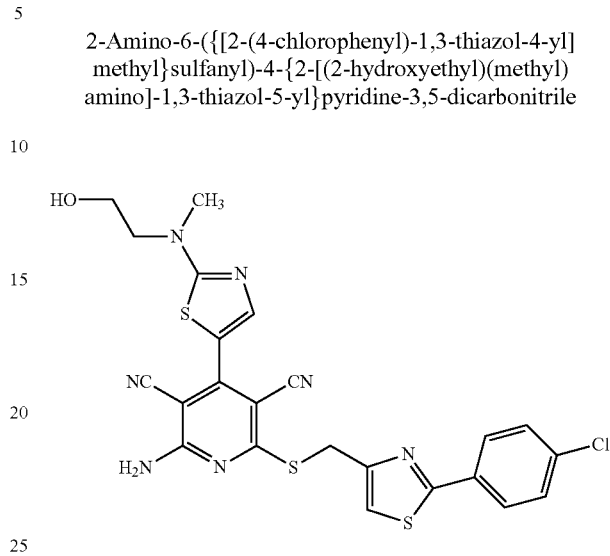

130 mg (0.219 mmol) of 2-amino-6-({[2-(4-chlorophenyl)-1,3-thiazol-4-yl]methyl}sulfanyl)-4-(2-iodo-1,3-thiazol-5-yl)pyridine-3,5-dicarbonitrile were initially charged in 2.5 ml of acetone, 0.885 ml (10.963 mmol) of 2-(methylamino)ethanol was added and the mixture was stirred at 80° C. overnight. The reaction mixture was concentrated and the product was isolated by preparative HPLC. This gave 74 mg (63% of theory) of the target compound.

$^1$H-NMR (400 MHz, DMSO-d$_6$): 8.26-8.01 (m, 2H), 7.94 (d, 2H), 7.88 (s, 1H), 7.74 (s, 1H), 7.56 (d, 2H), 4.89 (t, 1H), 4.61 (s, 2H), 3.64 (m, 2H), 3.58 (m, 2H), 3.15 (s, 3H).

LC-MS (Method 7): R$_t$=1.18 min; MS (ESIpos): m/z=540 [M+H]$^+$.

Example 44

2-Amino-6-({[2-(4-chlorophenyl)-1,3-thiazol-4-yl]methyl}sulfanyl)-4-{2-[(2-hydroxyethyl)amino]-1,3-thiazol-5-yl}pyridine-3,5-dicarbonitrile

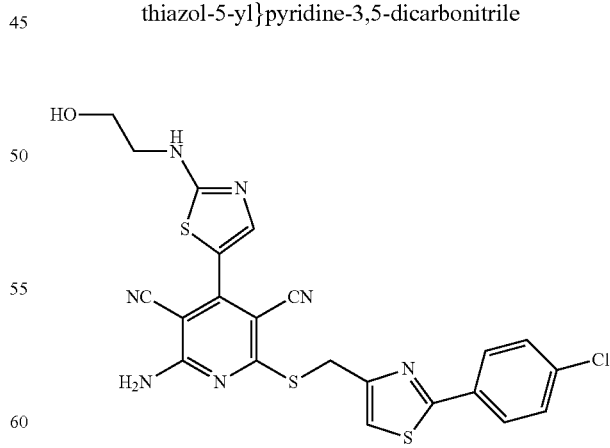

94 mg (0.159 mmol) of 2-amino-6-({[2-(4-chlorophenyl)-1,3-thiazol-4-yl]methyl}sulfanyl)-4-(2-iodo-1,3-thiazol-5-yl)pyridine-3,5-dicarbonitrile were initially charged in 2.5 ml of acetone, 0.479 ml (7.927 mmol) of 2-aminoethanol was added and the mixture was stirred at 80° C. overnight. The reaction mixture was concentrated and the product was isolated by preparative HPLC. This gave 7 mg (8% of theory) of the target compound.

¹H-NMR (400 MHz, DMSO-d₆): 8.39 (m, 1H), 8.34-7.99 (m, 2H), 7.94 (d, 2H), 7.88 (s, 1H), 7.64 (s, 1H), 7.56 (d, 2H), 4.83 (t, 1H), 4.61 (s, 2H), 3.56 (m, 2H), 3.37 (m, 2H).

LC-MS (Method 7): $R_t$=1.11 min; MS (ESIpos): m/z=526 [M+H]⁺.

The examples listed in Table 7 were prepared from the appropriate starting materials analogously to Example 19 with subsequent purification [preparative HPLC (Chromasil, water/acetonitrile, if appropriate with added acid)]:

TABLE 7

| Example No. | Structure (yield) | LC-MS: $R_t$ [min] (method); MS (ESI): m/z [M + H]⁺ | ¹H-NMR (DMSO-d₆): |
|---|---|---|---|
| 45 | (25% of theory) | 2.01 min (Method 1); m/z = 550 | δ (400 MHz) = 7.96 (d, 2H), 7.91 (d, 1H), 7.68 (s, 1H), 7.58 (d, 2H), 6.73 (d, 1H), 5.87 (d, 1H), 4.92 (t, 1H), 4.73-4.53 (m, 5H), 4.28-4.08 (m, 4H), 3.78 (t, 2H). |
| 46 | (20% of theory) | 2.59 min (Method 5); m/z = 534 | δ (400 MHz) = 7.96 (d, 2H), 7.91 (d, 1H), 7.68 (s, 1H), 7.58 (d, 2H), 6.72 (d, 1H), 4.92 (t, 1H), 4.67 (s, 2H), 4.58-4.32 (m, 4H), 4.25 (t, 2H), 3.76 (q, 2H), 2.39-2.30 (m, 2H). |

Example 47

2-({[2-(4-Chlorophenyl)-1,3-thiazol-4-yl]methyl}sulfanyl)-6-[(3R)-3-hydroxypyrrolidin-1-yl]-4-(1,3-thiazol-5-yl)pyridine-3,5-dicarbonitrile

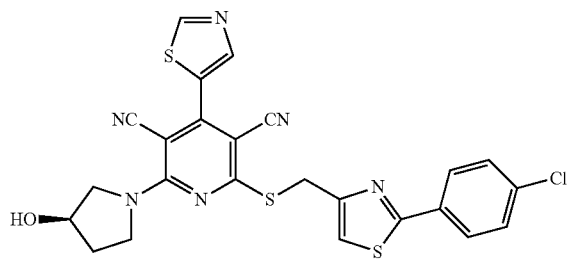 [SMILES: N#Cc1c(SCc2csc(-c3ccc(Cl)cc3)n2)nc(N2CC[C@@H](O)C2)c(C#N)c1-c1cncs1]

100 mg (about 0.186 mmol) of 2-chloro-6-({[2-(4-chlorophenyl)-1,3-thiazol-4-yl]methyl}sulfanyl)-4-(1,3-thiazol-5-yl)pyridine-3,5-dicarbonitrile were initially charged in 5 ml of THF, 33 mg (0.373 mmol) of (R)-(+)-3-pyrrolidinol were added and the mixture was stirred at room temperature for 30 min. The product was then isolated by preparative HPLC. This gave 78 mg (78% of theory) of the target compound.

$^1$H-NMR (400 MHz, DMSO-$d_6$): δ=9.40 (s, 1H), 8.28 (s, 1H), 7.95 (d, 2H), 7.70 (s, 1H), 7.57 (d, 2H), 5.15 (d, 1H), 4.71 (s, 2H), 4.40 (m, 1H), 3.92 (m, 3H), 3.76 (d, 1H), 2.10-1.80 (d, 2H).

LC-MS (Method 3): $R_t$=1.36 min; MS (ESIpos): m/z=537 [M+H]$^+$.

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. Test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$ M to $3 \times 10^{-6}$ M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase response is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", Naunyn Schmiedebergs Arch. Pharmacol., 357, 1-9 (1998)).

Table 1 below lists the $EC_{50}$ values of representative working examples for the receptor stimulation on adenosine A1, A2a and A2b receptor subtypes:

TABLE 6

| Example No. | EC50 A1 [nM] (1 µM forskolin) | EC50 A2a [nM] | EC50 A2b [nM] |
| --- | --- | --- | --- |
| 1 | 0.5 | 3000 | 1570 |
| 4 | 0.9 | 3000 | 3000 |
| 8 | 1.2 | 275 | 715 |
| 9 | 1.4 | 3000 | 3000 |
| 12 | 2.4 | 3000 | 3000 |
| 16 | 0.4 | 3000 | 3000 |
| 20 | 0.5 | 3000 | 1800 |
| 21 | 0.5 | 378 | 3000 |
| 22 | 0.6 | 2470 | 1280 |
| 27 | 1.1 | 6500 | 6500 |
| 30 | 1.9 | 2000 | 1410 |
| 32 | 0.3 | 184 | 34 |
| 37 | 0.05 | 88 | 28 |
| 47 | 0.5 | 3000 | 3000 |

B-2. Studies On Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the decrease in the contraction of the vessels is measured. A decrease in contraction corresponds to dilation of the vessels. The concentration at which the contraction of the blood vessels is reduced by 50% is given as the $EC_{50}$ value of a test substance with respect to its relaxing properties.

B-3. Measurement of Blood Pressure and Heart Rate On Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters). Blood pressure, heart rate and their changes are then recorded over a period of 24 hours.

B-4. Measurement of Blood Pressure and Heart Rate On Awake Marmosets

Various concentrations of test substances are administered orally to awake marmosets which carry an internal transmitter capable of measuring permanently both blood pressure and heart rate (telemetric monitoring of hemodynamic parameters). Blood pressure, heart rate and their changes are then recorded over a period of 6-24 hours.

B-5. Indirect Determination of Adenosine Antagonism Via Gene Expression

Cells of the permanent line CHO K1 (Chinese Hamster Ovary) are stably transfected with a reporter construct (CRE luciferase) and the cDNA for the adenosine receptor subtype A2a or A2b. A2a or A2b receptors are coupled via Gas proteins to the adenylate cyclase. Through receptor activation, the adenylate cyclase is activated and therefore the cAMP level in the cell increases. Via the reporter construct, a cAMP-dependent promoter, the change in the cAMP level is coupled to luciferase expression.

For determination of adenosine antagonism on the adenosine receptor subtype A1, once again CHO K1 cells are stably transfected, but this time with a $Ca^{2+}$-sensitive reporter construct (NFAT-TA-Luc; Clontech) and an A1-Gα 16 fusion construct. This receptor chimera is, in contrast to the native A1 receptor (Gαi-coupling), coupled to the phospholipase C. The luciferase is expressed here as a function of the cytosolic $Ca^{2+}$ concentration.

The permanent cell lines are cultured in DMEM/F12 (Cat.No. BE04-687Q; BioWhittaker) with 10% FCS (fetal calf serum) and various additives (20 ml/liter 1 M HEPES (Cat. No. 15630; Gibco), 20 ml/liter GlutaMAX (Cat. No. 35050-038, Gibco), 14 ml/liter MEM sodium pyruvate (Cat. No. 11360-039; Gibco) 10 ml/liter PenStrep (Cat. No. 15070-063; Gibco)) at 37° C. under 5% carbon dioxide, and split twice weekly.

For testing in the 384-well plate format, the cells are sown at 2000 cells/well in 25 μl/well sowing medium and cultured at 37° C. under 5% carbon dioxide until substance testing. The A2a and A2b cells are sown, 24 h before substance testing, in medium with additives and 5% FCS, the base medium used for the A2a cells being DMEM/F12 and the base medium used for the A2b cells being OptiMEM (Cat. No. 31985-047; Gibco). The A1-Gα 16 cells are sown, 48 h before substance testing, in OptiMEM with 2.5% dialysed FCS and additives. On the day of the test, prior to the addition of the substance, the medium is replaced by 25 μl of Cafty buffer (Cat. No. T21-154; PAA) with 2 mM calcium chloride and 0.1% BSA (bovine serum albumin). Dilution series in Cafty buffer with 2 mM calcium chloride and 0.1% BSA (bovine serum albumin) and a suitable agonist concentration are prepared from the substances to be tested, which are dissolved in DMSO. The substances are pipetted at a final concentration of from $5 \times 10^{-5}$ M to $2.56 \times 10^{-11}$ M to the test cultures, while the DMSO content on the cells should not exceed 0.5%. NECA (5-N-ethyl carboxamidoadenosine) at a final concentration of 30 nM, which roughly corresponds to the $EC_S$ concentration, is used as agonist for the A2a and A2b cells. 25 nM CPA (N-6-cyclopentyladenosine), which roughly corresponds to the $EC_{75}$ concentration, is used as agonist for the A1-Gα16 cells. After adding the substances, the cell plates are incubated for 3-4 h at 37° C. under 5% carbon dioxide. Then, 25 μl of a solution consisting to 50% of lysis reagent (30 nM disodium hydrogen phosphate, 10% glycerol, 3% Triton X-100, 25 mM TrisHCl, 2 mM dithiothreitol (DTT), pH 7.8) and to 50% of luciferase substrate solution (2.5 mM ATP, 0.5 mM luciferin, 0.1 mM coenzyme A, 10 mM tricin, 1.35 mM magnesium sulfate, 15 mM DTT, pH 7.8) are added to the cells directly before measurement. The luciferase activity is detected with a luminescence reader. The $IC_{50}$ values are determined, i.e. the concentration at which the luciferase response, produced by the respective agonist, is inhibited to 50%. ZM241385, for the A2a and A2b cells, and DPCPX (1,3-dipropyl-8-cyclopentylxanthine), for the A1-Gα 16 cells, are used as reference antagonist.

TABLE 7

| Example No. | IC50 A1 [nM] | EC50 A2a [nM] | EC50 A2b [nM] |
|---|---|---|---|
| 15 | 0.5 | 50 000 | 40 |
| 29 | 3.6 | 306 | 267 |

B-6. Determination of Pharmacokinetic Parameters After Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS.

The plasma concentration/time courses found in this way are used to calculate the pharmacokinetic parameters such as AUC (area under the concentration-time curve), $C_{max}$ (maximum plasma concentration), $T_{1/2}$ (half-life) and CL (clearance) by means of a validated pharmacokinetic computer program.

B-7. Determination of the Solubility

Reagents required:

PBS buffer pH 6.5: 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1 N aqueous sodium hydroxide solution (for example from Bernd Kraft GmbH, Art. No. 01030.4000) are weighed into a 1 liter measuring flask, the flask is filled with distilled water to 1 liter and the mixture is stirred for 1 hour. Using 1 N hydrochloric acid (for example from Merck, Art. No. 1.09057.1000) the pH is then adjusted to 6.5.

PEG/water solution (70:30 v/v): 70 ml of polyethylene glycol 400 (for example from Merck, Art. No. 8.17003.1000) and 30 ml of distilled water are homogenized in a 100 ml measuring flask.

PEG/PBS buffer pH 6.5 (20:80 v/v): 20 ml of polyethylene glycol 400 (for example from Merck, Art. No. 8.17003.1000) and 80 ml of PBS buffer pH 6.5 are homogenized in a 100 ml measuring flask.

Dimethyl sulfoxide (for example from Baker, Art. No. 7157.2500)

Distilled water.

Preparation of the Starting Solution (Original Solution):

At least 4 mg of the test substance are weighed accurately into a wide-necked 10 mm screw V vial (from Glastechnik Gräfenroda GmbH, Art. No. 8004-WM-H/V15μ) with fitting screw cap and septum, in a pipetting robot DMSO is added to a concentration of 50 mg/ml and the mixture is shaken for 10 minutes.

Preparation of the Calibration Solutions:

Preparation of the starting solution for calibration solutions (stock solution): with the aid of a pipetting robot, 10 μl of the original solution are transferred into a microtiter plate and made up with DMSO to a concentration of 600 µg/ml. The sample is shaken until everything has gone into solution.

Calibration solution 1 (20 µg/ml): 1000 µl of DMSO are added to 34.4 µl of the stock solution, and the mixture is homogenized.

Calibration solution 2 (2.5 µg/ml): 700 µl of DMSO are added to 100 µl of calibration solution 1, and the mixture is homogenized.

Preparation of the Sample Solutions:

Sample solution for solubilities of up to 5 g/liter in PBS buffer pH 6.5: 10 µl of the original solution are transferred into a microtiter plate, and 1000 µl of PBS buffer pH 6.5 are added.

Sample solution for solubilities of up to 5 g/liter in PEG/water (70:30): 10 µl of the original solution are transferred into a microtiter plate, and 1000 µl of PEG/water (70:30) are added.

Sample solution for solubilities of up to 5 g/liter in PEG/PBS buffer pH 6.5 (20:80): 10 µl of the original solution are transferred into a microtiter plate, and 1000 µl of PEG/PBS buffer pH 6.5 (20:80) are added.

Practice:

The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 µl are taken from these solutions and transferred into Beckman Polyallomer Centrifuge Tubes (Art. No. 343621). These solutions are centrifuged at about 223 000×g for one hour (for example Beckman Optima L-90K Ultracentrifuge with Type 42.2 Ti Rotor at 42 000 rpm). From each of the sample solutions, 100 µl of the supernatant are removed and diluted 1:5 and 1:100 with DMSO. From each dilution, a sample is transferred into a vessel suitable for HPLC analysis.

Analysis:

The samples are analysed by RP-HPLC. Quantification is carried out using a two-point calibration curve of the test compound in DMSO. The solubility is expressed in mg/liter. Analysis sequence: 1) calibration solution 2.5 mg/ml; 2) calibration solution 20 µg/ml; 3) sample solution 1:5; 4) sample solution 1:100.

HPLC Method for Acids:

Agilent 1100 mit DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; mobile phase A: water+5 ml of perchloric acid/liter; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

B-8. Determination of the Metabolic Stability

To determine the metabolic stability of test compounds, the latter are incubated in vitro with liver microsomes or, preferably, with primary fresh hepatocytes of various animal species (for example from rat and dog) and also of human origin to obtain and to compare metabolite profiles of a hepatic phase I and phase II metabolism which is as complete as possible.

The test compounds are incubated at a concentration of 10-20 µM. To this end, stock solutions of the substances at a concentration of 1-2 mM in acetonitrile are prepared and then pipetted at a dilution of 1:100 into the incubation mixture. The liver microsomes are incubated at 37° C. in 50 mM potassium phosphate buffer (pH 7.4) with and without NADPH-generating system consisting of 1 mM NADP$^+$, 10 mM glucose 6-phosphate and 1 unit of glucose 6-phosphate dehydrogenase. Primary hepatocytes are also incubated at 37° C. in suspension in Williams E medium. After an incubation time of 0-4 hours, the incubation mixtures are quenched with acetonitrile (final concentration about 30%) and the protein is centrifuged off at about 15 000×g. The samples quenched in this manner are either analyzed directly or stored at −20° C. until analysis.

Analysis is carried out using high-performance liquid chromatography with ultraviolet and mass-spectrometric detection (HPLC-UV-MS/MS). To this end, the supernatants of the incubation samples are chromatographed using suitable C18 reversed-phase columns and variable mobile phase mixtures of acetonitrile and 10 mM aqueous ammonium formate solution. The UV chromatograms in combination with mass-spectrometric MS/MS data serve to identify the metabolites and to elucidate their structures.

C. WORKING EXAMPLES OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate. Tablet weight 212 mg, diameter 8 mm, radius of curvature 12 mm.

Production:

The mixture of compound of the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be administered orally:

Composition:

1000 mg of the compound of the invention, 1000 mg of ethanol (96%), 400 mg of Rhodigel® (xanthan gum from FMC, Pennsylvania, USA) and 99 g of water. 10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be administered orally:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I):

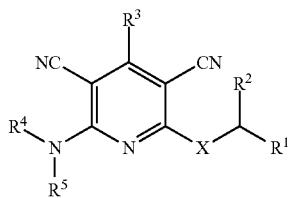

(I)

wherein
X represents O or S,
$R^1$ represents phenyl or 5- or 6-membered heteroaryl,
where phenyl and 5- or 6-membered heteroaryl are substituted by 1 or 2 substituents independently of one another selected from the group consisting of fluorine, chlorine, cyano, $(C_1-C_4)$-alkyl, trifluoromethyl, $(C_1-C_4)$-alkoxy, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, pyrrolidino, piperidino, morpholino, piperazino, N'-$(C_1-C_4)$-alkylpiperazino, phenyl and 5- or 6-membered heteroaryl,
where phenyl and 5- or 6-membered heteroaryl may be substituted by 1 or 2 substituents independently of one another selected from the group consisting of fluorine, chlorine, cyano, $(C_1-C_4)$-alkyl, difluoromethyl, trifluoromethyl, $(C_1-C_4)$-alkoxy, difluoromethoxy, trifluoromethoxy, hydroxycarbonyl and $(C_1-C_4)$-alkoxycarbonyl,
$R^2$ represents hydrogen or methyl,
$R^3$ represents pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-5-yl, pyrazol-1-yl, pyrazol-3-yl, pyrazol-4-yl, pyrazol-5-yl, imidazol-1-yl, imidazol-2-yl, imidazol-4-yl or imidazol-5-yl, where pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-5-yl, pyrazol-1-yl, pyrazol-3-yl, pyrazol-4-yl, pyrazol-5-yl, imidazol-1-yl, imidazol-2-yl, imidazol-4-yl and imidazol-5-yl may be substituted by 1 or 2 substituents independently of one another selected from the group consisting of fluorine, trifluoromethyl $(C_1-C_6)$-alkyl, $(C_1-C_4)$-alkoxy and —$NR^AR^B$, where $(C_1-C_6)$-alkyl and $(C_2-C_4)$-alkoxy may be substituted by 1 or 2 substituents independently of one another selected from the group consisting of fluorine, trifluoromethyl, hydroxyl, methoxy, ethoxy, hydroxycarbonyl, amino, methylamino, ethylamino, N,N-dimethylamino and N,N-diethylamino, and where
$R^A$ represents hydrogen or $(C_1-C_4)$-alkyl,
where $(C_1-C_4)$-alkyl for its part may be substituted by a substituent selected from the group consisting of hydroxyl and $(C_1-C_4)$-alkoxy,
$R^B$ represents hydrogen or $(C_1-C_4)$-alkyl,
where $(C_1-C_4)$-alkyl for its part may be substituted by 1 or 2 substituents independently of one another selected from the group consisting of hydroxyl, $(C_1-C_4)$-alkoxy and hydroxycarbonyl,
$R^4$ represents hydrogen or methyl,
$R^5$ represents hydrogen or $(C_1-C_4)$-alkyl,
where $(C_1-C_4)$-alkyl may be substituted by 1 or 2 substituents independently of one another selected from the group consisting of hydroxyl, methoxy and ethoxy, or
$R^4$ and $R^5$ together with the nitrogen atom to which they are attached form a 4- to 6-membered heterocycle which may contain a further ring heteroatom from the group consisting of N, O and S and may be substituted by 1 or 2 substituents independently of one another selected from the group consisting of $(C_1-C_4)$-alkyl, hydroxyl, methoxy and ethoxy,
or a salt thereof.

2. The compound of claim 1, wherein:
X represents S,
$R^1$ represents phenyl, oxazolyl, thiazolyl or pyridyl,
where phenyl and pyridyl are substututed by a substituent selected from the group consisting of cyano, methoxy, ethoxy, hydroxycarbonyl, methoxycarbonyl, ethoxycarbonyl, aminocarbonyl, methylaminocarbonyl and dimethylaminocarbonyl, and
where phenyl and pyridyl may by substituted by a substituent selected from the group consisting of fluorine, chlorine, methyl, ethyl and trifluoromethyl, and
where oxazolyl and thiazolyl are substituted by a phenyl substituent,
where phenyl may be substituted by a substituent selected from the group consisting of fluorine, chlorine, cyano, methyl, methoxy, hydroxycarbonyl and methoxycarbonyl, and
where oxazolyl and thiazolyl may be substituted by a substituent selected from the group consisting of fluorine, methyl, ethyl, methoxy, hydroxycarbonyl and methoxycarbonyl,
$R^2$ represents hydrogen,
$R^3$ represents a group of the formula

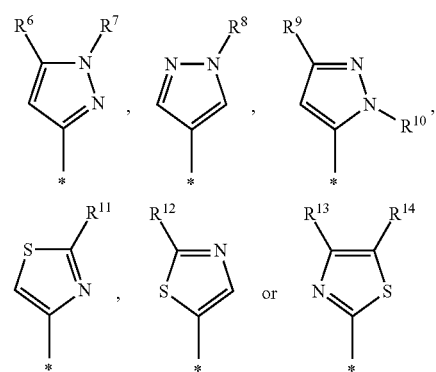

where
* denotes the point of attachment to the pyridine, and
where
$R^6$ represents hydrogen, methyl or ethyl,
$R^7$ represents hydrogen or $(C_1-C_6)$-alkyl,
  where $(C_1-C_6)$-alkyl may be substituted by 1 or 2 substituents independently of one another selected from the group consisting of hydroxyl and methoxy,
$R^8$ represents hydrogen or $(C_1-C_6)$-alkyl,
  where $(C_1-C_6)$-alkyl may be substituted by 1 or 2 substituents independently of one another selected from the group consisting of hydroxyl and methoxy,
$R^9$ represents hydrogen, methyl or ethyl,
$R^{10}$ represents hydrogen,
$R^{11}$ represents hydrogen or $(C_1-C_6)$-alkyl,
  where $(C_1-C_6)$-alkyl may be substituted by 1 or 2 substituents independently of one another selected from the group consisting of hydroxyl and methoxy,
$R^{12}$ represents hydrogen or $(C_1-C_6)$-alkyl,
  where $(C_1-C_6)$-alkyl may be substituted by 1 or 2 substituents independently of one another selected from the group consisting of hydroxyl and methoxy,
$R^{13}$ represents hydrogen, methyl or ethyl, and
$R^{14}$ represents hydrogen or $(C_1-C_6)$-alkyl,
  where $(C_1-C_6)$-alkyl may be substituted by 1 or 2 substituents independently of one another selected from the group consisting of hydroxyl and methoxy,
$R^4$ represents hydrogen,
$R^5$ represents hydrogen, ethyl, n-propyl or sec-butyl,
  where ethyl, n-propyl and sec-butyl may be substituted by 1 or 2 hydroxyl substituents, or
$R^4$ and $R^5$ together with the nitrogen atom to which they are attached form an azetidinyl or pyrrolidinyl ring which may be substituted by a hydroxyl substituent,
or a salt thereof.

3. A process for preparing compounds of the formula (I) as defined in claim 1, comprising:
[A] reacting a compound of the formula (II)

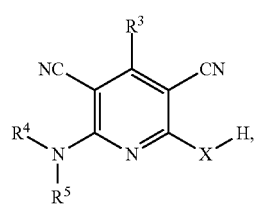

(II)

in which X, $R^3$, $R^4$ and $R^5$ have the meanings given in claim 1, in an inert solvent in the presence of a base with a compound of the formula (III)

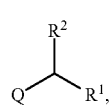

(III)

in which $R^1$ and $R^2$ each have the meanings given in claim 1 and
Q represents a suitable leaving group, preferably halogen, in particular chlorine, bromine or iodine, or represents mesylate, tosylate or triflate, or

[B] if X represents O, a compound of the formula (IV)

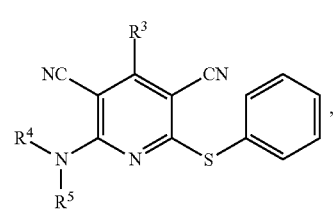

(IV)

in which $R^3$, $R^4$ and $R^5$ each have the meanings given in claim 1, in an inert solvent in the presence of a base with a compound of the formula (V)

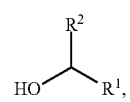

(V)

in which $R^1$ and $R^2$ have the meanings given in claim 1, or

[C] converting a compound of the formula (I-A)

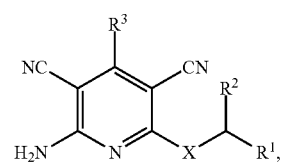

(I-A)

in which $R^1$, $R^2$ and $R^3$ each have the meanings given in claim 1, with copper(II) chloride and isoamyl nitrite in a suitable solvent into a compound of the formula (XV)

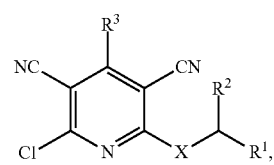

(XV)

in which $R^1$, $R^2$ and $R^3$ each have the meanings given in claim 1, and reacting the compound of formula (XV) with a compound of the formula (VIII)

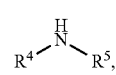

(VIII)

in which $R^4$ and $R^5$ each have the meanings given in claim 1, and
in which at least one of the two radicals $R^4$ and $R^5$ is different from hydrogen, to give a compound of the formula (I-B)

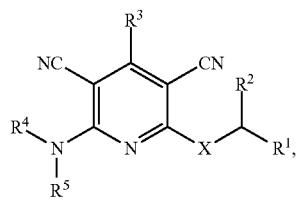
(I-B)

in which $R^1$, $R^2$, $R^3$, $R^4$ and $R^5$ each have the meanings given claim 1, and in which at least one of the two radicals $R^4$ and $R^5$ is different from hydrogen, any protective groups present are then removed and optionally converting the resulting compound of formula (I) with the appropriate (i) solvent and/or (ii) bases or acid into a salt thereof.

4. A pharmaceutical composition, comprising a compound of claim 1 and an inert nontoxic pharmaceutically suitable auxiliary.

5. The pharmaceutical composition of claim 4, further comprising one or more further active ingredients selected from the group consisting of lipid metabolism-modifying active ingredients, antidiabetics, antihypertensive drugs and antithrombotic drugs.

\* \* \* \* \*